United States Patent

Gargano et al.

[11] Patent Number: 5,814,015
[45] Date of Patent: Sep. 29, 1998

[54] INFUSION PUMP FOR AT LEAST ONE SYRINGE

[75] Inventors: Diane A. Gargano, Cambridge; Eric J. Flachbart, Hamilton; Barry Cowen, Waltham; Monica Duh, Lincoln; John L. Rudser, Jr., Westwood; Ken Zhen, Cambridge; Lynn Noble, Lexington; Julian Warhurst, Ashland; Luis Pedraza, West Roxbury, all of Mass.

[73] Assignee: Harvard Clinical Technology, Inc., South Natick, Mass.

[21] Appl. No.: 394,441

[22] Filed: Feb. 24, 1995

[51] Int. Cl.⁶ ............................................. A61M 31/00
[52] U.S. Cl. ............................ 664/67; 604/151; 604/155
[58] Field of Search ........................... 604/131, 151, 604/152, 154, 155, 65, 66, 67

[56] References Cited

U.S. PATENT DOCUMENTS

| | | | |
|---|---|---|---|
| 3,631,847 | 1/1972 | Hobbs | 128/2 R |
| 3,858,581 | 1/1975 | Kamen | 128/218 A |
| 4,191,187 | 3/1980 | Wright | 128/218 A |
| 4,405,318 | 9/1983 | Whitney et al. | 604/155 |
| 4,424,720 | 1/1984 | Bucchianerri | 604/155 X |
| 4,435,173 | 3/1984 | Siposs et al. | 604/155 |
| 4,465,474 | 8/1984 | Mardorf et al. | 604/154 |
| 4,529,401 | 7/1985 | Leslie et al. | 604/15 X |
| 4,544,369 | 10/1985 | Skakoon et al. | 604/155 |
| 4,560,979 | 12/1985 | Rosskopf | 604/154 X |
| 4,562,751 | 1/1986 | Nason et al. | 74/111 |
| 4,563,175 | 1/1986 | LaFond | 604/155 |
| 4,617,016 | 10/1986 | Blomberg | 604/155 |
| 4,678,408 | 7/1987 | Nason et al. | 417/410 |
| 4,685,903 | 8/1987 | Cable et al. | 604/154 |
| 4,731,058 | 3/1988 | Doan | 604/155 |
| 4,741,732 | 5/1988 | Crankshaw et al. | 604/155 X |
| 4,767,406 | 8/1988 | Wadham et al. | 604/155 |
| 4,804,368 | 2/1989 | Skakoon et al. | 604/155 |
| 4,833,384 | 5/1989 | Munro et al. | 318/687 |

(List continued on next page.)

FOREIGN PATENT DOCUMENTS

| | | |
|---|---|---|
| 977641 | 11/1975 | Canada . |
| 1204975 | 5/1986 | Canada . |
| 0354852 | 2/1990 | European Pat. Off. . |
| 2724538C3 | 3/1984 | Germany . |
| 1445472 | 8/1976 | United Kingdom . |
| 1484394 | 9/1977 | United Kingdom . |
| 2115495 | 9/1983 | United Kingdom . |
| 2197930 | 6/1988 | United Kingdom . |
| 222444 | 5/1990 | United Kingdom . |
| WO8906145 | 7/1989 | WIPO . |
| WO9010468 | 9/1990 | WIPO . |

*Primary Examiner*—Danton D. DeMille
*Assistant Examiner*—Sam Rimell
*Attorney, Agent, or Firm*—Weingarten, Schurgin, Gagnebin & Hayes LLP

[57] ABSTRACT

A processor driven syringe pump for one or more, typically two syringes, which are held vertically in corresponding pumping stations of a housing unit which itself is typically suspended from an IV pole. The pump features a central display having portions corresponding to each of the syringes operated by the pump. A data entry knob cooperative with a display processor, causes a cursor issue on the display to step through and choose the menu selections. A function knob is operative to select five operating states including: Purge, Setup, Stop, Run and Bolus in a virtual or software driven manner. The syringe holding station includes a pusher assembly having plunger clamp assembly and a load cell to measure force exerted on the plunger flange. An actuation pad and associated linkage provides for easy syringe flange capturing, while a syringe barrel clamp provides for easy syringe loading and secure syringe barrel positioning for many sizes of syringe. The pump operates in a rate, volume per time, or pharmacokinetic mode. The software provides a number of feedback warnings and alarms. The pump may be provided with a drug library. The syringe plunger is driven into the syringe barrel by a motor operated by a charge pump which provides a failsafe feature. The pusher assembly for the syringe includes a split nut that on actuation pad rotation releases to allow proper positioning of the syringe.

61 Claims, 66 Drawing Sheets

U.S. PATENT DOCUMENTS

| | | | |
|---|---|---|---|
| 4,838,857 | 6/1989 | Strowe et al. | 604/67 |
| 4,898,578 | 2/1990 | Rubalcaba, Jr. | 604/66 |
| 4,952,205 | 8/1990 | Mauerer et al. | 604/67 |
| 4,978,335 | 12/1990 | Arthur, III | 604/67 |
| 4,988,337 | 1/1991 | Ito | 604/154 |
| 5,041,086 | 8/1991 | Koenig et al. | 604/65 |
| 5,139,484 | 8/1992 | Hazon et al. | 604/154 |
| 5,176,502 | 1/1993 | Sanderson et al. | 417/18 |
| 5,244,461 | 9/1993 | Derlien | 604/154 X |
| 5,254,096 | 10/1993 | Rondelet et al. | 604/152 |
| 5,256,157 | 10/1993 | Samiotes et al. | 604/67 X |
| 5,295,967 | 3/1994 | Rondelet et al. | 604/154 |
| 5,298,022 | 3/1994 | Bernardi | 604/66 |
| 5,378,231 | 1/1995 | Johnson et al. | 604/67 |
| 5,382,232 | 1/1995 | Hague et al. | 604/65 |
| 5,494,036 | 2/1996 | Uber, III et al. | 604/131 X |
| 5,507,412 | 4/1996 | Ebert et al. | 604/67 X |
| 5,545,140 | 8/1996 | Conero et al. | 604/154 |
| 5,547,470 | 8/1996 | Johnson et al. | 604/67 |

Fig. 29  When user turns knob, other selections will appear.

INFUSION PUMP FOR AT LEAST ONE SYRINGE

FIELD OF THE INVENTION

The present invention relates to the field of infusion pumps, and in particular, to an infusion pump system having one or more individually controlled pumps, simplified controls, and respective multi-line displays.

BACKGROUND OF THE INVENTION

Syringe pumps conventionally consist of a pole or table mounted unit in which a syringe from which fluid material is to be pumped is cradled in a vertical or horizontal position within a syringe pump designed to fit a specific size or range of sizes.

However, the user interface on such pumps is typically complex, cluttered, and incompatible with syringe pump internal function upgrades. Exemplary interfaces provide large footprint keyboards, dedicated function keys, or manually adjusted knobs having plural, hard-wired detents for each variable. Such interfaces typically allow limited automatic mode transition, relying upon spring loaded knobs or dials; manual intervention is most often required to change pump mode. Displayed information is typically less than comprehensive and is incompatible with efforts at customizing complex infusion regimens. Such pumps further fail to provide sequential or simultaneous infusions from plural syringes, fail to allow simple customized entry of drug information along with default administration conditions for a wide range of drug types and chemistries, and fail to provide ease of insertion or installation of the syringe in the vertical orientation.

SUMMARY OF THE INVENTION

These and other deficiencies of prior art syringe pumps are corrected in accordance with the teaching of the present invention.

The processor driven syringe pump for one or more, typically two syringes, which are held vertically in corresponding pumping stations of a housing unit which itself is typically suspended from an IV pole. The pump features, in the case of two syringe holding stations, a central display, typically a color or monochrome back lit liquid crystal or plasma display having first and second portions, one corresponding to each of the syringes operated by the pump. The syringe holding station includes a pusher assembly having a plunger clamp assembly in which a top plate over a load cell is provided to measure force exerted on the plunger flange, and front and back clamps which are positioned beneath the plunger flange and notched to fit around the plunger itself, securely cradling the plunger between the top plate and the clamps. An actuation pad and linkage separates the two clamps in a manner to facilitate plunger flange installation. The two clamps close by spring force, thus capturing the plunger securely from two sides as the actuation pad is released.

Below the display screen, for each syringe station, a data entry knob cooperative with a display processor is provided which, upon turning, causes a selection highlighter issue on the display to step through the menu selections. Knob pushing causes selection of the highlighted menu item, which may cause a numerical field to open, a pull-down menu of selectable parameters to be displayed, or a new screen and/or pumping state to be reached. The menu typically includes several layers to permit a large array of selections and commands to be accessible through a small window area. Each syringe station corresponds to the right or left portion of the split screen display and each operates independently, although a single display screen is provided. Below the data entry knob is a function select knob which is operative to select five operating states including Purge, Setup, Stop, Run and Bolus in a virtual or software driven selection manner such that transition from one state to another is controlled by software, thus preventing transition despite rotation if conditions under processor control are improper for that transition, and allowing the pump state to change without the user having to adjust the knob.

The syringe pump operates in a rate, volume or amount per time, or pharmacokinetic mode by accepting input selections for a regimen and displaying operating conditions, in that format, a format which is more intuitive for operating medical personnel. The software provides a number of feedback warnings and alarms including battery status, remaining infusion time, indications that, where a regimen provides for bolus infusion, that the bolus is insufficient, and empty syringe, among others. The software further provides a continuous indication of remaining battery life on the display. The pump may be provided with a drug library in its internal memory or may be user-entered via an interface from a personal or other computer which can simplify the selection and identification of drugs and default regimens for the drugs as well. In one embodiment, a PC program enables creation and modification of the drug library prior to its downloading to the pump.

The plunger is driven downward into the syringe barrel by a motor system referred to as a pusher assembly. The pump motor is operated by multiple processor controls including a hardware charge pump which provides a failsafe feature against a short circuit in a drive circuit element feeding continuous current into the pump motor.

The pusher assembly includes a split nut which is forced around a drive screw driven by the motor. The split nut is positioned within a tapered aperture frame or lock plate which is linked to an actuation pad or lever that opens the plunger clamps, such that upon lever activation the tapered aperture in the lock plate moves downward allowing the split nut to open due to the force provided by the torsion spring. When the lever returns to its resting position the lock plate moves upwards providing a substantial leverage advantage to close the split nut against a spring providing positioning of the lock plate so that a plunger flange can be securely nested between the plunger clamps and a top plate.

Also disclosed are further embodiments of the present invention in which: the pump is responsive to commands from a patient for increased dosage (patient controlled analgesia or PCA); two pumps are jointly programmable and operable to allow the automatic stopping of a first pump and starting of a second pump for extended sequential infusion; and a multiple station, modular infusion system for user customized combinations of syringe pumps and/or volumetric pumps.

BRIEF DESCRIPTION OF THE DRAWINGS

These and other features of the present invention are more fully set forth below in the fully exemplary detailed description and accompanying drawings of which.

DETAILED DESCRIPTION OF THE INVENTION

Figure 1:
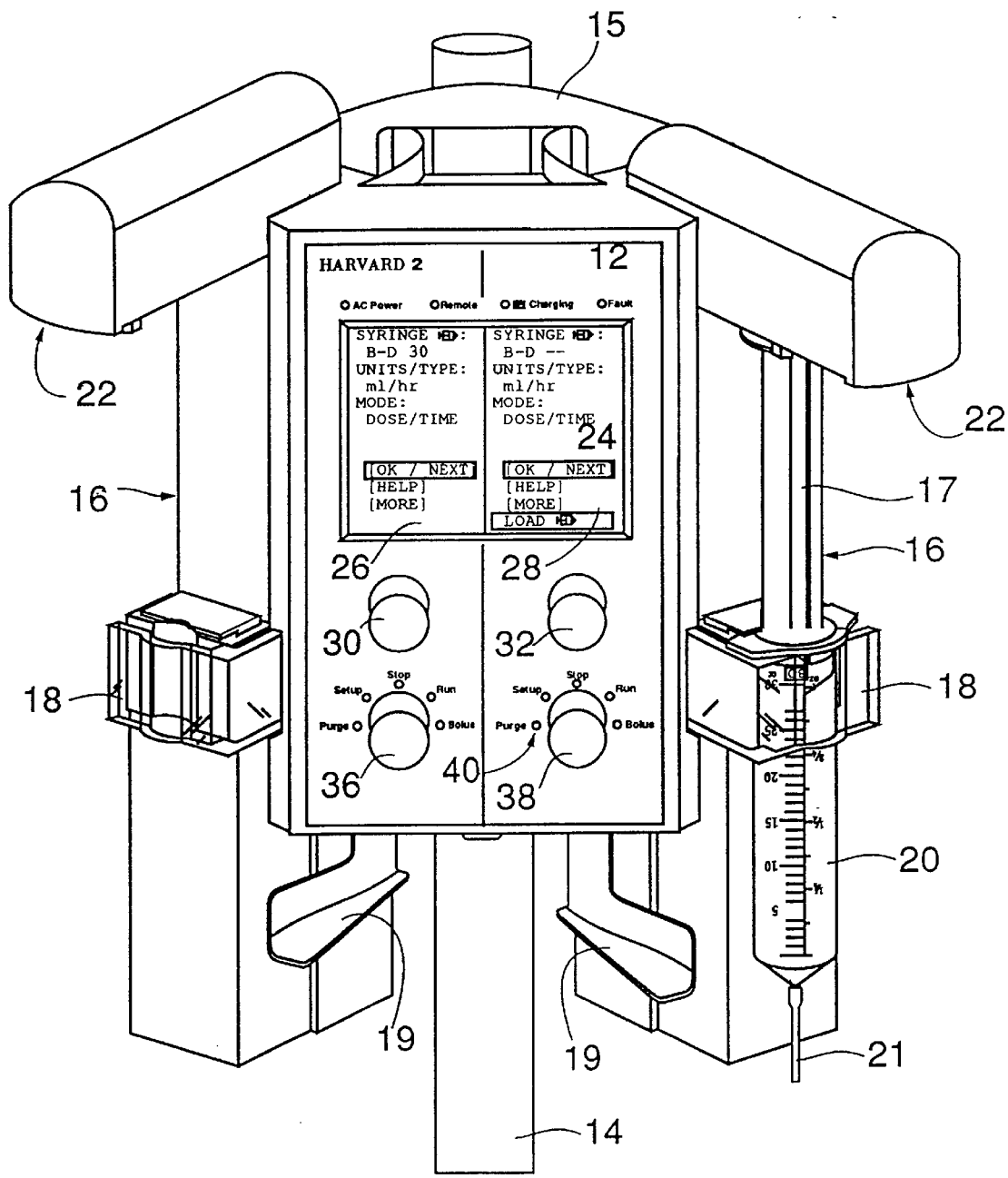
FIG. 1 is a schematic view of a preferred implementation of a plural syringe pumping station according to the invention.

The present invention as illustrated in FIG. 1 contemplates a pole mount control unit 12 attached to an IV pole 14 by conventional clamping means at the rear, not shown, and having arrayed about it one or more syringe docking or holding stations 16. The syringe holding station includes a syringe barrel clamp 18, activated by a paddle 19, in which the barrel 20 of a syringe is secured. A pusher assembly 22 securely holds a plunger flange against a load cell to sense plunger pressure as a plunger 17 is driven downward into the syringe body 20 held within the clamp 18 to force fluid into a line 21. A handle 15 is provided atop the control unit.

The control unit 12 has a display 24, typically a back lit LCD, which is typically divided into first and second portions 26, 28 for respective first and second syringes controlled by the control unit 12. In an alternative embodiment, the present control unit 12 has a plasma display. The display 24 is preferably a color display, though a monochrome embodiment is also envisioned. Below the display 12 are command identification and select controls including left and right hand data entry knobs 30, 32, also referred to as menu roam dials, each corresponding to the display portion above it and to the controlled syringe associated therewith. The data entry knobs 30, 32 are software driven such that rotation thereof moves a highlighter, such as a video inversion segment, past each data entry line in the display 24. The knobs 30, 32 have a push to select function such that pushing of a knob 30, 32 with the highlighter at a corresponding selection causes that selection to be entered by the control unit 12. The selection may invoke a pull-down menu through which the user can select another item by again turning then pushing the knob 30, 32 to select the new item. The selection may also open up a numerical field, allowing its value to be changed by turning and depressing the knob 30, 32 to enter the new value. Further, the selection may include selection of a specific portion of an infusion regimen or the selection of a further menu in one or more layers to permit access to a large range of menu selectable commands or information or the selection of a new state.

Below each knob 30 and 32 are corresponding plunger drive state selectors having function selection knobs 36, 38 which, upon manual rotation, select among five functions: purge, setup, stop, run, and bolus, that are available to the system. A series of five lights 40, such as LED lights, are disposed about each of the function knobs 36, 38 and indicate which of the five functions (purge, setup, stop, run and Bolus) are operative at any one moment. Alternatively, the LED's associated with the function knobs 36, 38 are located elsewhere on the front panel of the control unit 12, for instance proximate the display 24. These function knobs 36, 38 also software operated to select among functions without user intervention. Because the switch between functions is software controlled, the control unit 12, as described below, prevents switching between functions if conditions under software monitoring are not correct. Additionally, this software control allows the software itself to switch functions based upon operation of a state being finished or acceptance of a data entry knob 30, 32 selection. For example, upon the successful completion of a Bolus (Bolus LED lit), the software causes the function to electronically switch to the Run state (Run LED lit) without the switch mechanically moving. The software also analyzes sensor indications such as alarms, as described below, in determining whether a function transition is allowable.

Figure 2:
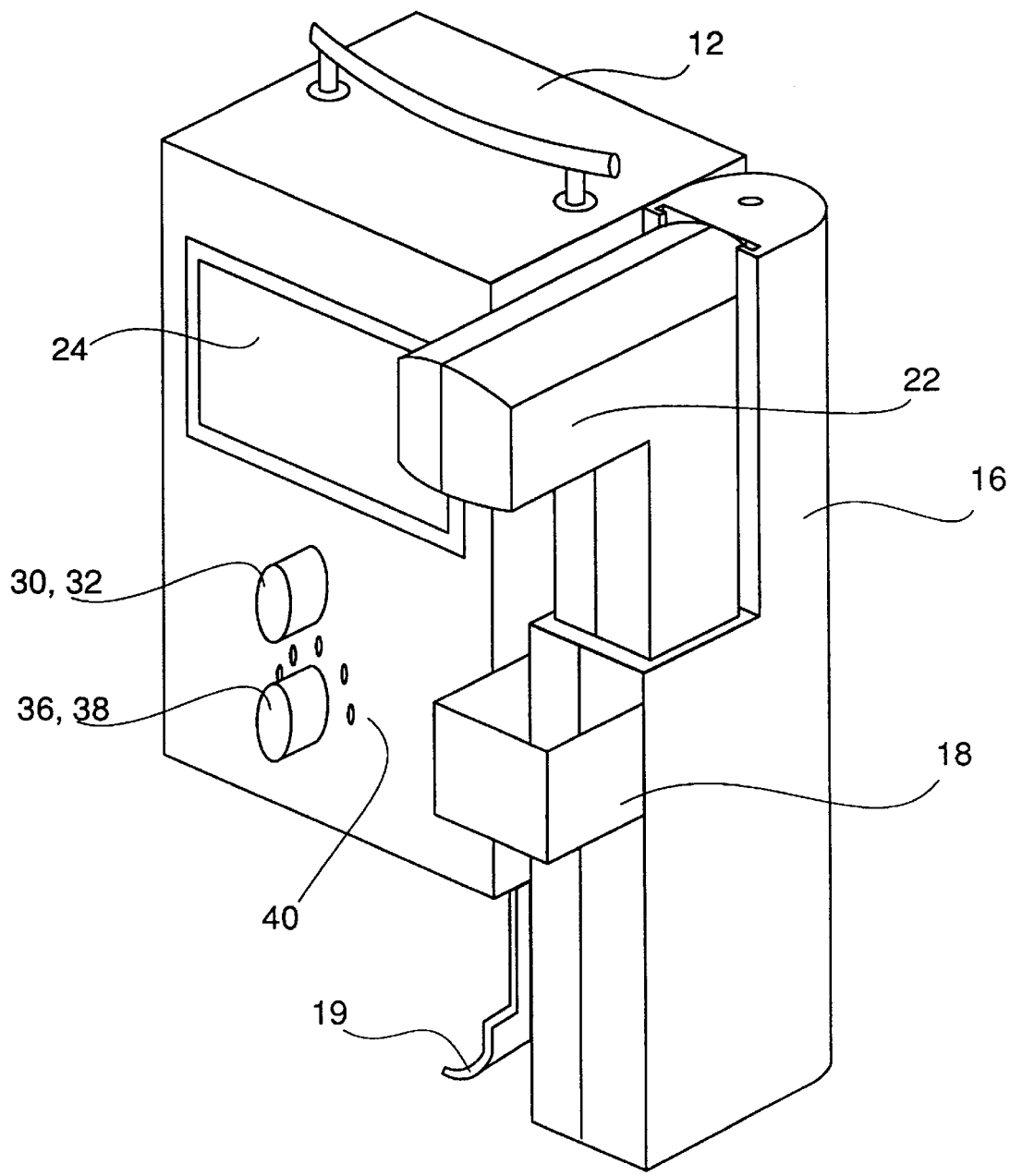
FIG. 2 is a perspective view of an alternative embodiment of the syringe pumping station according to the invention.

An alternative embodiment of the present invention is illustrated in FIG. 2, wherein only one syringe docking or holding station 16 is associated with a respective control unit 12. As a result, there is only one data entry knob 30, 32 and only one function selection knob 36, 38. Further, rather than having a split display for two or more docking stations 16, the display 24 of FIG. 2 is undivided. For the sake of clarity, a syringe 20 has been omitted from the syringe barrel clamp 18 in FIG. 2. In all other respects, the embodiment of FIG. 2 is the same in form and function as the embodiment of FIG. 1.

Figure 3:
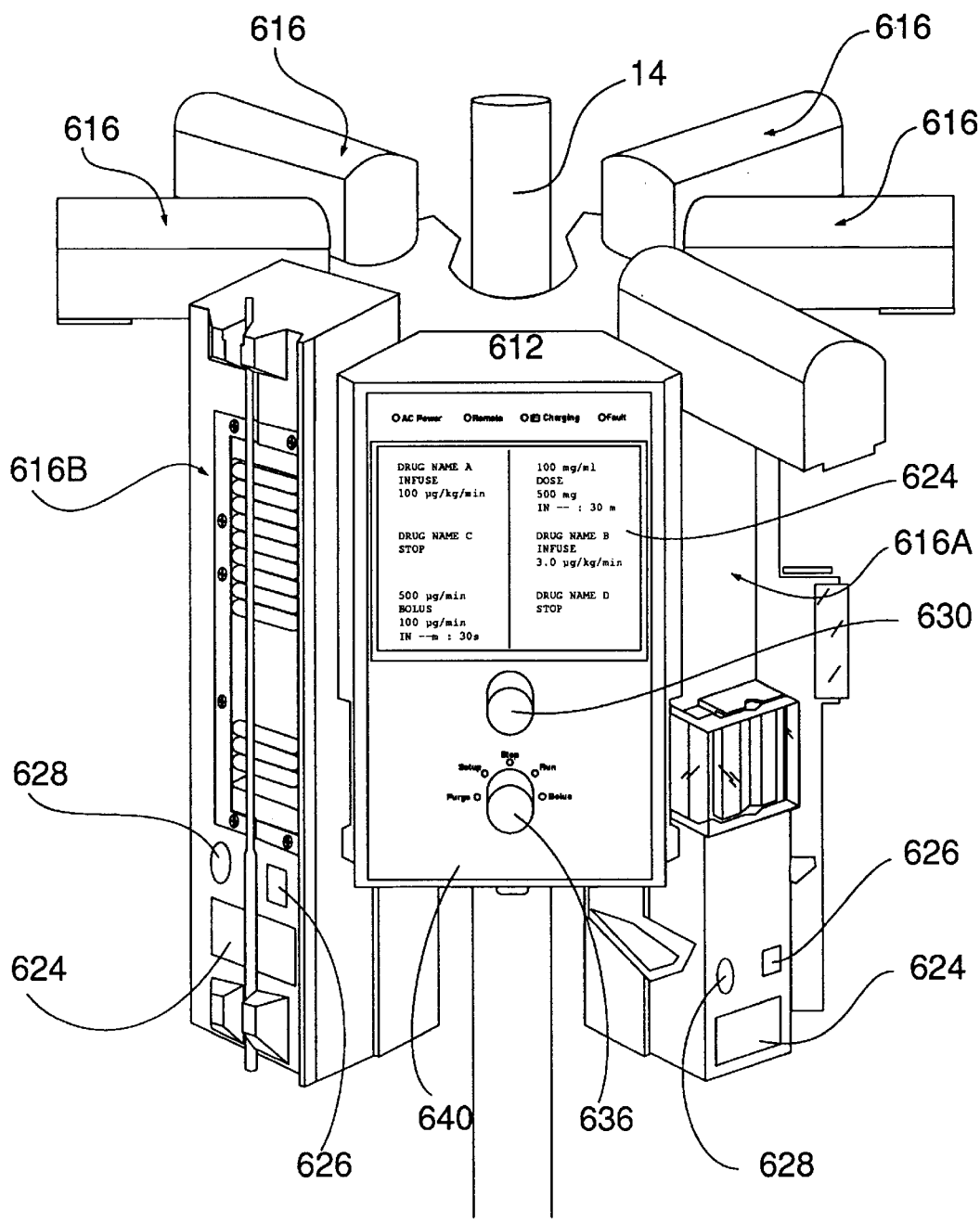
FIG. 3 is a perspective view of a further alternative embodiment of the syringe pumping station according to the invention.

In a further alternative embodiment of the present invention illustrated in FIG. 3, the control unit 612, which encircles and is attached to a pole 14 for easy access and space conservation, provides an infusion module interface 616 in place of the syringe docking or holding stations 16 shown in FIG. 1. These module interfaces enable the interconnection of up to eight pump modules adapted for either syringe contents infusion or for continuous infusion of a large volume. Other configurations interface more or less than eight modules 616.

Thus, one type of pump module in this alternative embodiment is a syringe pump module 616A similar in function to the syringe docking stations 16 illustrated in FIG. 1, with the exception that the syringe pump module 616A is removable from the control unit 612 and receives power from, and communicates over a serial communications link such as an RS-232 with, the control unit 612 via a module interface. Another type of pump module to be used with this alternative embodiment is a volumetric pump module like a peristaltic pump module 616B or a volumetric cassette pumping module (not shown) which enables continuous infusion of large volumes. Once again, this module 616B has an interface for removable connection to a suitably adapted control unit 612. Regardless of configuration, each pump module 616A, 616B contains a pumping mechanism also referred to as a pusher assembly 22 (as described below with reference to FIGS. 7, 8 and 9), motor drive circuitry, an LCD 624 for displaying a drug name or drug concentration, a confirmation button 626 for enabling a user to verify the displayed contents of the attached container, and an LED 628, typically red, to indicate a failure condition.

Control over these detachable pump modules 616A, 616B is provided by a control unit 612 having an undivided display, similar in appearance to the display 24 in FIG. 1. However, in contrast to the control unit 12 of FIG. 1, the presently described alternative embodiment has one data entry knob 630 and one function selection knob 636 for all pump modules. An upper level display screen provides information such as drug name or concentration, infusion, bolus, or dose data, and operational information such as current function for all attached pump modules 616A, 616B. A touch sensitive overlay can be provided on the display 624 in this embodiment to enable invocation of lower level screens which provide more detailed information for only one of the pump modules 616A, 616B. The data entry knob 630 can also be used to invoke such lower level screens by highlighting a drug name or concentration and depressing the knob 630. Once one pump module 616A, 616B is selected, the data entry knob 630 and the function knob 636 affect only the displayed parameters and mode of that one pump module 616A, 616B. The appropriate mode LED 640 about the function selection knob 636 will light. The control unit 612 further provides battery power to the individual modules 616A, 616B.

Note that while pertinent information is displayed at all times for all modules, more detailed information including infusion parameters and statistics are displayed for only one module 616A, 616B at a time. The control unit 612 keeps track of the infusion parameters and statistics for all attached modules 616A, 616B. Just as with the first embodiment described herein, if one module 616B has been designated as providing a "carrier" such as saline and another pump 616A or pumps are providing drugs, the control unit 612 can automatically adjust the rate of flow of the carrier depending upon the flow rate of the associated drugs, thus to provide a constant total flow.

In order to provide a safeguard against the infusion of an incorrect material into a patient, the following procedure must be followed when introducing a new module 616A, 616B to the control unit 612. Once this new module has been attached, the red LED 628 found thereon is lit, and the user is prompted to enter the drug name or concentration for the drug being infused by the newly introduced module 616A, 616B. Once the user has done so, the entered drug name or concentration is also displayed on the LCD 624 found on the module 616A, 616B. The user must then read the drug name or concentration displayed on that module 616A, 616B, verify that it indeed reflects the drug to be infused by that module as entered on the main display 624, and then must depress the module button 626 to enable the infusion regimen.

This embodiment therefore provides an expandable, adaptable system of pumps which can be customized according to the need of the application. Further, replacement of a defective pump is facilitated.

Figure 4:
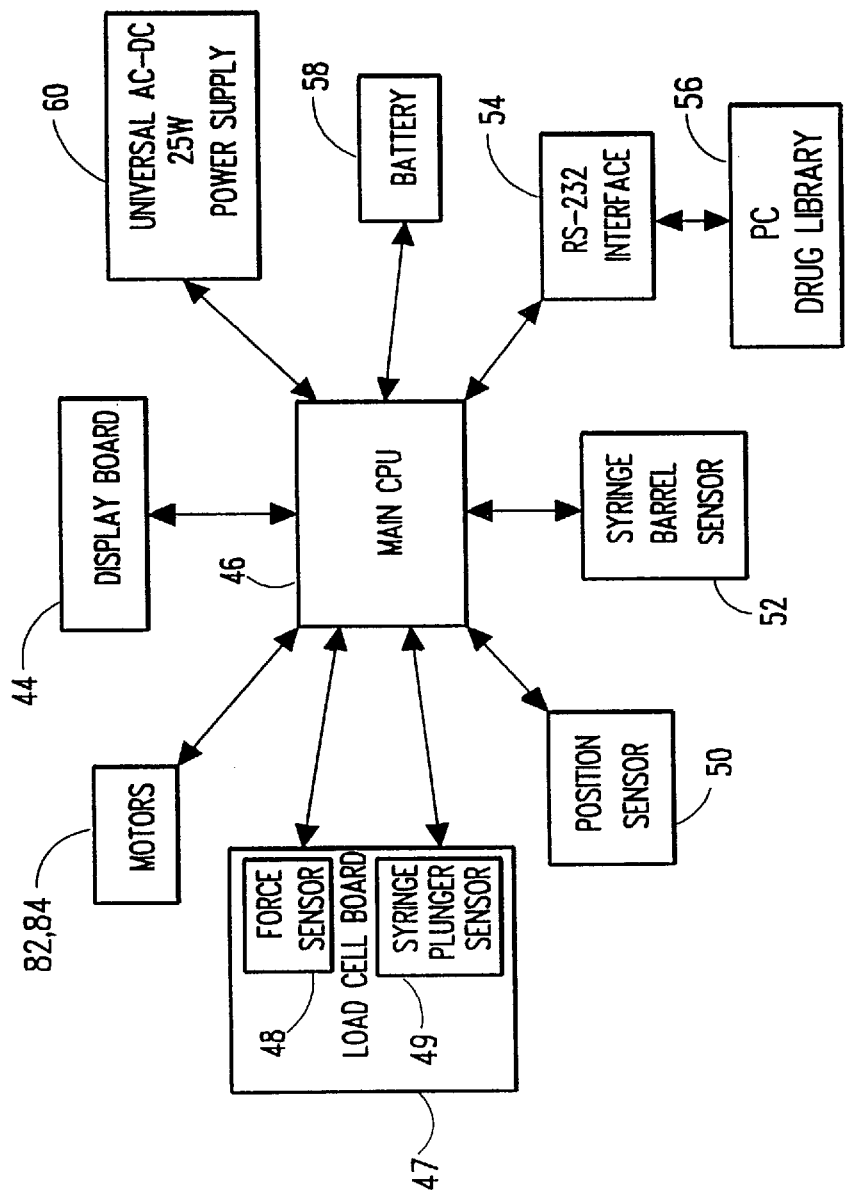
FIG. 4 is a block diagram of the system level electronics for the pumping system of FIG. 1.
Figure 5:
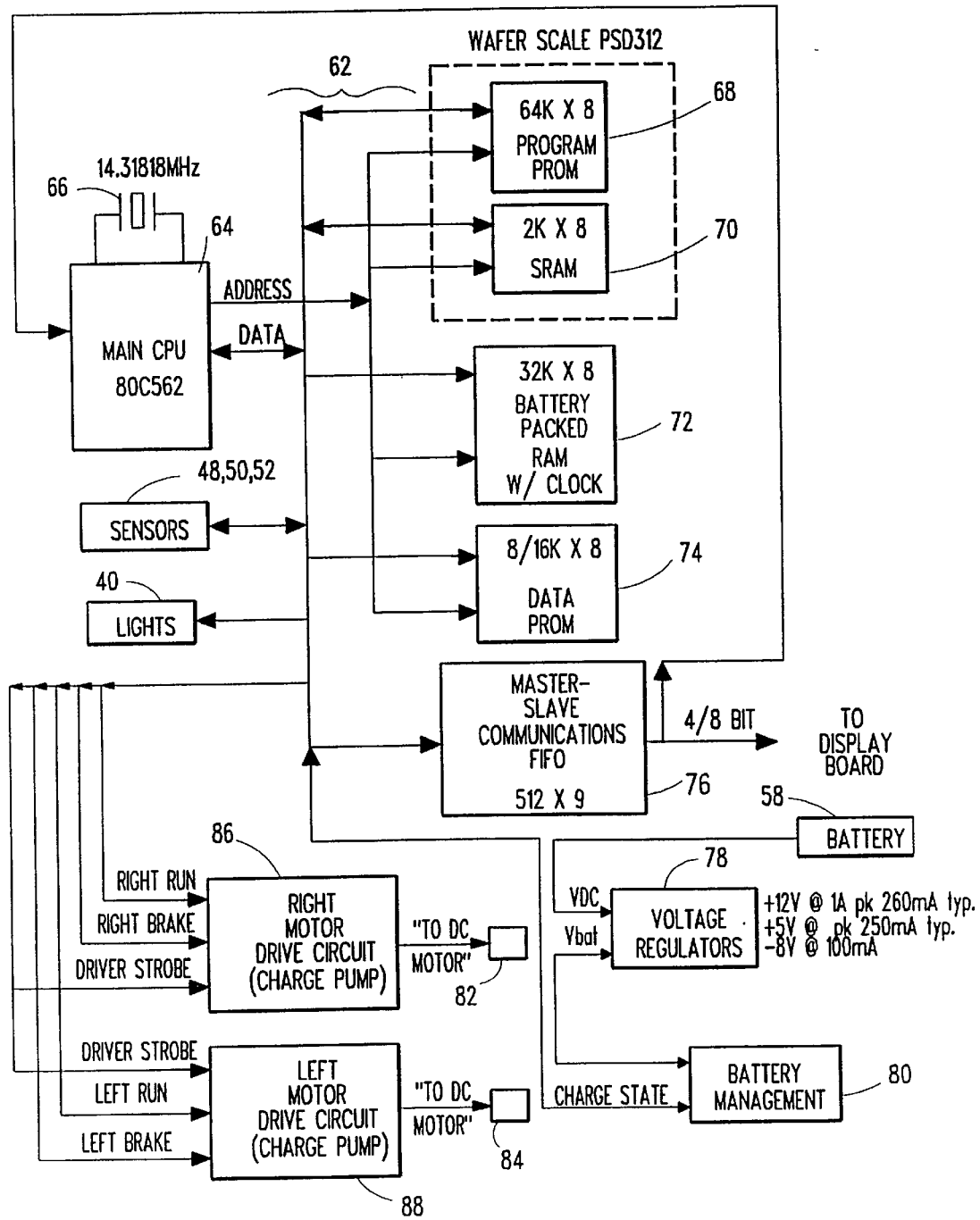
FIG. 5 is a component level diagram for the main processor apparatus of the block diagram of FIG. 1.
Figure 6:
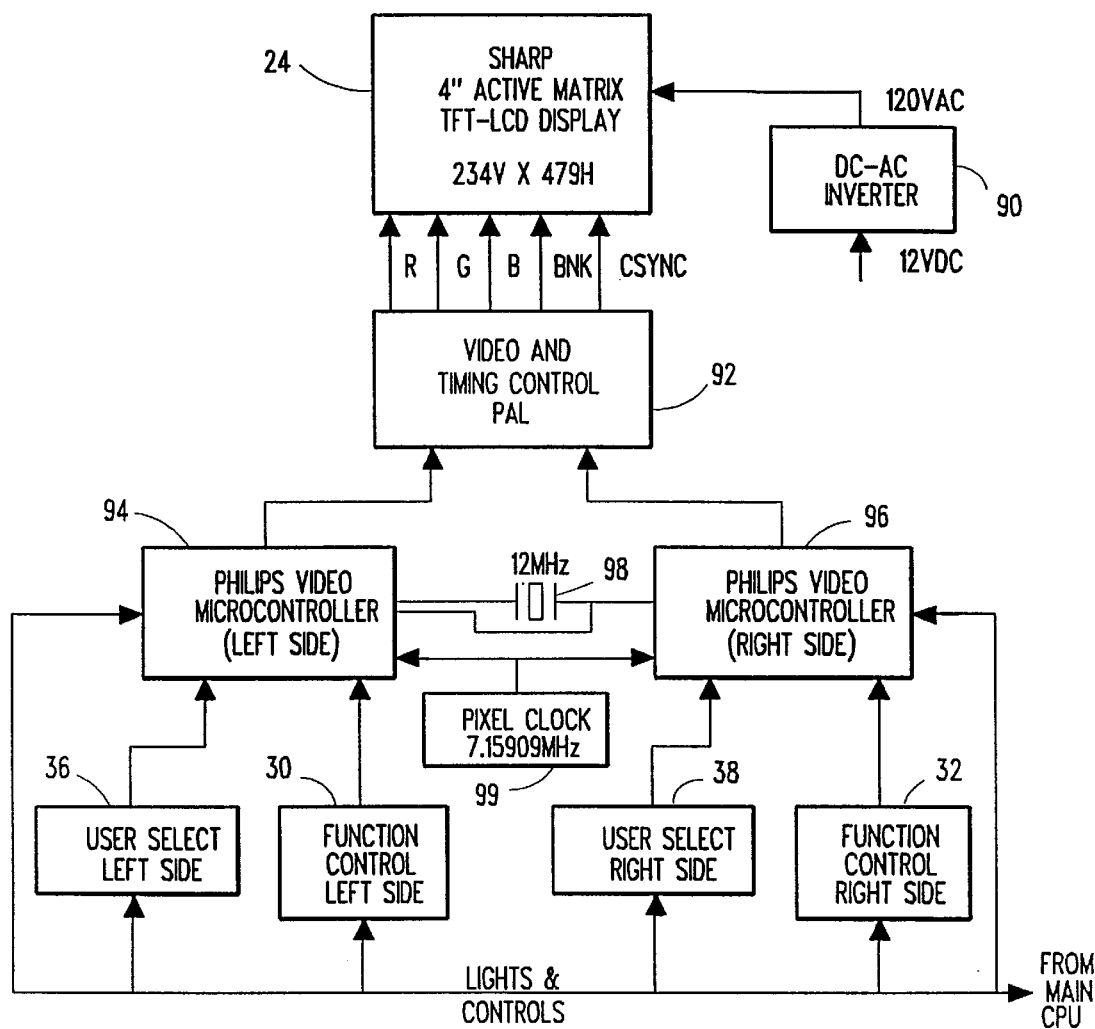
FIG. 6 is a component level diagram of the display electronics for the system block diagram of FIG. 1.

With reference now to FIG. 4, there is shown a general block diagram of the control unit 12 of the present invention which is divided into two main boards, a display board 44 having a processor for each display, and a main CPU board 46, respectively shown in FIGS. 6 and 5. The main CPU board 46 communicates with a force sensor 48 via a load cell board 47 which has a load cell position to sense the pressure applied to the plunger flange as described below. A position sensor 50 is associated with each syringe holding station 16 in order to sense the position of the plunger and therefore the amount of fluid left in the syringe to be pumped. At certain intervals, a warning is provided which indicates how much longer the present syringe can be pumped. This warning is based on a known current volume of the syringe and the rate of infusion, not based solely upon the plunger position. Thus, a more detailed, useful and accurate indication of infusion time remaining is provided.

A syringe plunger sensor 49 is also in communication with the main CPU 46 via the load cell board 47. This sensor 49, as will be discussed in detail below, provides an indication of whether a syringe plunger flange has been positively engaged by the pusher assembly 22. If not, the infusion is inhibited until an indication of engagement is returned from the plunger sensor 49.

A syringe barrel sensor 52 associated with each syringe barrel clamp 18 senses the presence of a syringe and its size. A detailed description of the placement of the position sensor 50, the syringe plunger sensor 49, and the syringe barrel sensor 52 will be given subsequently.

An RS-232, or other, data interface 54 is provided for bidirectional communication to a variety of input or output devices including a PC computer 56 or patient monitor or workstation which can provide remote control or monitoring of the pump, or library information for download into memory associated with the CPU board 46 as shown in FIG. 4. The CPU board is also in communication with the left and right syringe plunger drive motors 82, 84, as discussed further with respect to FIG. 5.

There are three power sources capable of powering the pump. A battery 58 and an international line AC power supply are housed within the pump chassis. The device is also equipped to handle a DC source at the RS-232 connector. The battery 58 provides operating power to the entire system through the main CPU board 46 and alternatively a battery replacing power supply 60 operates from the AC household current or a DC source.

Figure 14:
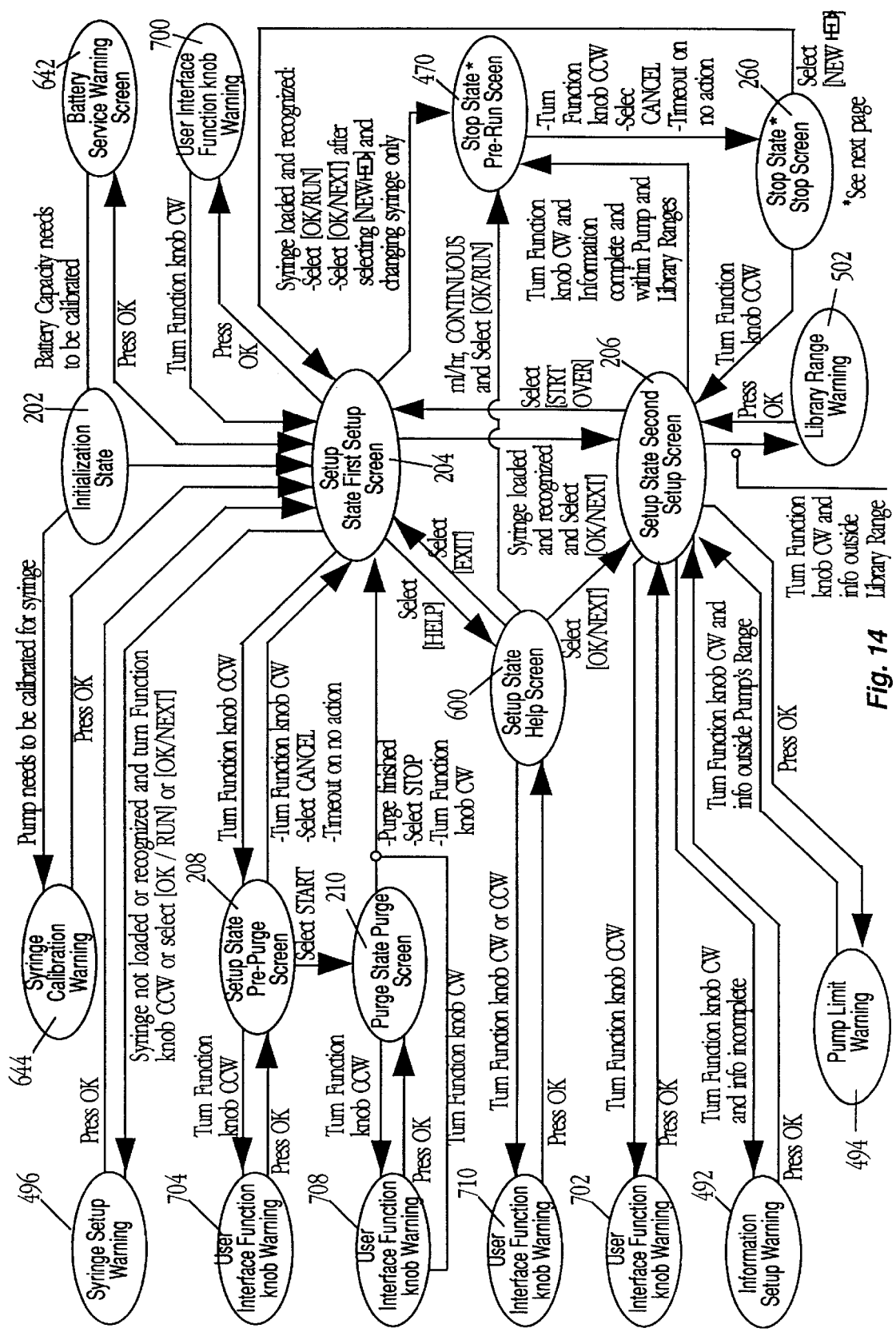
FIG. 14 is a flow chart depicting state relationships in a pump according to the present invention.
Figure 15:
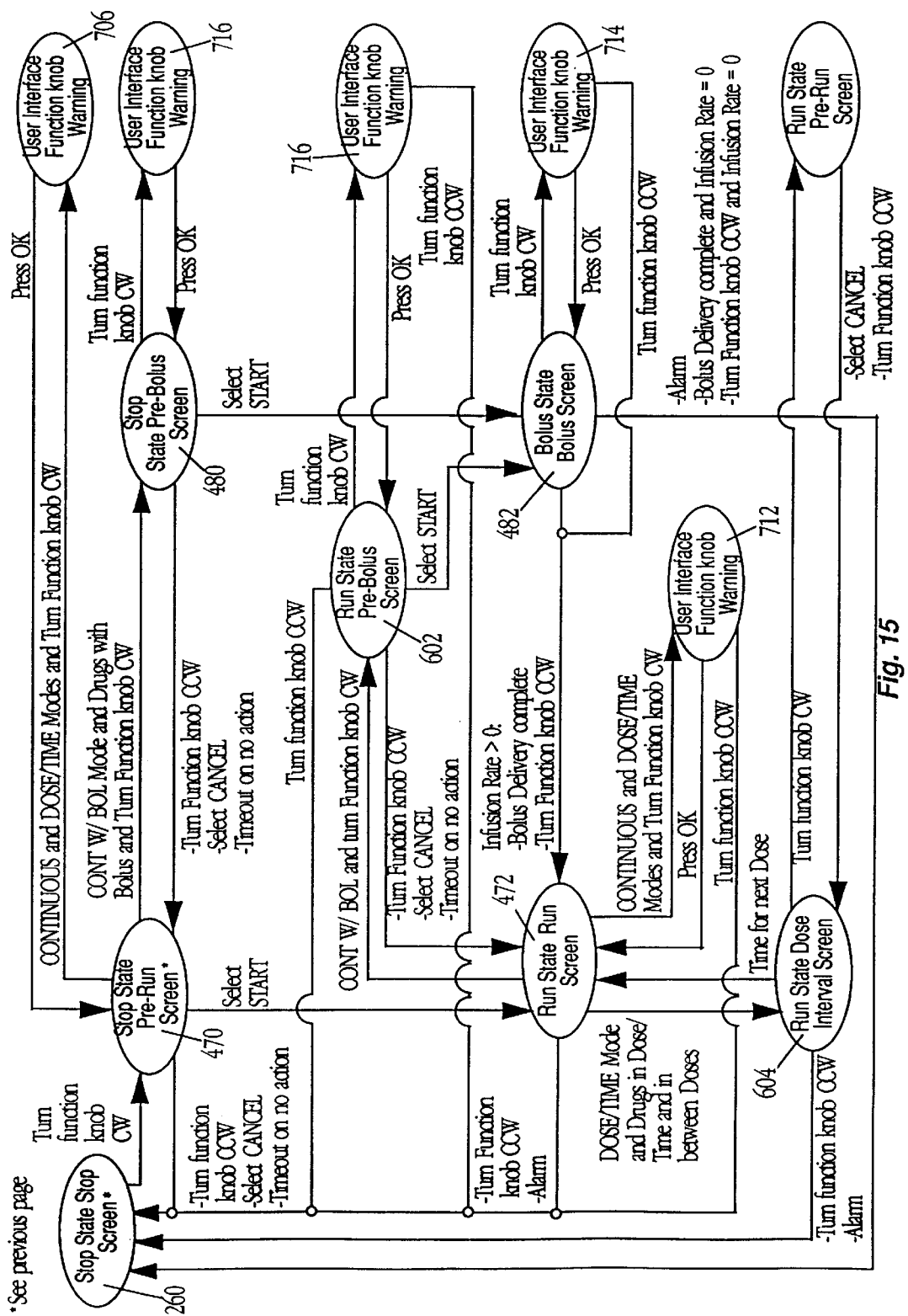
FIG. 15 is a flow chart depicting further state relationships in the pump of FIG. 14.

The main CPU board 46 is illustrated in FIG. 5 and includes a data bus 62 for data and address information communicated by a central processor 64, typically of a model 80C562 derivative, having a clock controlled by a crystal oscillator 66 on the data and address bus 62 is a program PROM 68 which typically contains system programming, such as illustrated in FIGS. 14 et. seq. A SRAM 70 (static random access memory) is also provided for holding specific additional data. A battery backed random access memory 72 is provided on the data bus 62 to hold operating information such as regimen setup data for individual syringe infusions. A data PROM 74 is provided to access such information as any language or country specific data including syringe information. Drop-in upgrades and customization are enabled by use of this data PROM 74. A communications FIFO (first-in-first-out device) queue 76 is provided to communicate with a display board 44 shown in FIG. 6.

The battery 58 applies DC current through a voltage regulator 78 for system power to a battery management circuit 80 which, for example, provides remaining battery life, and charge determinations that are provided to the CPU 64 over the bus 62. When on battery power, a battery icon is displayed with battery life in hours and minutes.

First and second motors, for the embodiment of a two syringe pump as illustrated in FIG. 1, are provided as DC motors 82 and 84. These are driven by common and respective right and left motor drive specific circuits 86, 88. Safe operation is achieved by drive circuits 86, 88 including a charge pump driver, an integrated processor PWM (pulse width modulator) and MOSFET controlling run/brake and strobe controls from the processor port 62 set up by the processor 64 and the software control described below. The charge pump driver circuits 86 and 88 provide quantum power to each DC motor 82 and 84. Because motor rotation requires continuous charge pumping, the potential for a failure mode in which the motors 82 or 84 could free run, such as by short circuiting of a transistor in the drive circuitry, is minimized or eliminated.

As illustrated in FIG. 6, a display board provides driving signals and power to the backlit and active matrix TFT LCD display 24. This includes an AC voltage excitation from an electrical inverter 90 driven by 12 volts DC from the system power source through the voltage regulator 78. The display 24 can provide as an input the composite of the two video processors: red, green, blue and synchronization signals. Colors used to indicate normal running conditions are green. Red type on yellow background is used for warnings, and yellow type on a red background is used for alarms. Other colors may be used as appropriate. In an alternative embodiment, the display can be a monochrome LCD display, with emphasized messages or data being provided in reverse video or via flashing characters or segments.

A display driver 92 in the form of a video and timing control PAL is provided and receives separate inputs, corresponding to the separate display portions 26, 28, from respective separate processors 94, 96 for each display portion, thereby providing through a single display essentially multi-syringe user interfacing. It is again noted that the present disclosure describes a two-syringe embodiment only for illustrative purposes. More than two syringes can be controlled and pumped using the present concept.

A crystal 98 and a pixel clock 99 time and synchronize the operations of the processors 94, 96. The data entry knobs 30, 32 as well as the function knobs 36, 38 drive the processors 94, 96 respectively to control the display information and to generate selection data for use by the CPU 64. Under software control, CPU 64 in turn controls the lights 40. The CPU 64 also controls a set of lights 41 which provide an indication of pump status independent of the display 24.

Figure 7:
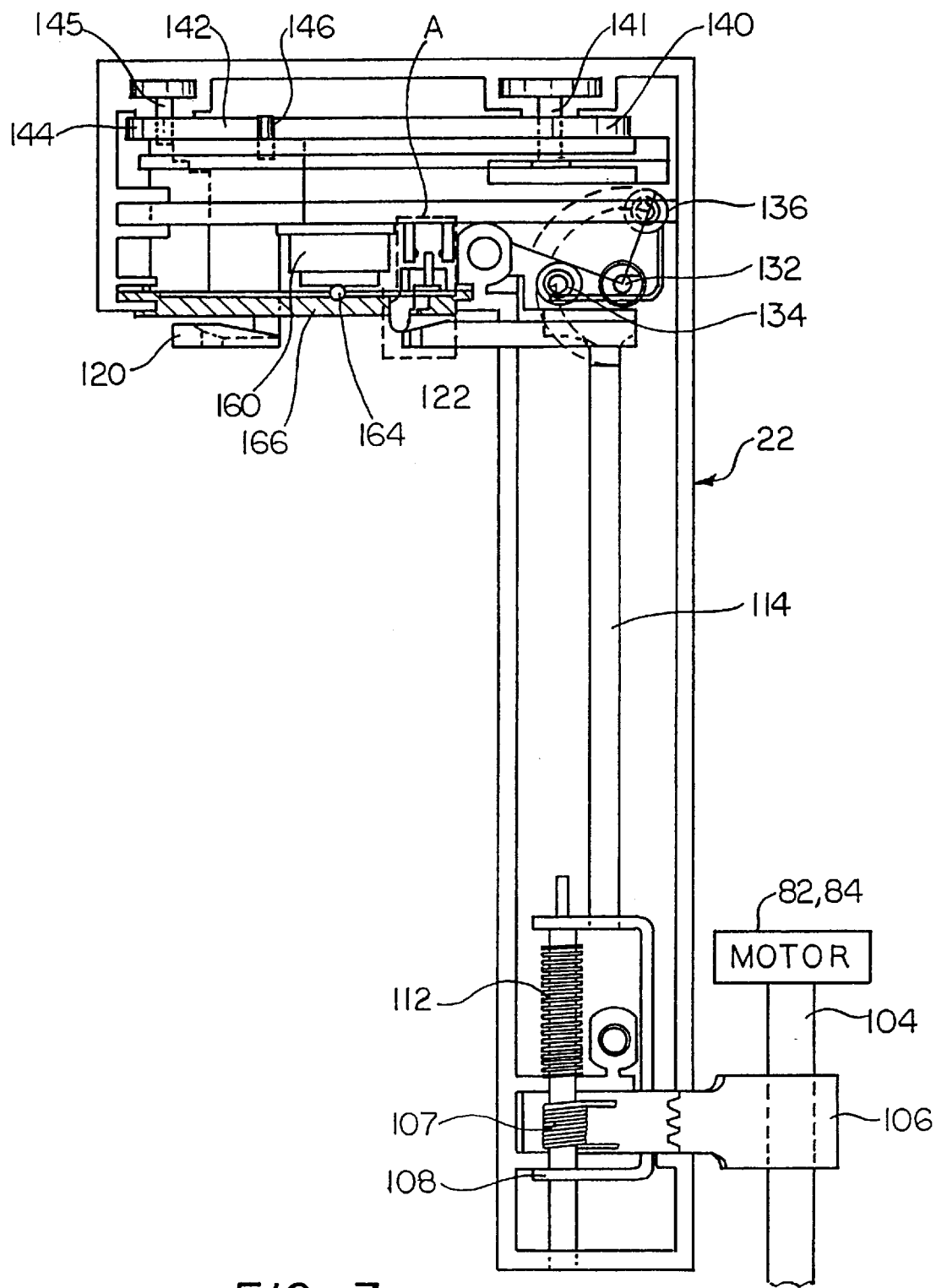
FIG. 7 is a mechanical diagram of a syringe pusher assembly for controlled plunger driving.
Figure 8:
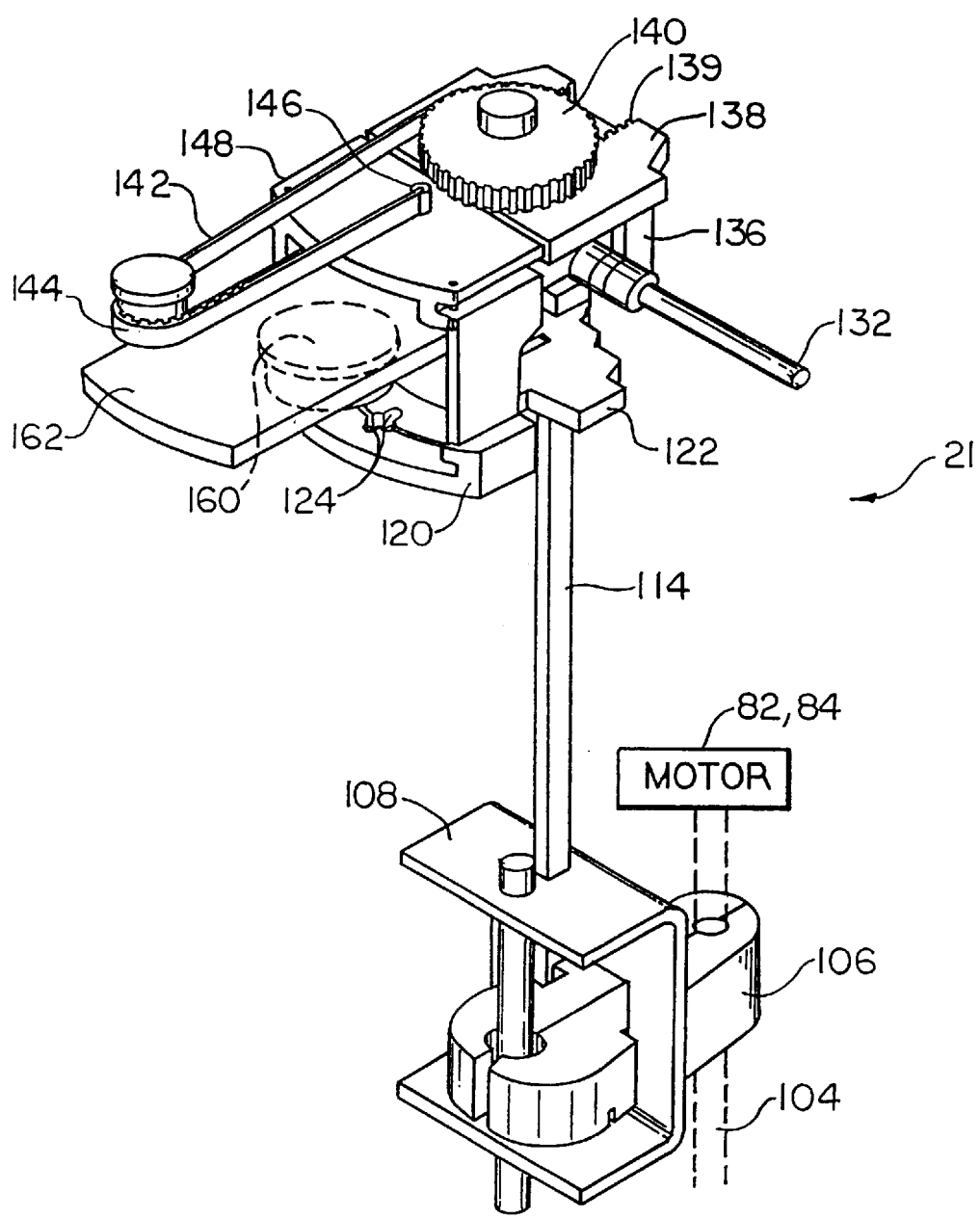
FIG. 8 is a view of a portion of the components of the FIG. 7 mechanics.
Figure 9:
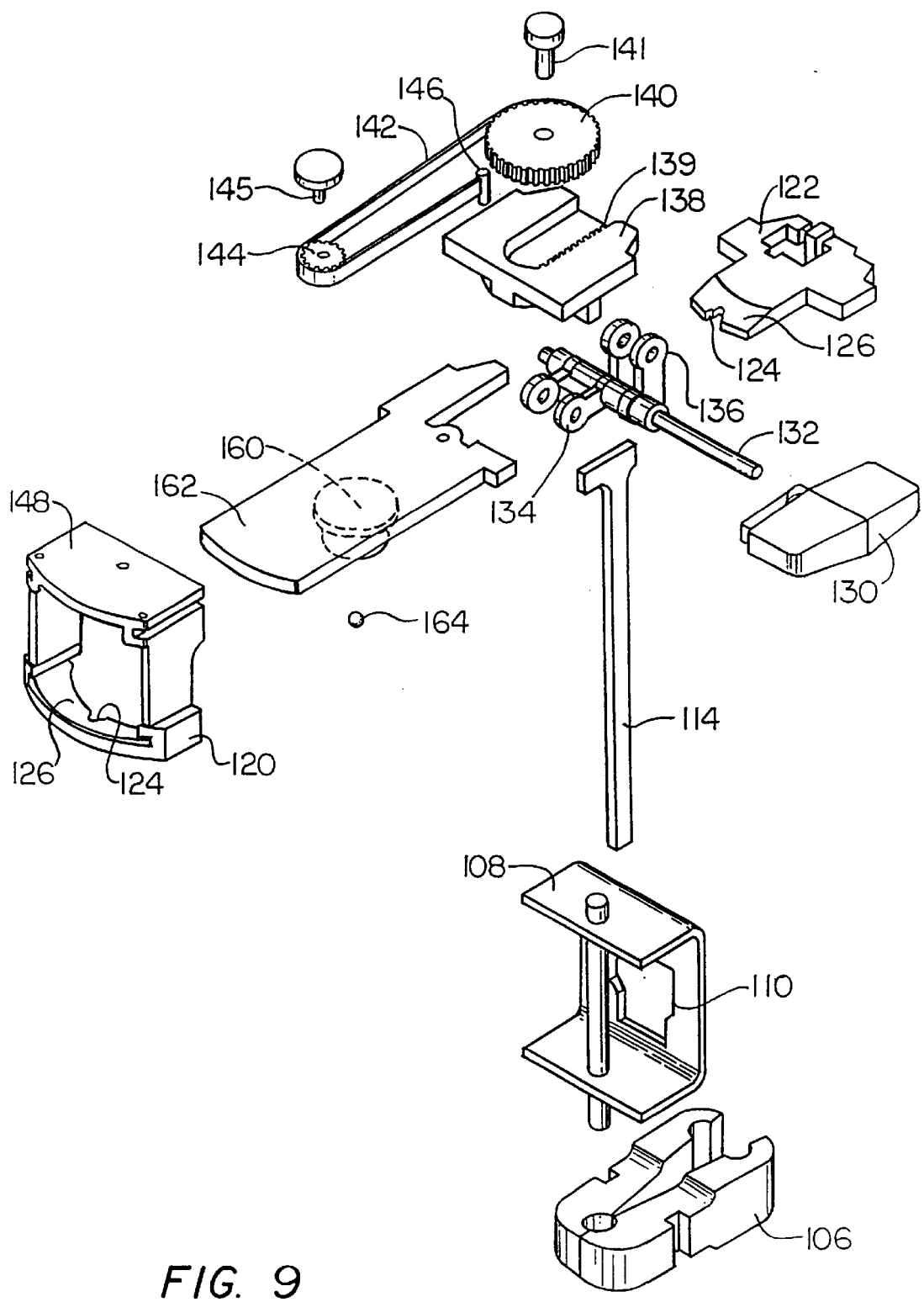
FIG. 9 is an exploded component diagram of the components of FIGS. 7 and 8.

With respect now to FIGS. 7, 8 and 9, the mechanics of each of the syringe docking and holding stations 16 is illustrated in mechanical details. As shown in each docking station in FIG. 7, the pusher assembly 22 is driven by a threaded lead screw 104 which passes through (shown in phantom) a split nut 106 held in a lock plate 108. Portions of the split nut 106 held against the lead screw 104 are cooperatively threaded. The lock plate 108 has on a side portion a bevel cut aperture 110 in which the two halves of the split nut 106 are forced together by the lock plate aperture 110 when the lock plate is in an upward position relative to the split nut 106. The two halves of the split nut 106 tend to spread apart under the urging of a torsion spring 107 attached to each of the two halves. Thus, the bevel aperture 110 with the lock plate 108 in the upward position forces threaded halves of the split nut 106 securely around the lead screw 104.

The lead screw 104 is driven by a motor 82, 84, as shown in both FIGS. 7 and 8. In the latter, the lead screw 104 is shown in phantom, and the motor 82, 84 is shown schematically. When driven in an infusion mode, the lead screw forces a pusher assembly 22 via the lead screw 104 down thereby depressing the syringe plunger 17 and forcing the infusion of fluid from the syringe. The split nut 106 is opened by forcing the lock plate 108 down under a control link 114 by a mechanism, to be described below, including a rotatable actuation lever or pad 130 associated with the pusher assembly 22 thereby forcing the lock plate 108 downward and allowing the split nut 106 to slide open by the torsion spring 107 with relatively little force. Upon release of the actuation lever 130 and retraction of linkage 114, allowing the split nut 106 to return to the clamp position by a spring 112 pushing the lock plate 108 upward, the syringe plunger flange is securely held within the pusher assembly 22 as described below.

As illustrated more fully in FIGS. 8 and 9, the plunger is held in position by front and rear plunger clamps 120, 122 having respective notches 124 for holding the syringe plunger 17 with the plunger flange positioned thereabove on bevelled surfaces 126 associated with each plunger clamp 120, 122. The separation of the plunger clamps 120 and 122 is provided by the actuation lever 130 which rotates a shaft 132 which in turn rotates a set of lever arms 134 having a central rod therethrough (not shown for clarity) which bears upon an upper end of the control link 114 at the end of a rotation. The lock plate 108 is forced down as a result.

Another set of lever arms 136 (and a shaft extending therebetween, not shown) moves a drive plate 138 forward. Teeth 139 formed in the drive plate 138 cause a first compound pulley 140 to rotate about first pulley shaft 141. The first compound pulley 140 has a smaller, lower gear (not shown) which is rotated by the motion of the drive plate 138. This rotation similarly rotates the upper gear of the first compound pulley 140, visible in FIGS. 8 and 9. Clockwise rotation of the first pulley 140 winds a band 142 about the first pulley 140. This band 142 is pulled past a second pulley 144 pinned by a second pulley pin 145, thus pulling forward an upper surface 148 of the front plunger clamp 120 connected by a pin 146 to the end of the band 142.

A load cell 160 is held beneath load cell plate 162. The load cell 160 receives force from the plunger flange through a ball bearing 164 which rides between the load cell 160 and a force receiving plate 166. The plunger flange fits in between the plunger clamps 120, 122 and the force receiving plate 166 in such manner as to provide a balanced force on the load cell 160 independent of syringe size. A spring (not shown) extends between the front plunger clamp 120 and the drive plate 138 so that upon release of the actuation pad 130, the front and rear plunger clamps 120, 122 are drawn toward each other, securing the plunger flange therebetween.

Upon complete rotation of the actuation lever 130, the lever arms 136 and shaft extending therebetween bear against the linkage 114 pushing the lock plate 108 down and forcing the bevel cut aperture 110 to push downward against spring 112 and allowing the split nut 106 to move open at the lead screw into the larger aperture region where it separates under the spring resilience of the torsion spring 107. This allows the lead screw 104 to slide, permitting positioning of the plunger clamps 120, 122 about the plunger flange with the syringe barrel in the barrel clamp 100. The syringe barrel 20 is secured therein when the barrel clamp is released by paddle 19, as described below.

Because of the manner in which the clamps 120, 122 open to accommodate plunger positions for a wide variety of syringe sizes, the system can accommodate syringes typically in the range of 1–60 cc, automatically.

Figure 10:
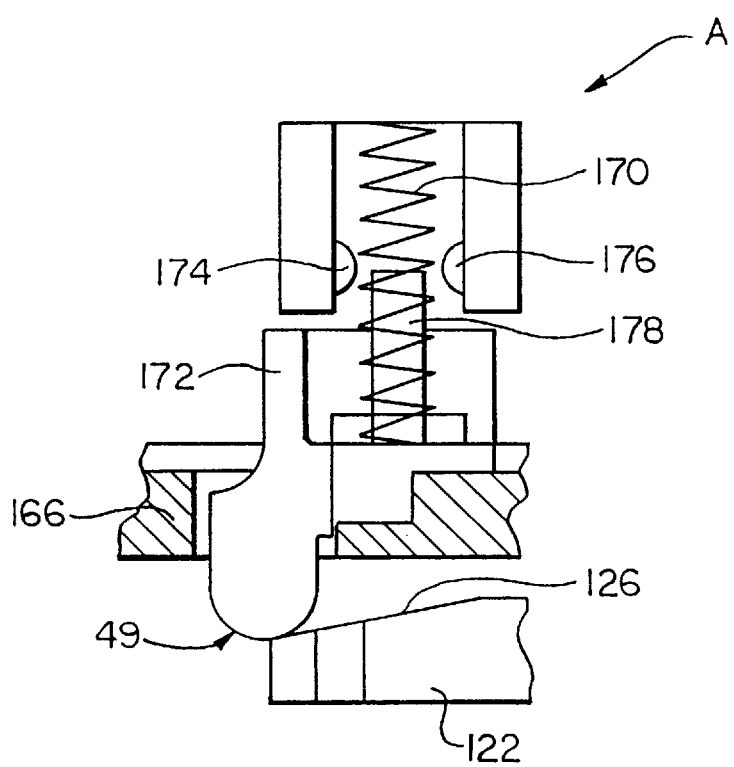
FIG. 10 is a detailed view of components of the pusher assembly of FIG. 7.
Figure 11:
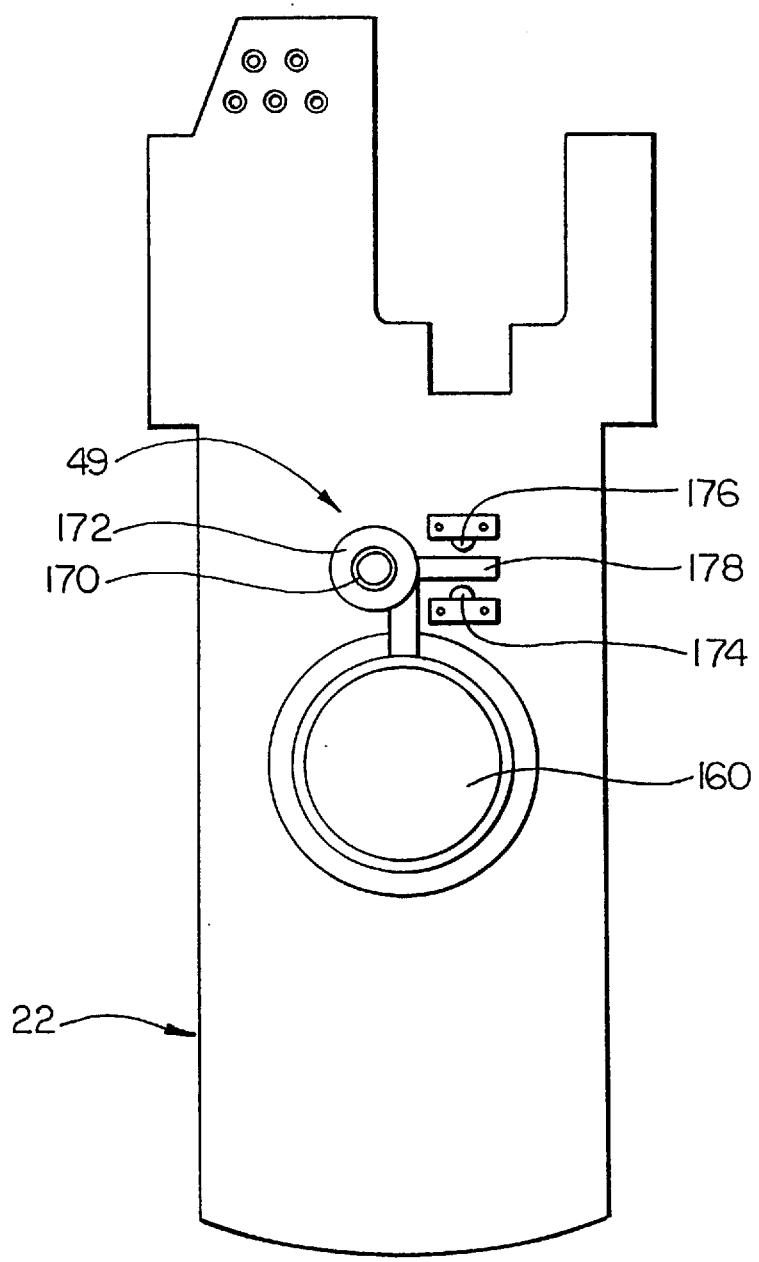
FIG. 11 is a top view of the pusher assembly of FIG. 7.

As noted above, a syringe plunger sensor 49, shown in FIG. 10 as detail A from FIG. 7 and as shown in FIG. 11, provides an indication of proper syringe installation within the pusher assembly 22. A spring 170 acts against an LED block 172, driving the block 172 downward toward the underlying rear plunger clamp 122. An LED source 174 and optical sensor 176 are positioned such that a light blocking portion 178 is capable of passing therebetween. In the view illustrated in FIG. 10, the light blocking portion 178 and the LED source and sensor 174, 176 are in front of the spring 170. Once a plunger flange is in place between the front and rear plunger clamps 120, 122 and against the force receiving plate 166, the LED block 172 is driven upward and the light blocking portion 178 interrupts the receipt of light at the LED sensor 176 from the LED source 174.

Figure 12:
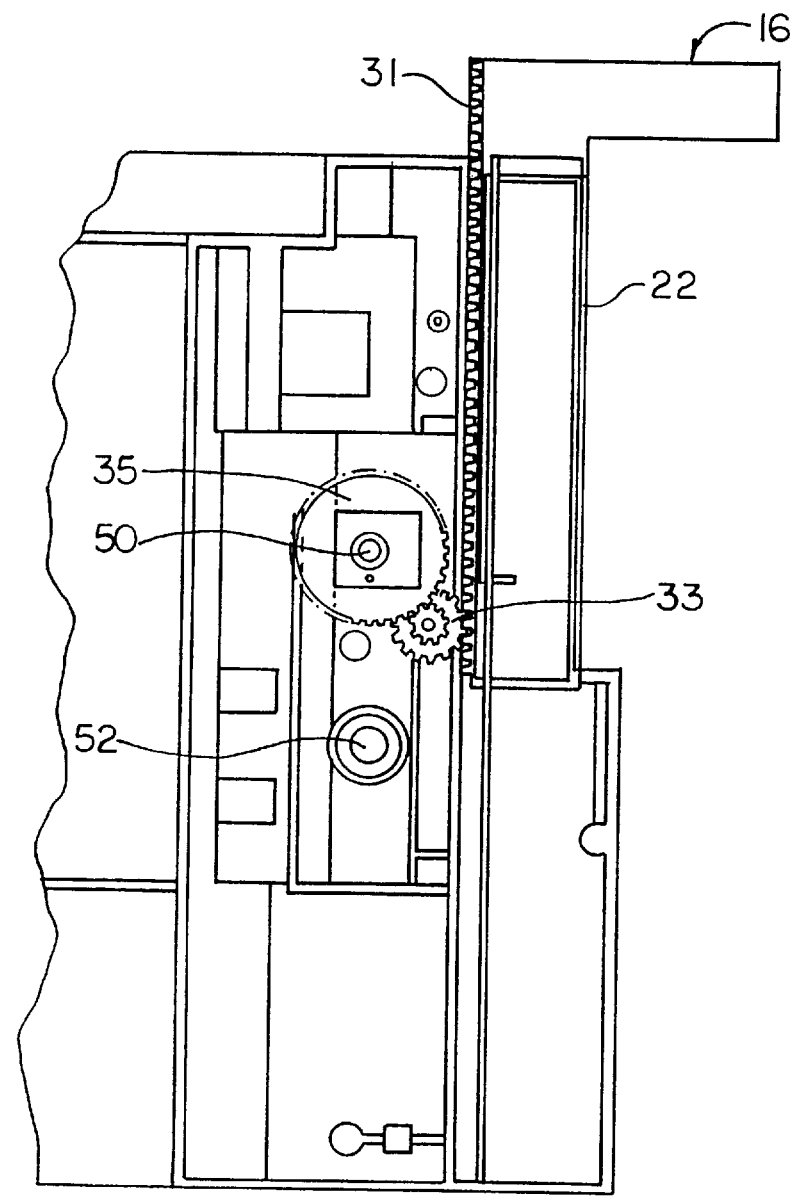
FIG. 12 is a cutaway view of the pump of FIG. 1 showing sensor displacement.

The placement of the position sensor 50 with respect to the pusher assembly 22 is discussed with respect to FIG. 12 in which a cut-away side view of a syringe docking or holding station 16 of the pump of FIG. 1 is illustrated. Each pusher assembly 22 has on a back side a row of teeth 31 extending the height of the pusher assembly 22. These teeth 31 cooperate with an idler gear 33, which in turn cooperates with a position sensor gear 35. This position sensor gear 35 is axially attached to the position sensor 50. Thus, as the pusher assembly 22 travels, the position sensor 50 enables the control unit 12 to determine how much material remains to be infused based on the known size of the installed syringe.

Figure 13:
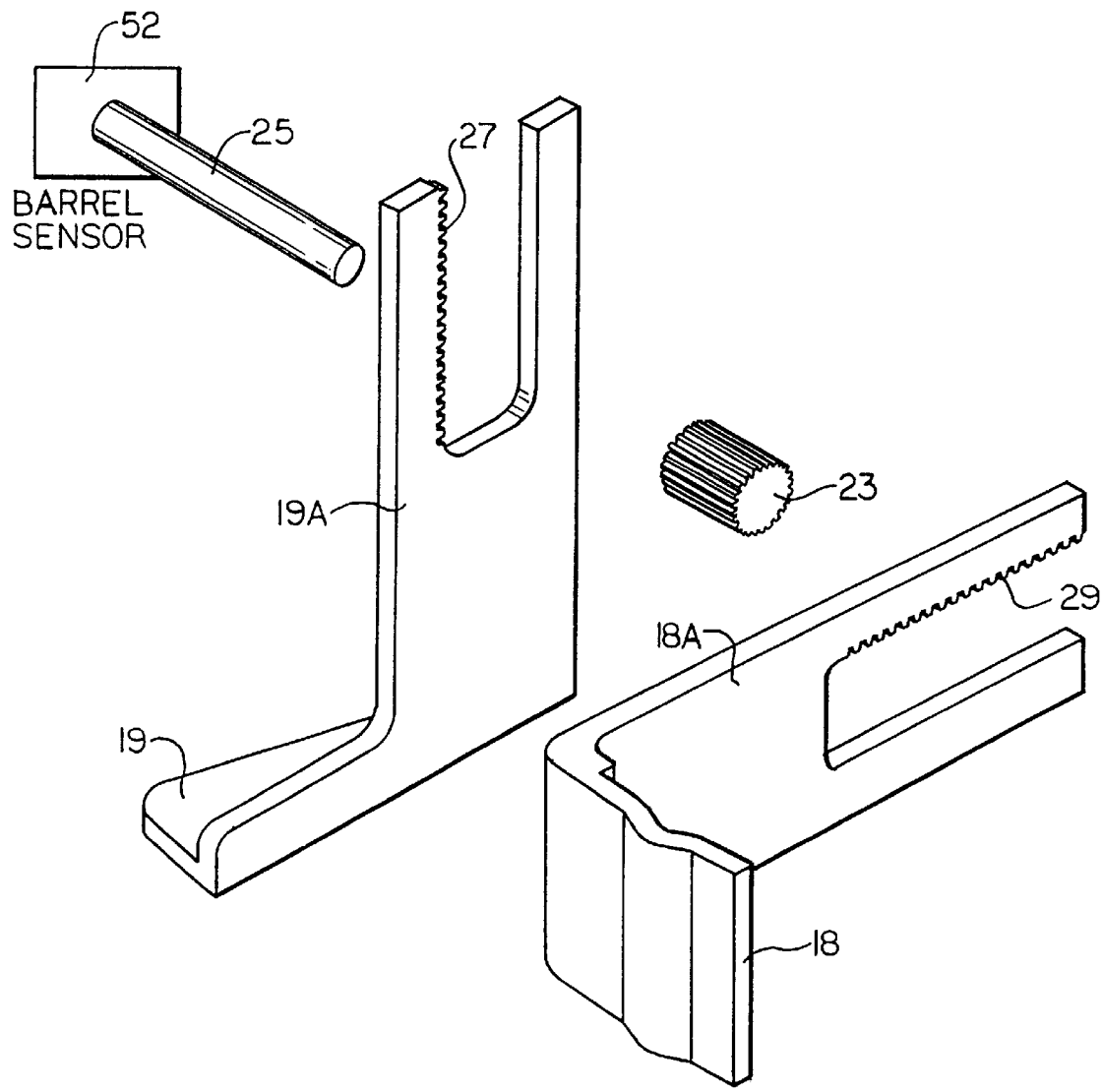
FIG. 13 is a perspective view of syringe barrel clamp components of the pump of FIG. 1.

Also shown in FIG. 12 and in FIG. 13 is the syringe barrel sensor 52. As previously noted, a user presses down on the paddle 19 to install a syringe into the syringe barrel clamp 18. This is achieved in the illustrated embodiment by rotation of a paddle gear 23 cooperating with teeth 27 disposed on a paddle extension 19A. A spring (not shown) connects an upper end of the paddle extension 19A to the pump frame, thus urging the paddle upward. The paddle gear 23 further cooperates with teeth 29 disposed in a barrel clamp extension 18A. Thus, as the paddle is pulled downward, the paddle extension teeth 27 rotate the paddle gear 23, which is mounted on a barrel sensor shaft 25. Rotation of the paddle gear 23 causes the barrel clamp extension 18A and the barrel clamp 18 to extend out away from the pump and simultaneously causes the barrel sensor 52 to register the movement. Release of the paddle 19 allows the spring to contract, and draws the barrel clamp 18 to draw inward against the installed syringe. If this sensor 52 is properly calibrated, the distance from the pump the barrel clamp 18 must be to hold a syringe provides an indication of syringe size.

As noted, each of the two pumps within a pump system has five operating states: Purge, Setup, Stop, Run and Bolus. Entry into and exit from each of these states is controlled by manipulation of the respective function knob 36, 38 on the front panel of the pump below the data entry knob 30, 32, and/or pushing a data entry knob to stop one function or start another or by software control upon completion of a certain function. LED's associated with each function knob 36, 38 indicate the current state of the respective pump. Illumination of each of these LED's is controlled by software; transition between operating states is software controlled and thus allows automatic transition between states as well as prevents inadvertent or inappropriate operating state transition.

Each pump has two additional operating states: Power-up and Alarm. Entry into and exit from these states is similarly controlled by software, as recited above. Thus, user manipulation of the function knob has no impact on these states.

The following is a discussion of the various states, the options presented to the user therein, and the possible state transitions available in an illustrative embodiment of the present invention. For the sake of clarity, the names of the various states have been capitalized. The relationships between the pump states are illustrated in the finite state diagrams of FIG. 14 et seq., which should be referred to as one progresses through the following descriptions of each state.

Power-up

Figure 16:
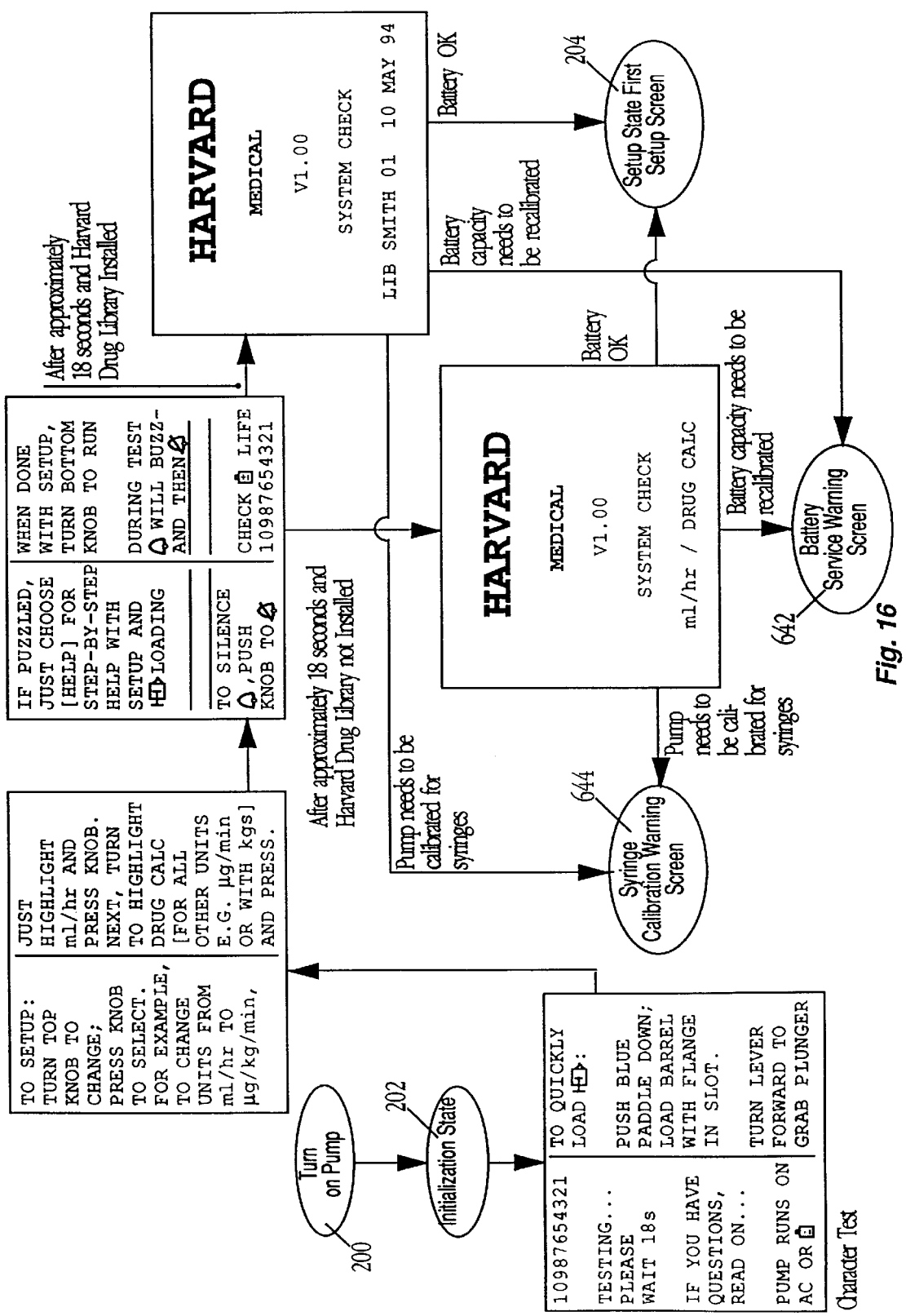
FIG. 16 provides exemplary Initialization state display screens in the pump of FIG. 14.

With reference to FIG. 14 and FIG. 16, when the pump is first turned on 200, initialization software is executed which places the pump in an Initialization State 202, in which tasks such as clearing internal RAM, setting up registers and executing the power-on self-test are performed. A high quality, non-destructive memory test is performed on the entire non-volatile RAM utilizing internal RAM as a scratch pad and without the requirement of a large shadow RAM for temporary data storage. Upon successful completion of this self-test, the initial Setup state screen, also referred to as the First Setup screen, is displayed 204.

Purge

Figure 17:
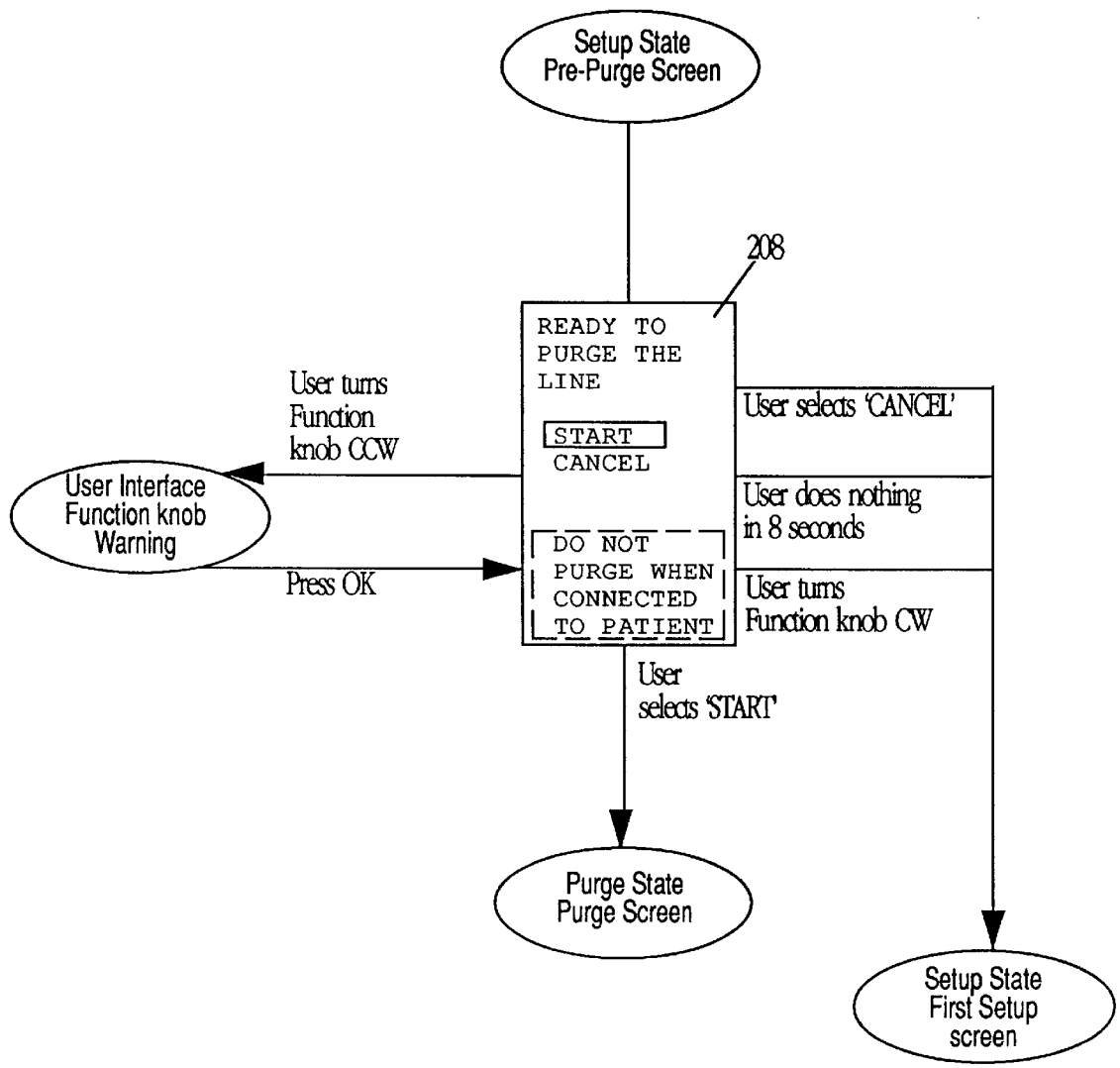
FIG. 17 provides exemplary Setup state Pre-Purge display screens for the pump of FIG. 14.

The Purge state can only be accessed from the Setup state, thus avoiding excitation of purge functions while the pump is connected to a patient. If the pump is in the Setup state with the first Setup screen 204 displayed, the Purge state is accessed by turning the function knob (counterclockwise in the illustrated embodiment) toward the word "Purge". A Setup state Pre-Purge screen is then displayed 208, as illustrated in FIG. 17. In an illustrative embodiment, a message such as "READY TO PURGE THE LINE" is displayed, and "START" and "CANCEL" options are each displayed with "START" highlighted and the warning message "DO NOT PURGE WHEN CONNECTED TO PATIENT" displayed. The "Setup" LED remains lighted.

With further regard to FIG. 17, if a purge of the associated syringe is not desired or if the function knob was inadvertently turned to the Purge function, the user can push the data entry knob when "CANCEL" is highlighted to return to the first Setup screen 204; This allows the user to avoid initiation of an unwanted purge. The user can also turn the function knob clockwise (CW) to return to the first Setup screen 204. As a further safeguard, if the user does not select "START" or "CANCEL" from the Pre-Purge screen 208 after a short period of time, the pump will automatically revert to the first Setup screen 204, and the Setup LED will remain lighted.

Figure 18:
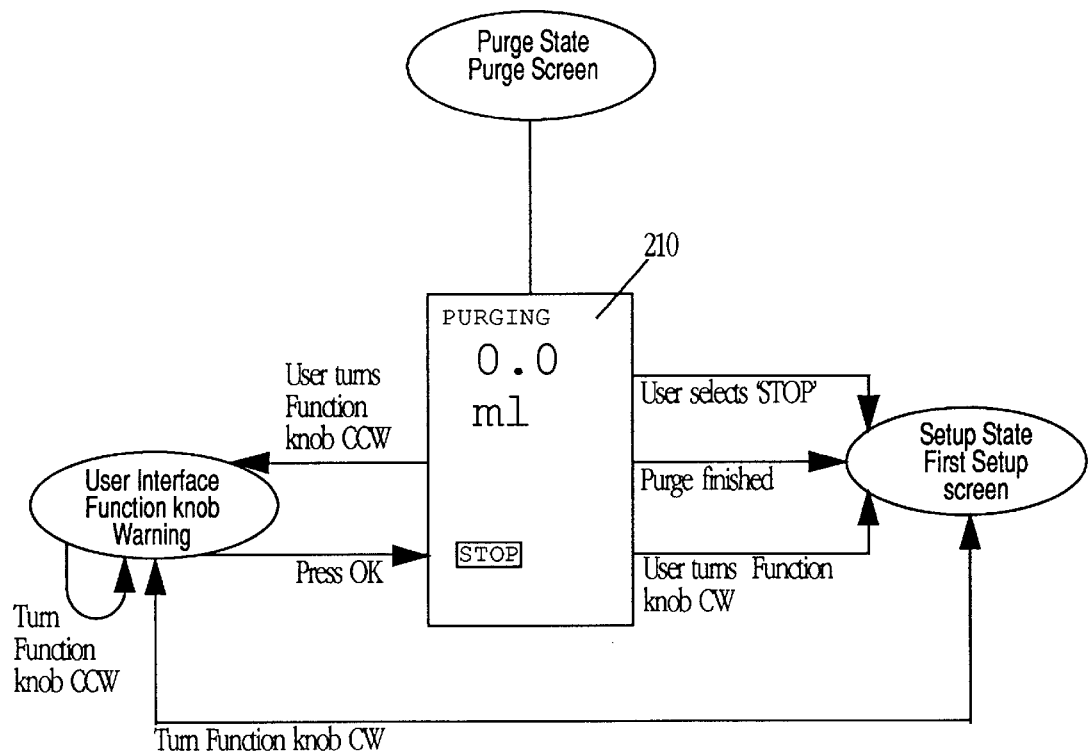
FIG. 18 provides exemplary Purge state Purge display screens for the pump of FIG. 14.

If the Purge state is indeed desired, the user must push the data entry knob to select "START", thus verifying selection of the Purge state and enabling the display of the Purge state screen 210, shown in an illustrative embodiment in FIG. 18. Once the Purge function has been initiated, the Purge screen 210 will indicate the quantity being purged (typically in milliliters (ml)), this number incrementing.

During a purge, the pump will run at a rate dependent on the syringe size (e.g. 360 ml/hr with a 60 cc syringe) until a certain volume is delivered or until the pump is stopped by the user, at which point the pump will return to the first Setup screen 204. A user can also halt the purge prematurely by depressing the data entry knob, thus selecting the word "STOP", which is highlighted. Alternately, the user can turn the function knob CW. In each case, the Setup state is reentered and the first Setup screen is displayed 204.

Setup

The Setup state is used to enter all of the information necessary to run the pump, such as: syringe manufacturer and size; infusion units or type; mode or drug name; concentration; patient weight; infusion rate; bolus amount and duration; and dose amount, dose duration, number of doses and dose interval. Entry of this information is enabled through the use of plural variations on the first and second Setup screens 204, 206. In general, the variations are prompted in conformity with the sequential entry of such information.

In a further embodiment of the pump of the present invention, a Drug Library can be installed in the pump. This Library contains for each entry the following information: type; drug name; default concentration and other selectable concentrations; default infusion rate; minimum and maximum infusion rate limits; default bolus amount and duration; minimum and maximum bolus amount and rate limits; default dose amount, dose duration, number of doses, dose interval; and minimum and maximum dose amount and rate limits. A further discussion of the Drug Library is found below. Such stored information is displayed on the first and second Setup screens to simplify the data entry process.

Access to the Setup state 204 is provided via the Initialization state 202 by turning on the pump 200, by selecting the "STOP" option from the Purge screen 210, or by turning the function knob to light the setup LED. First initiation of the Setup state causes the display of the first Setup screen 204. The setup for the last two infusions, if any, is displayed.

Figure 19:
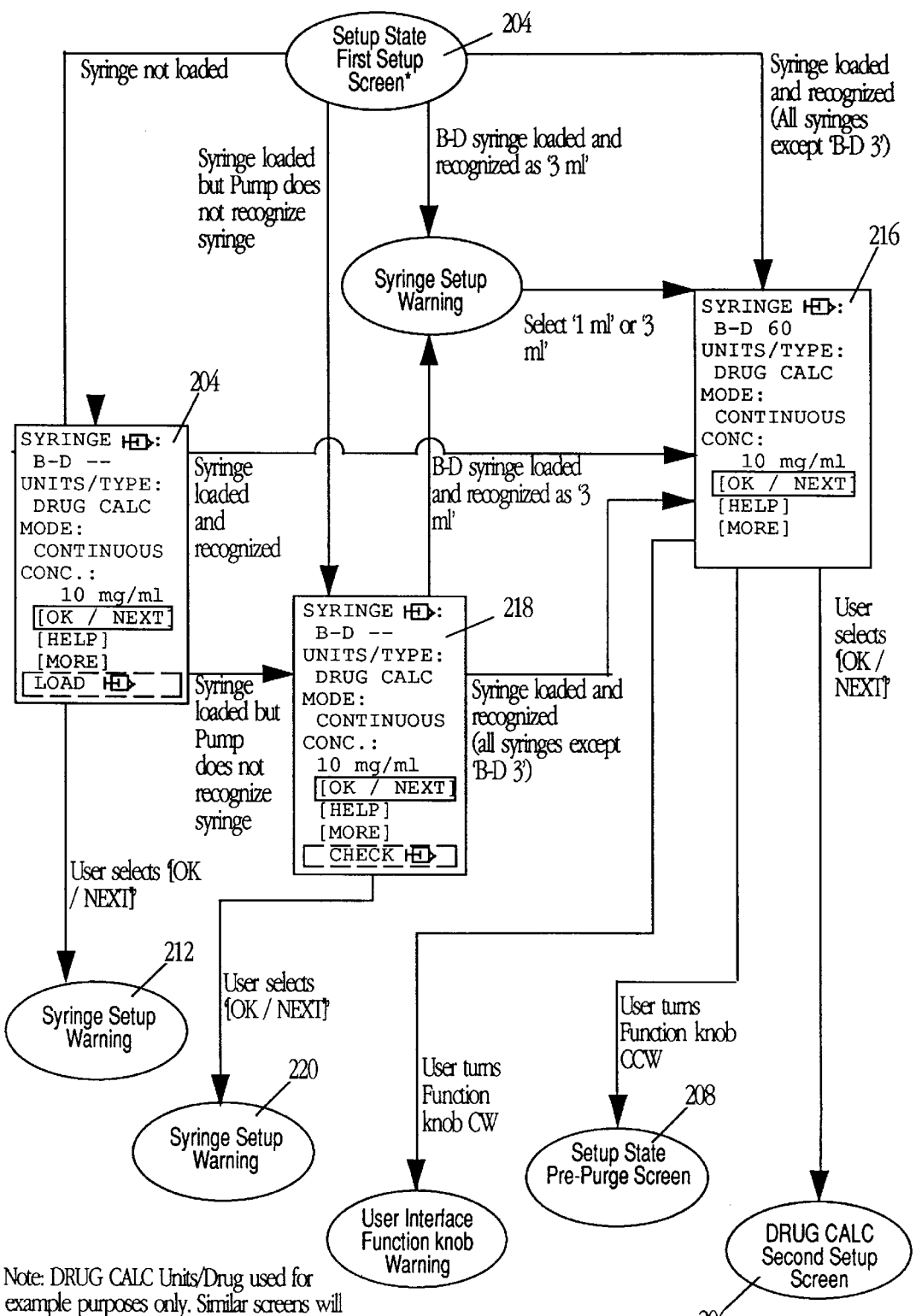
FIG. 19 provides exemplary display screens in a flow chart depicting installation of a syringe in the pump of FIG. 14.
Figure 52:
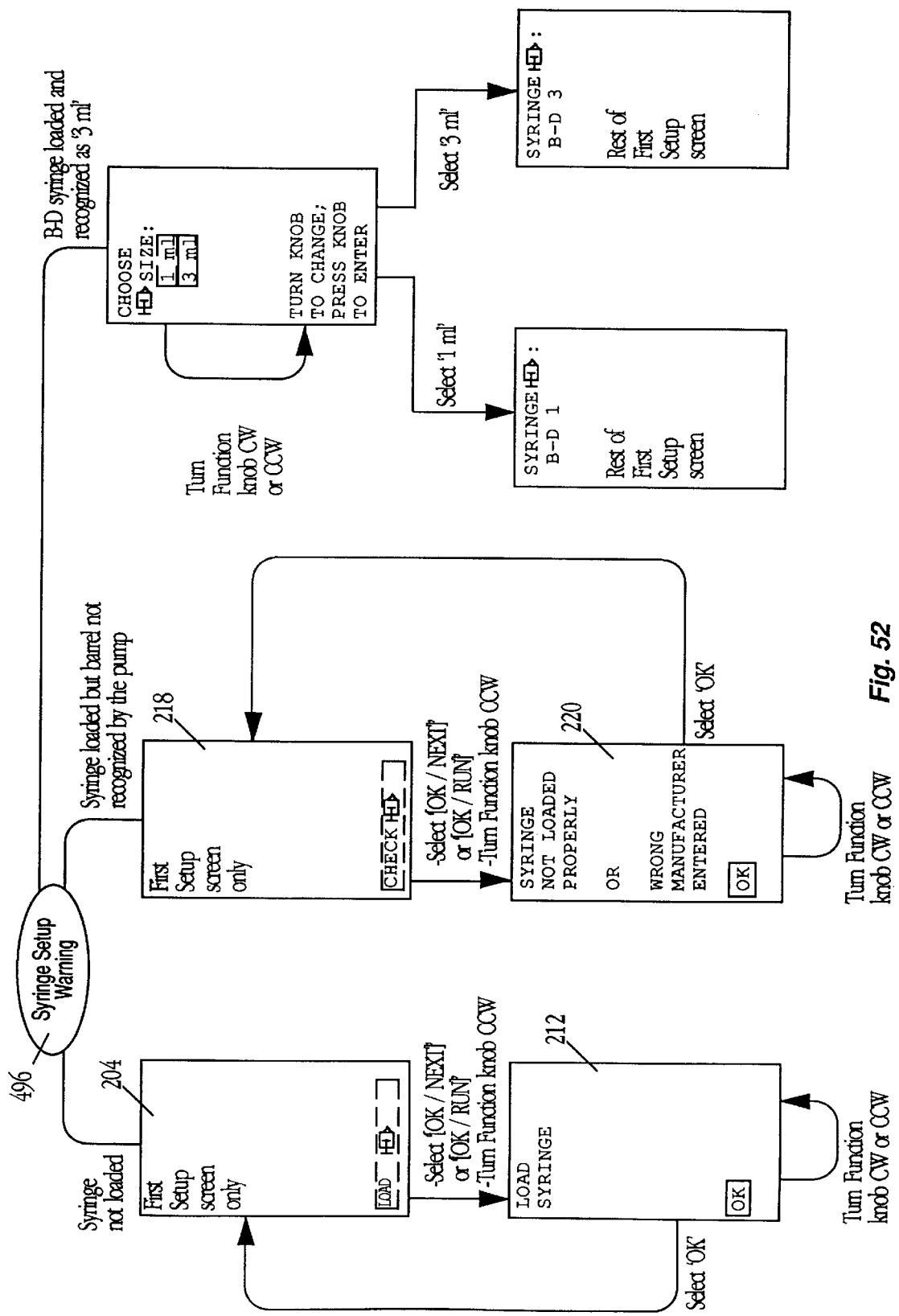
FIGS. 52 through 61 provide exemplary warning screens for the pump of FIG. 14.
Figure 53:
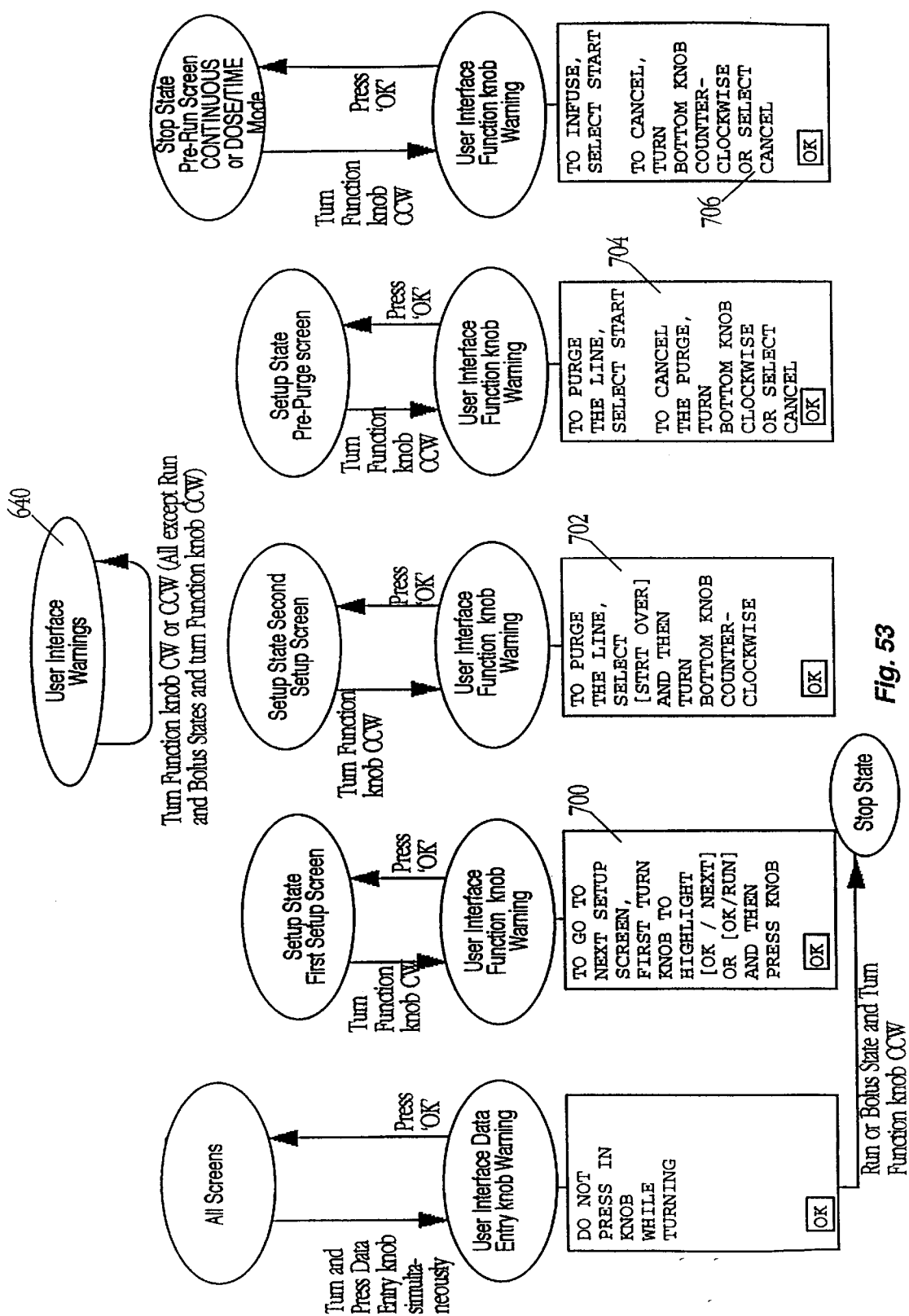
Figure 54:
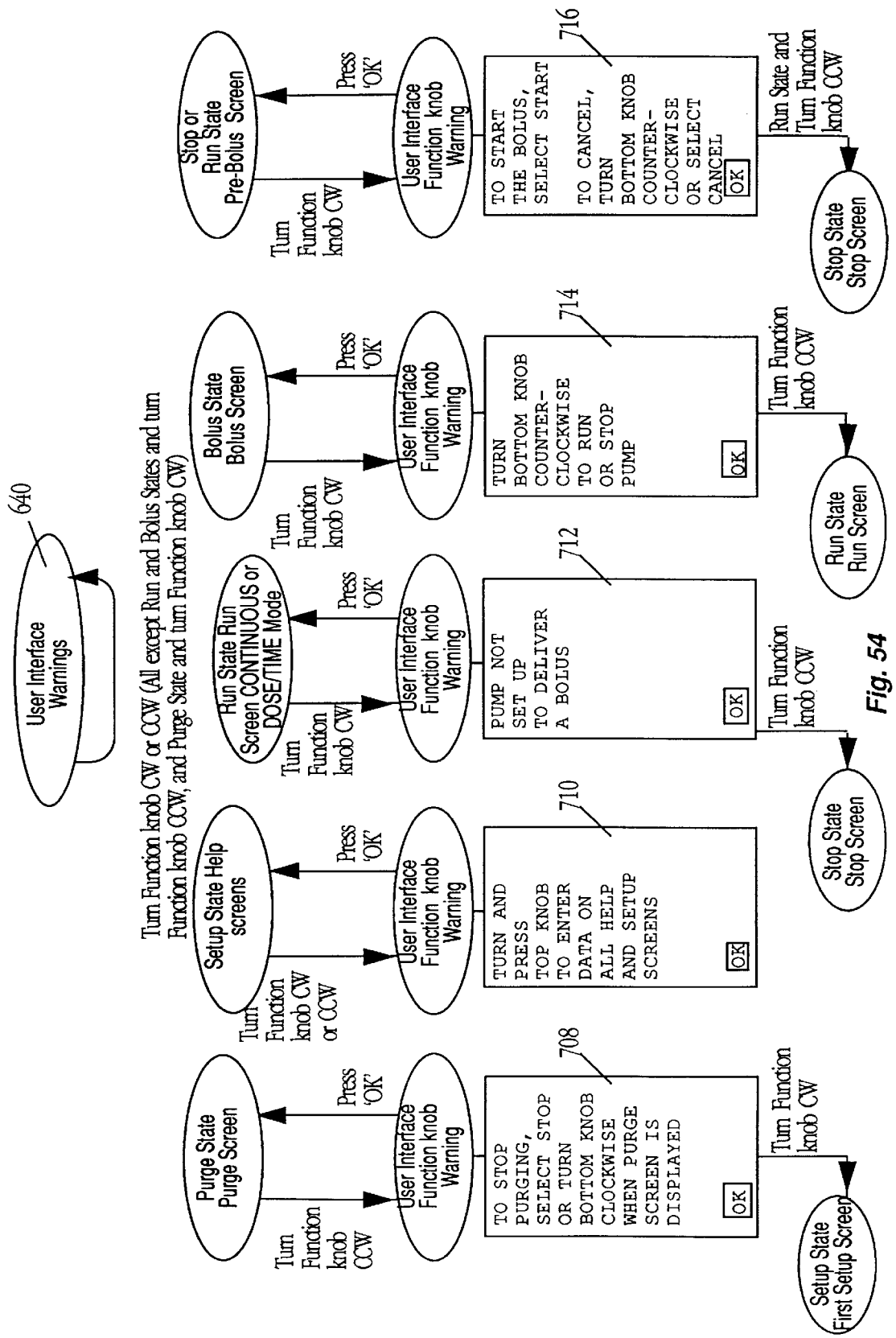
Figure 55:
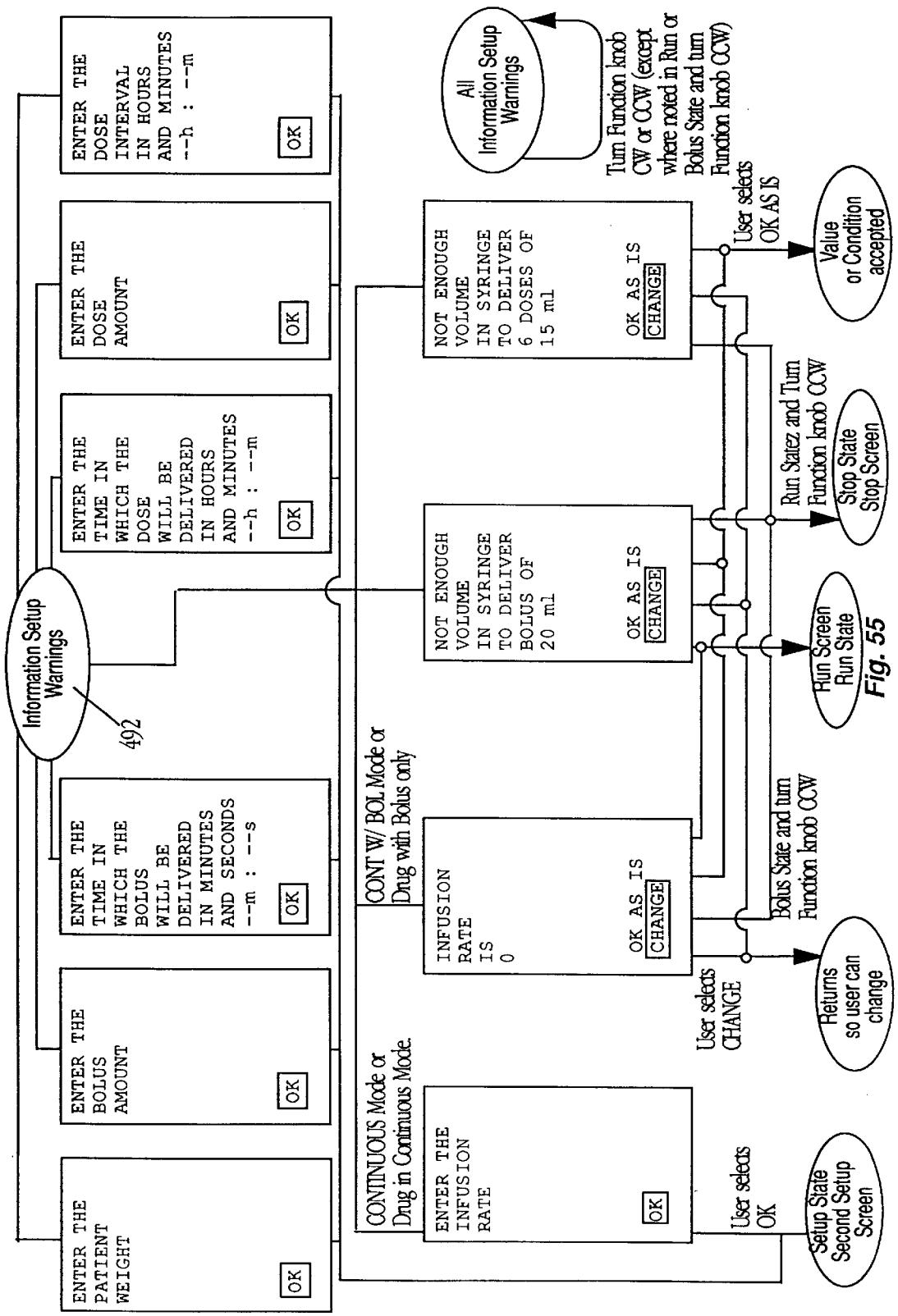
Figure 56:
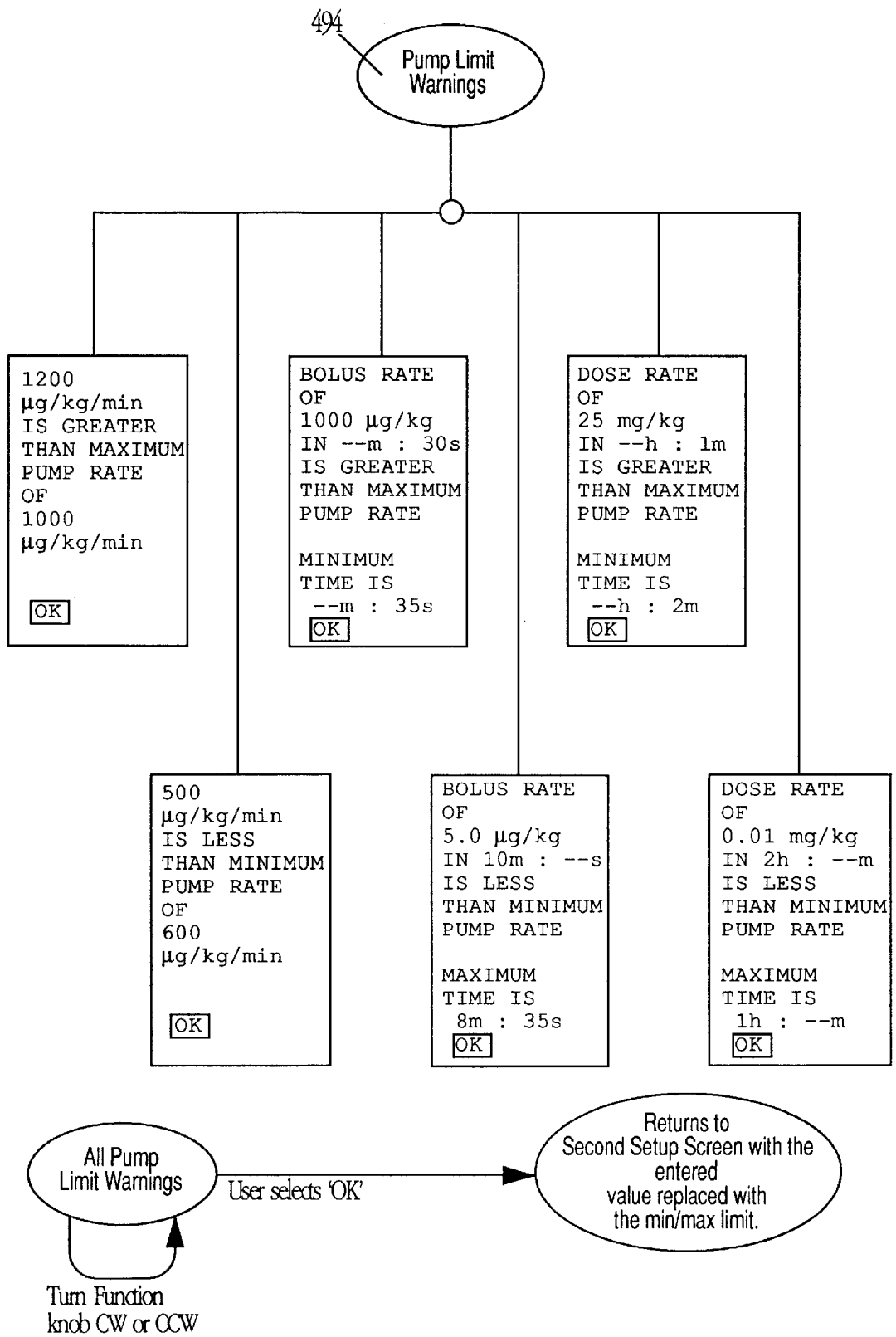
Figure 57:
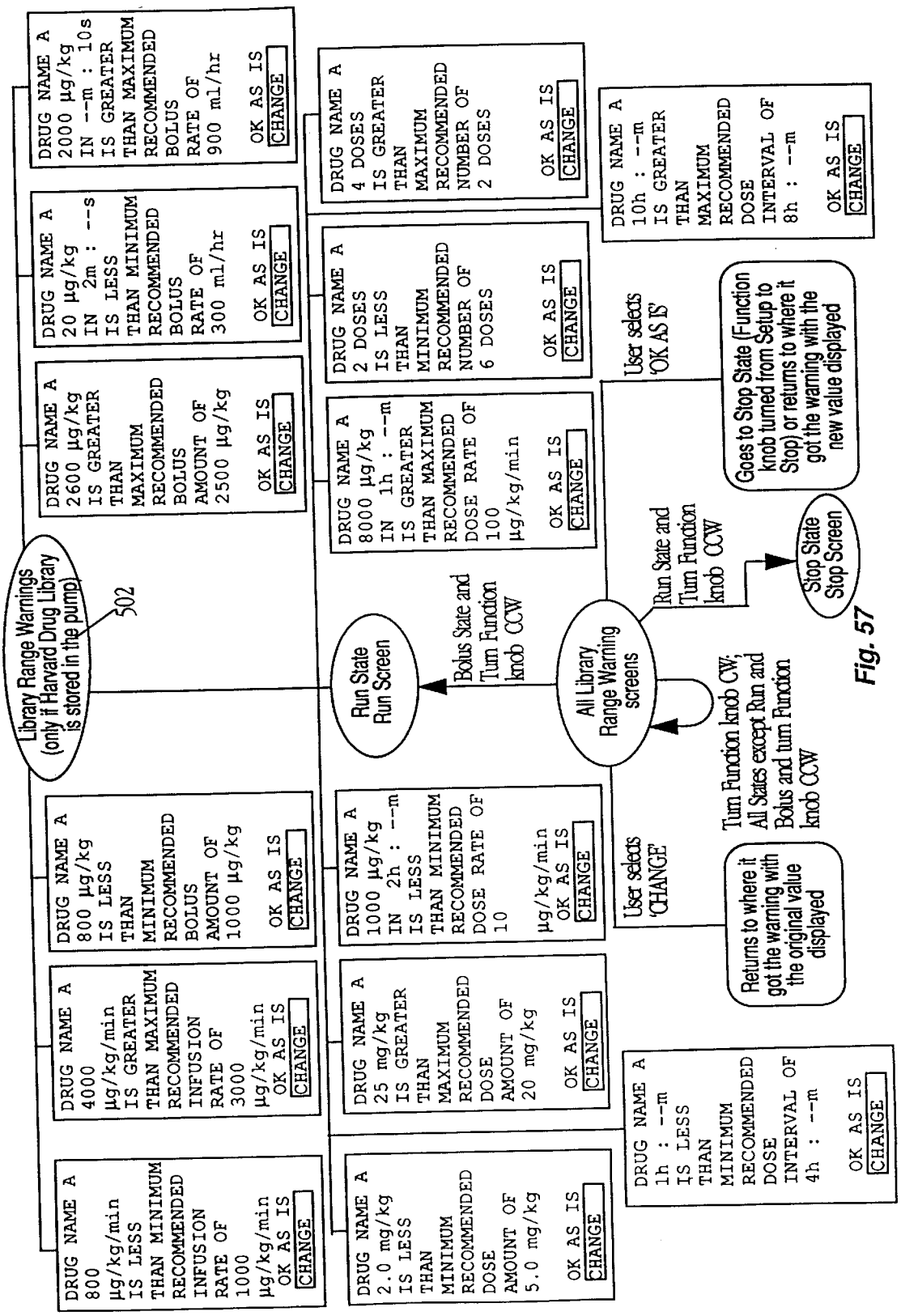
Figure 58:
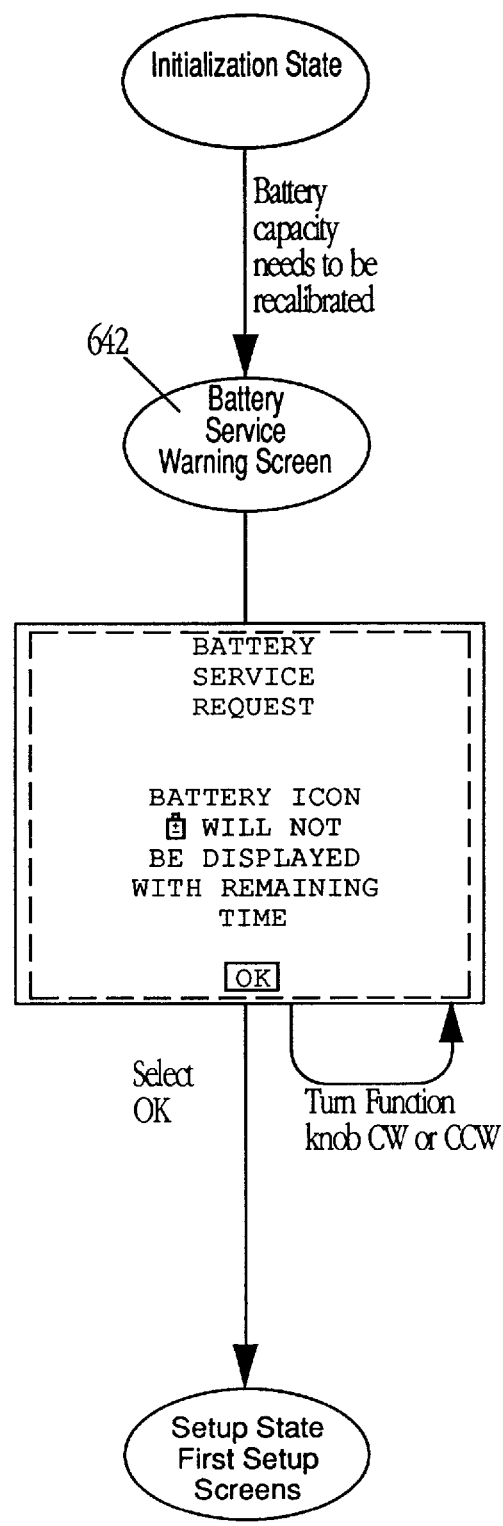
Figure 59:
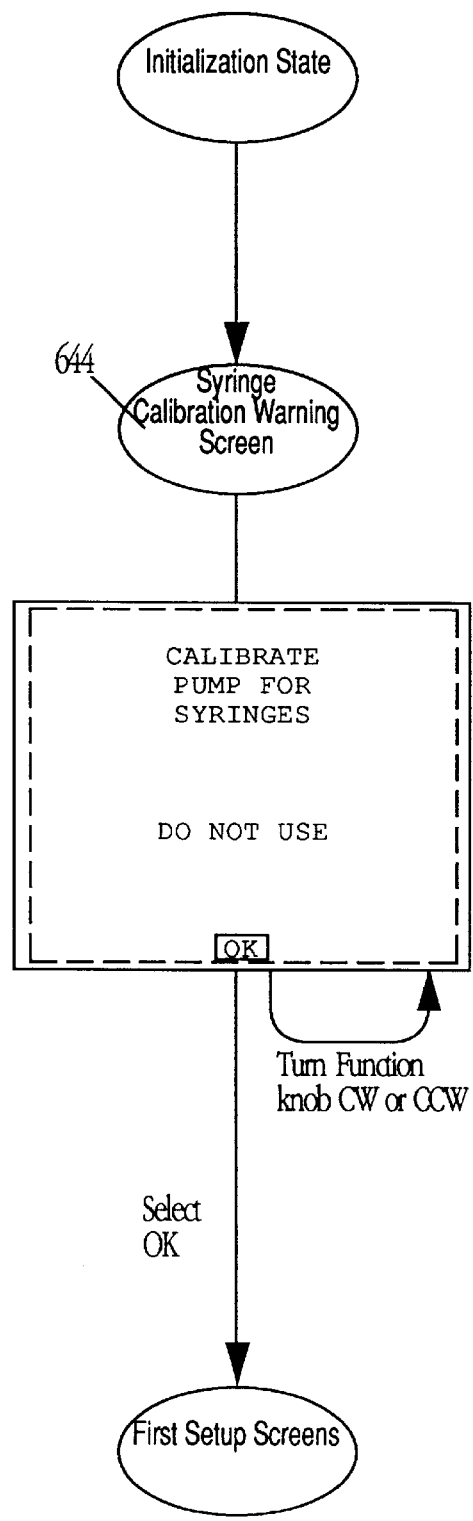

With reference now to FIG. 19, if a syringe has not yet been installed in the pump, the user is prompted by the first setup screen 204, 212 (see FIG. 52) to so install a syringe. After the user has installed the syringe, the pump can signal that the syringe has been recognized 216 via automatic detection of the syringe diameter by a potentiometer associated with the syringe barrel clamp, or that the pump has not recognized the syringe 218. In the latter case, either the syringe is installed improperly, or the wrong manufacturer is identified for the detected syringe. The user is given an opportunity to correct the situation 220 (see FIG. 52), after which the pump recognizes the syringe 216.

Typically, if the pump recognizes the syringe diameter, the screen will display the manufacturer associated with that syringe diameter and syringe size as previously entered and stored in non-volatile memory. Default values for the remaining settings found in the first Setup screen, such as Units/Type, Mode, and Concentration, are provided from memory based on most recent entries. Each of these elements may be altered by user selection via the data entry knob and pop-up menus, such as the selection of syringe manufacturer 222 as illustrated in FIG. 20.

In one embodiment of the present pump, the units/type, mode or drug name, and concentration that were last used in the pump are stored in non-volatile memory and are displayed in the first Setup screen 216 upon power-up. The user then has the option of either accepting the displayed information by selecting "[OK/NEXT]" or "[OK/RUN]" and transitioning to the second Setup screen 260 or Pre-Run screen 470 (see FIG. 32), or changing the infusion information.

Figure 20:
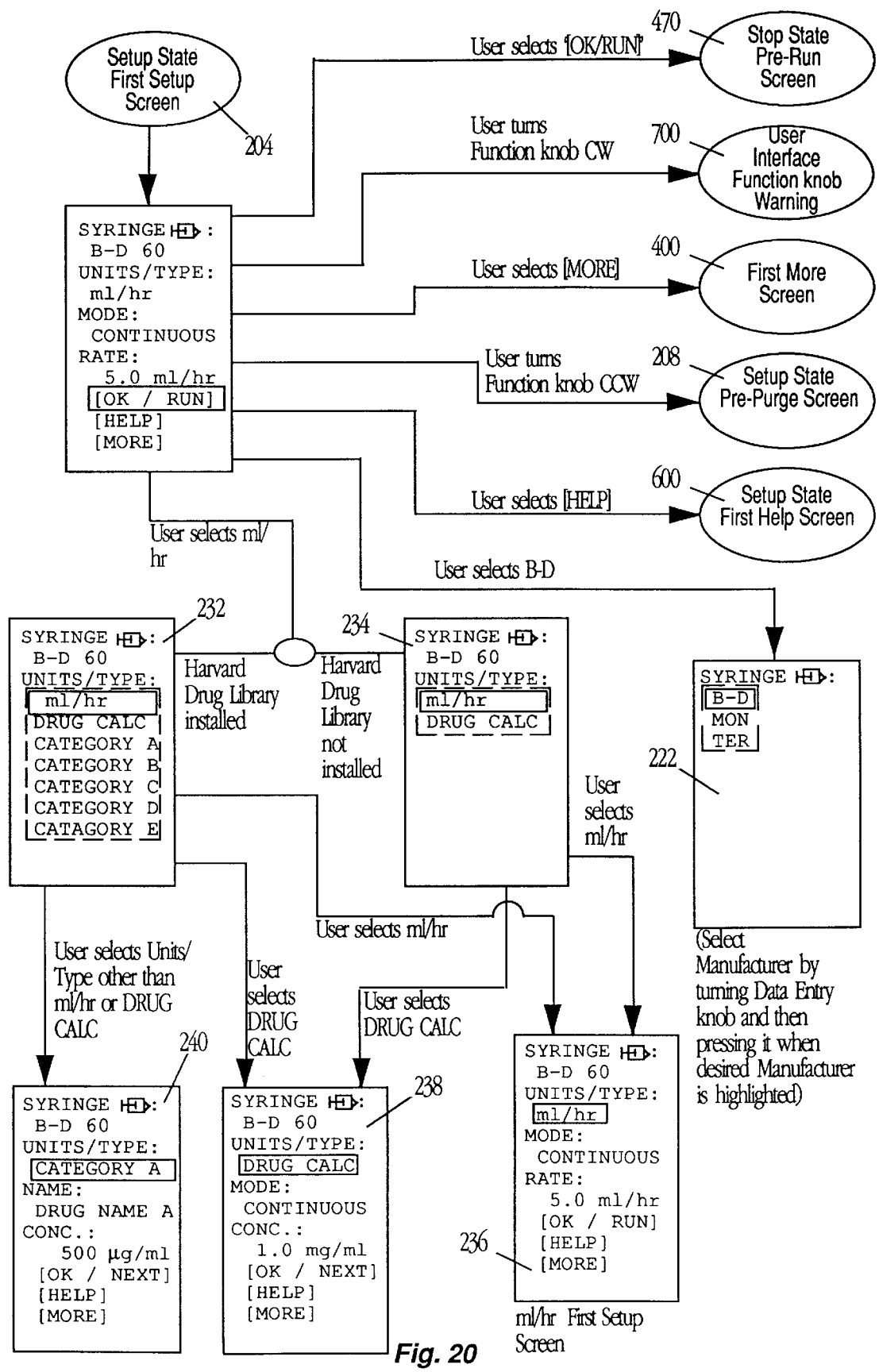
FIGS. 20–31 provide exemplary display screens in flow charts depicting definition of infusion parameters in the pump of FIG. 14.

As illustrated in FIG. 20, pop-up menus also provide the ability to select the appropriate units/type 232, 234, 236, 238 in all cases, and drug name 240 if a Drug Library is installed in the pump.

Figure 21:
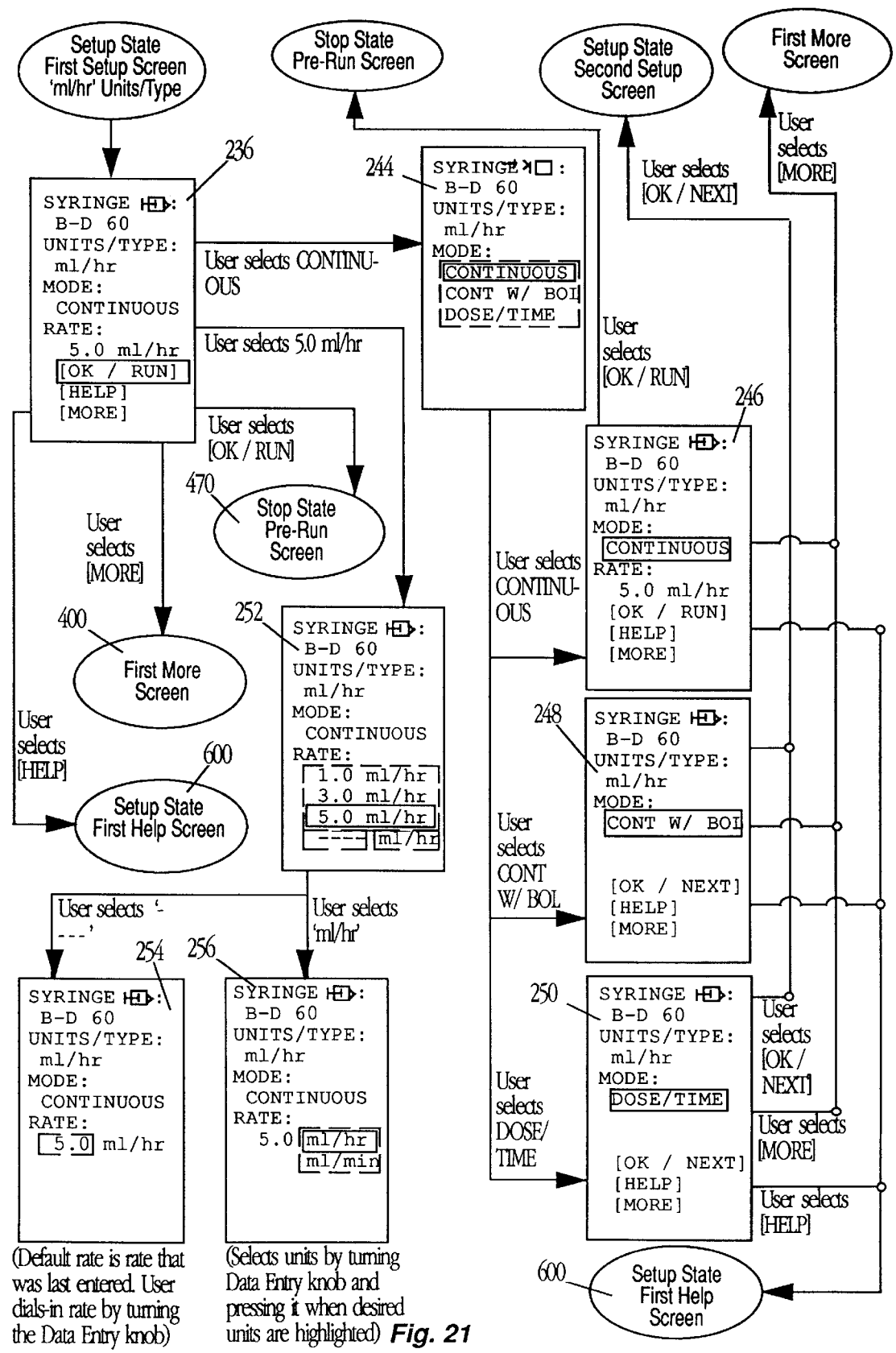

If the Units/Type has been chosen as "ml/hr", the user is presented with three mode options 244, as illustrated in FIG. 21: "CONTINUOUS" 246, "CONTINUOUS W/BOLUS" 248, or "DOSE/TIME" 250. In the "ml/hr" type "CONTINUOUS" mode case 246, once the user has selected the appropriate Mode, the user can accept the currently displayed Rate by selecting "[OK/RUN]", or can adjust it using the data entry knob prior to selecting "[OK/RUN]". The pump then transitions to the Stop state Pre-Run Screen 470, since all information required has been accepted.

Figure 24:
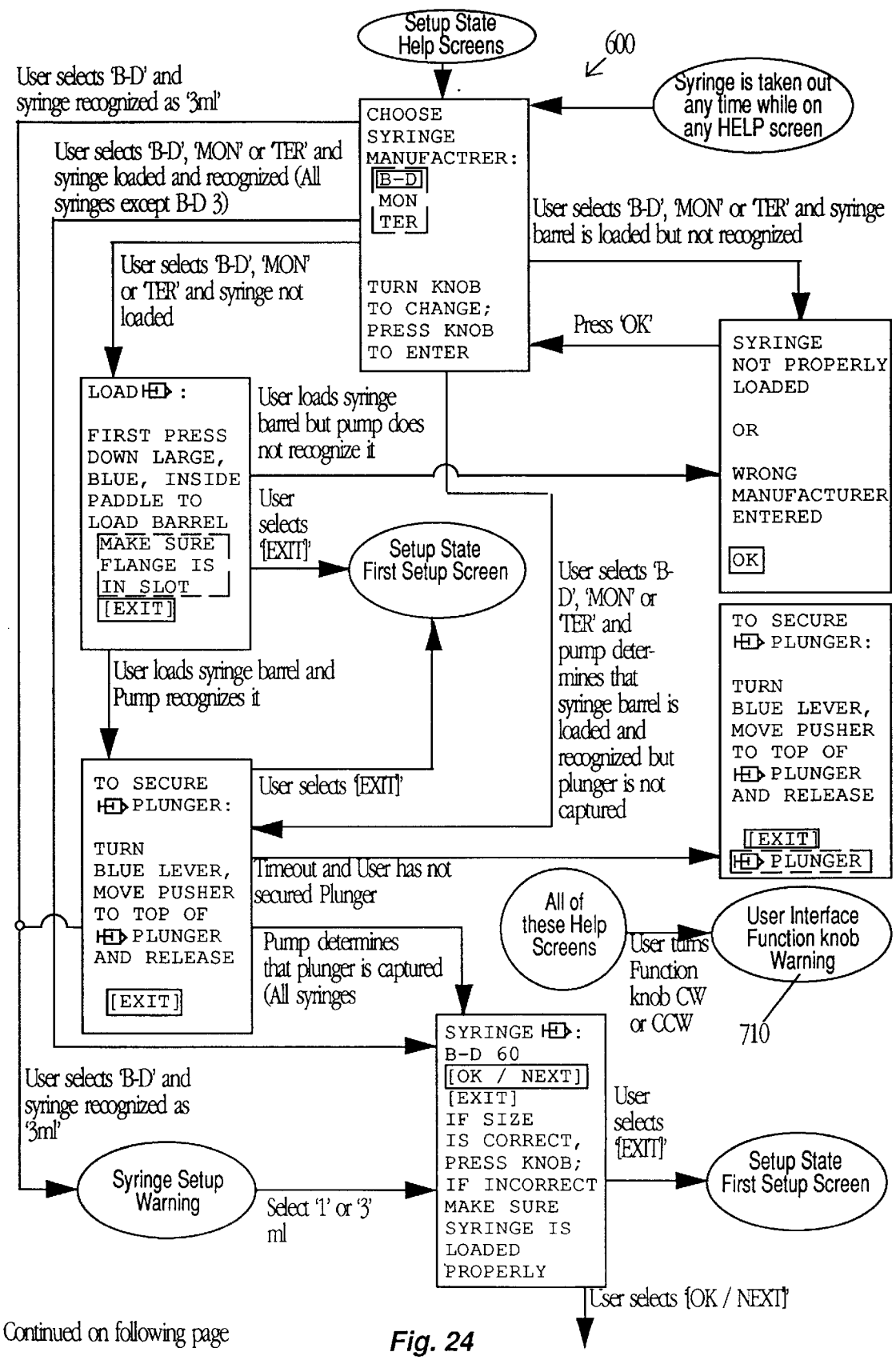
Figure 25:
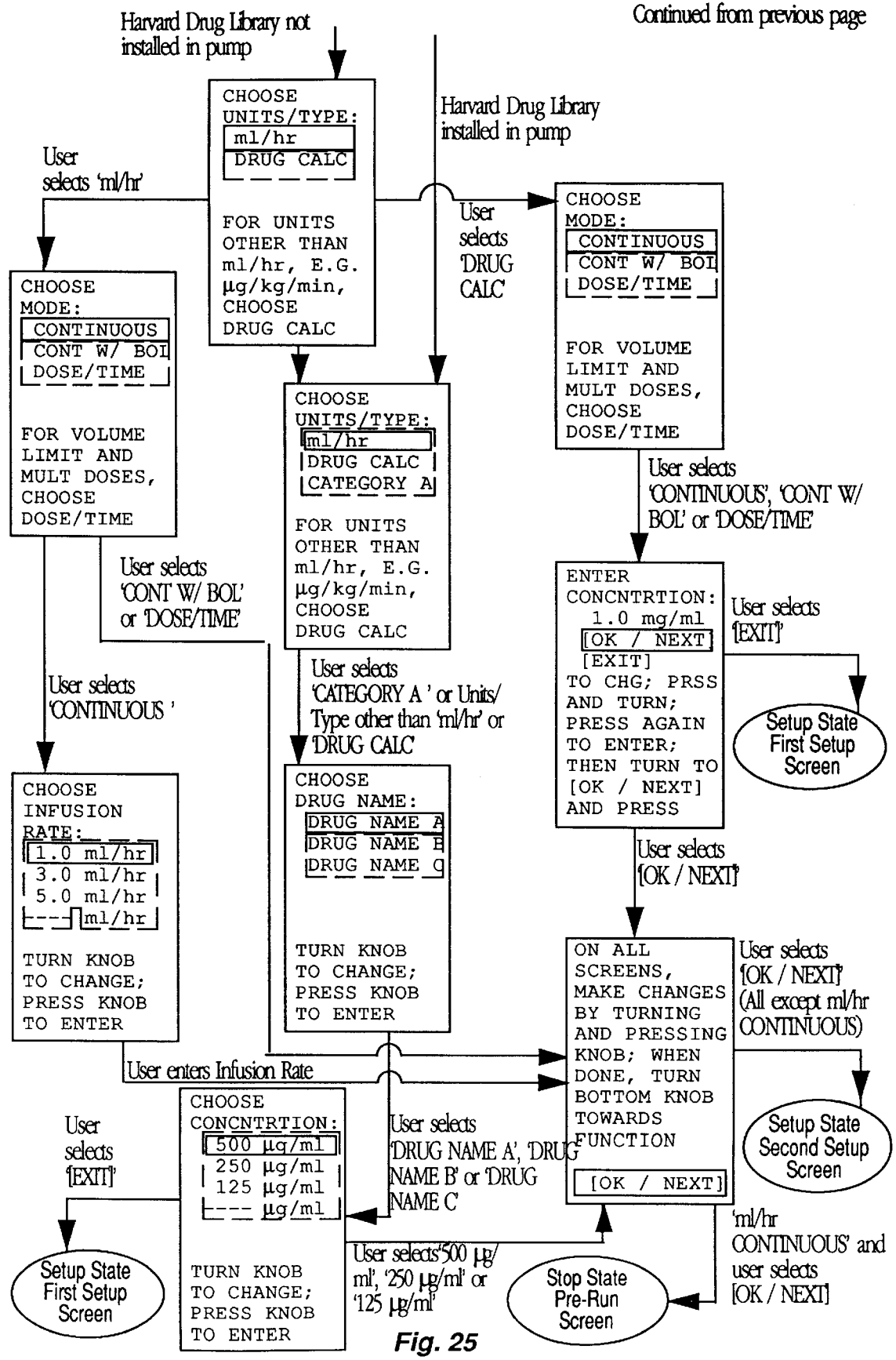

With reference to FIG. 14, if the user selects "[HELP]" from the first Setup screen, the pump will display one or more of the help screens illustrated in FIGS. 24 and 25. These Help screens, referred to generally as 600, provide instructions and prompt the user to enter all of the required information on the first Setup screen and load the syringe.

In the "CONTINUOUS W/BOLUS" 248 and "DOSE/TIME" 250 modes, more information is required to be supplied in the second Setup screen 206. Thus, selection of "[OK/NEXT]" from these screen variations 248, 250 causes the pump to display second Setup screens 300, 302, shown in FIG. 26.

At this point, i.e. from the first Setup screen, the user may also wish to alter other pump system information, which is accomplished by selection of the "[MORE]" option from any of the "CONTINUOUS" 246, "CONTINUOUS W/BOLUS" 248, or "DOSE/TIME" 250 variations. The More screens and the options available therein are discussed below.

Another value to be confirmed or altered by the user in the first Setup screen "ml/hr" Units/Type is the Rate information associated with the continuous mode 252. To enter a new value into the Rate field, the user may either dial in a new value using the Data Entry Knob 254, or by selecting a value from a menu of values 256. Again, acceptance of the data displayed in the first Setup screen with the mode set to "CONTINUOUS" causes the pump to transition to the Stop state and display the Pre-Run screen 470.

Figure 22:
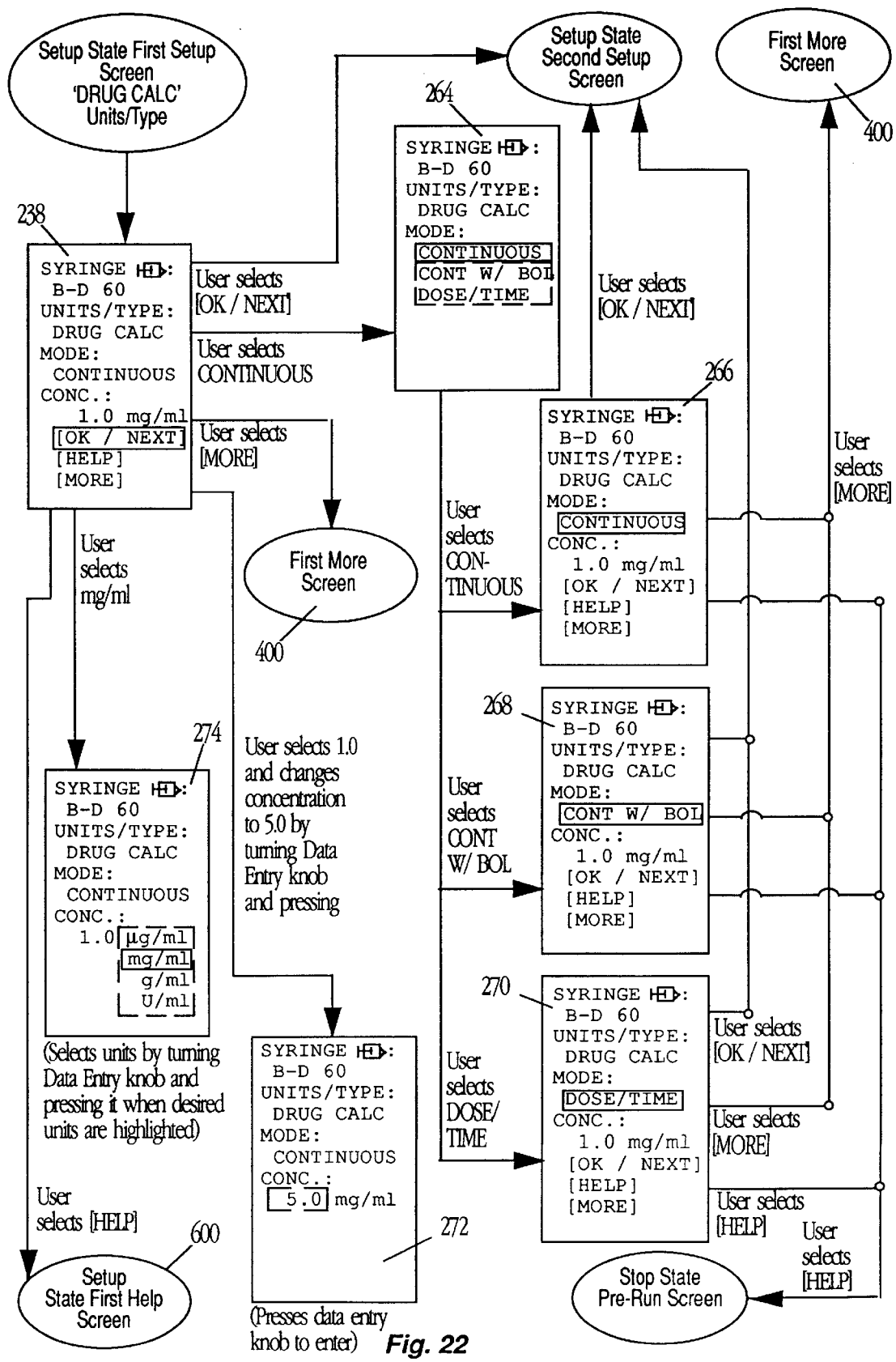
Figure 26:
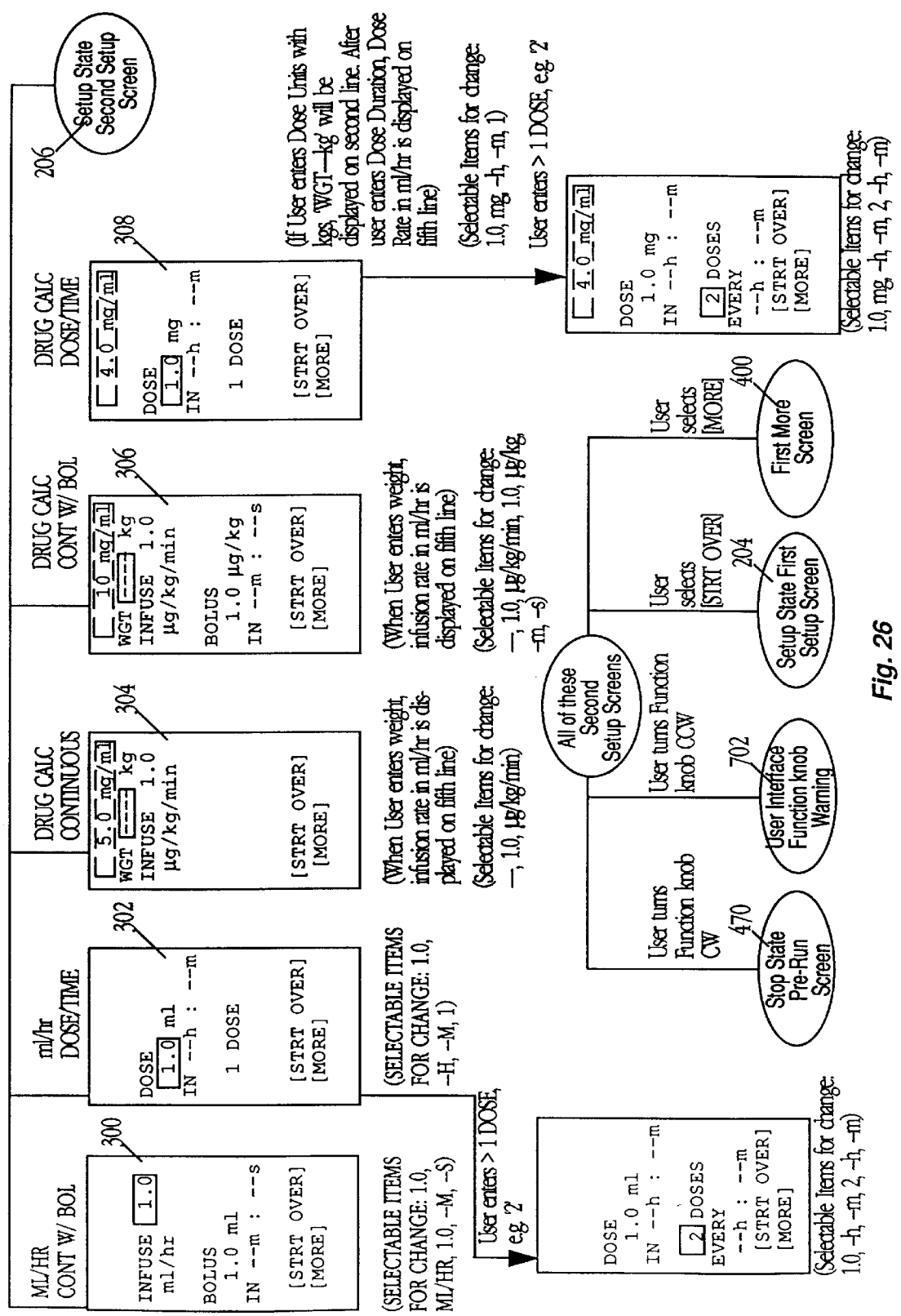
Figure 27:
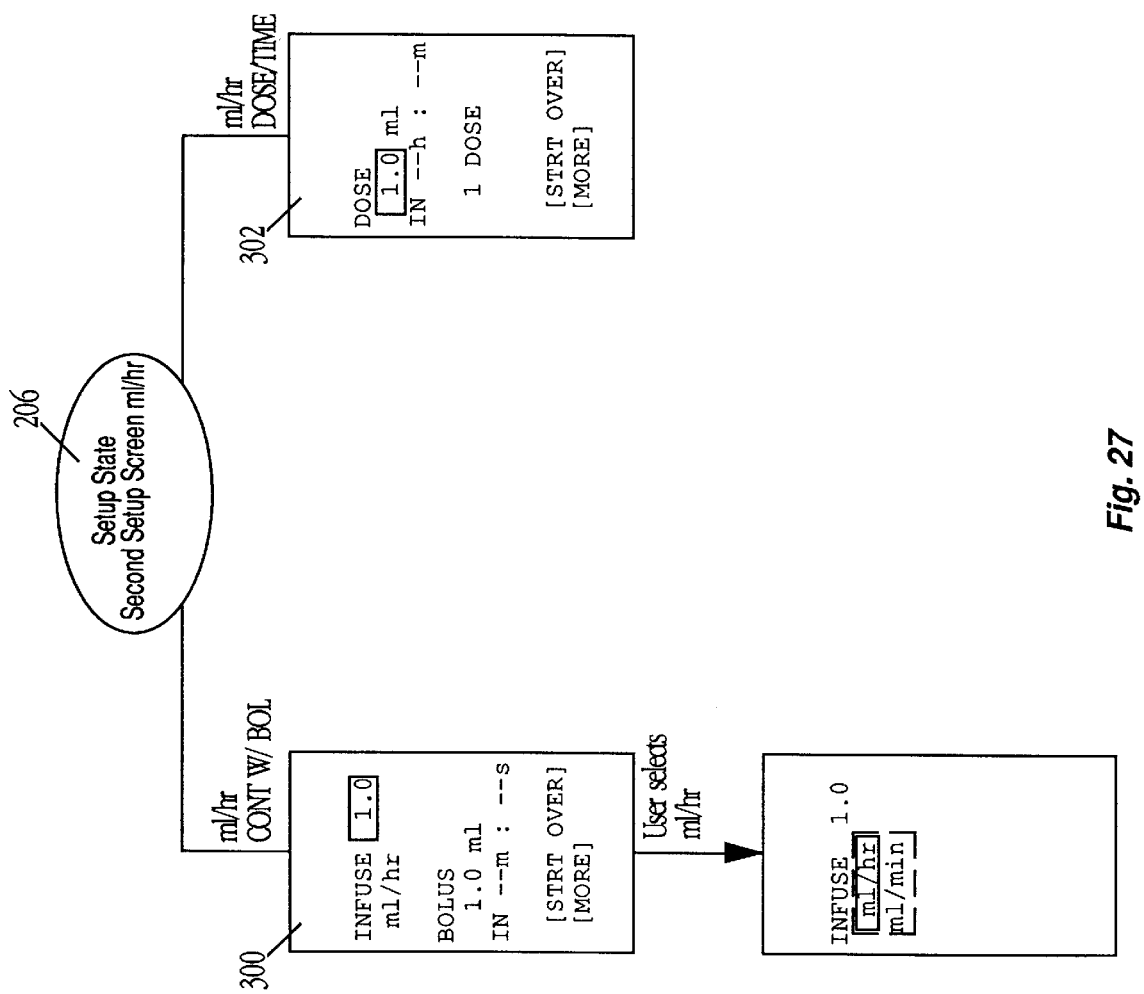
Figure 28:
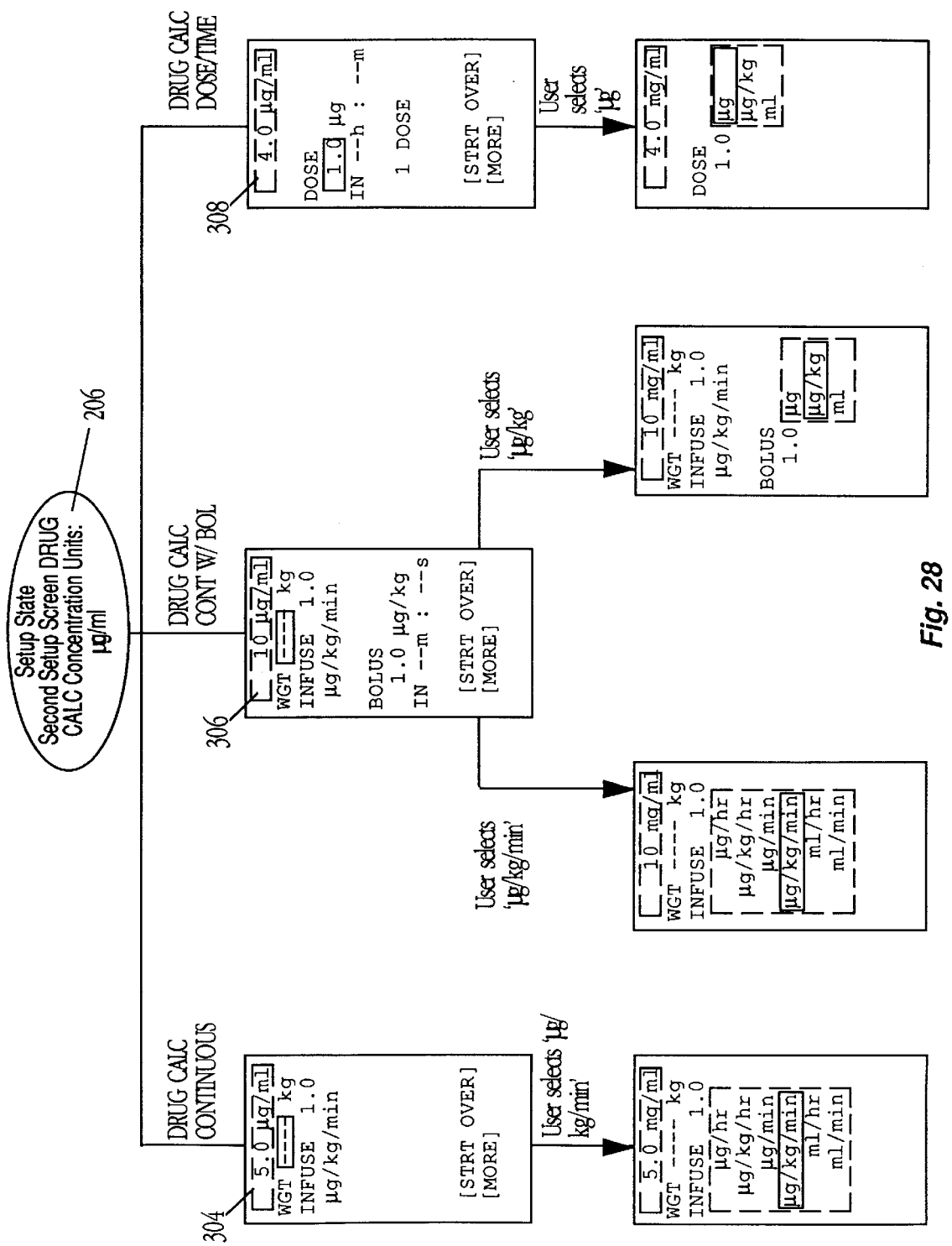
Figure 29:
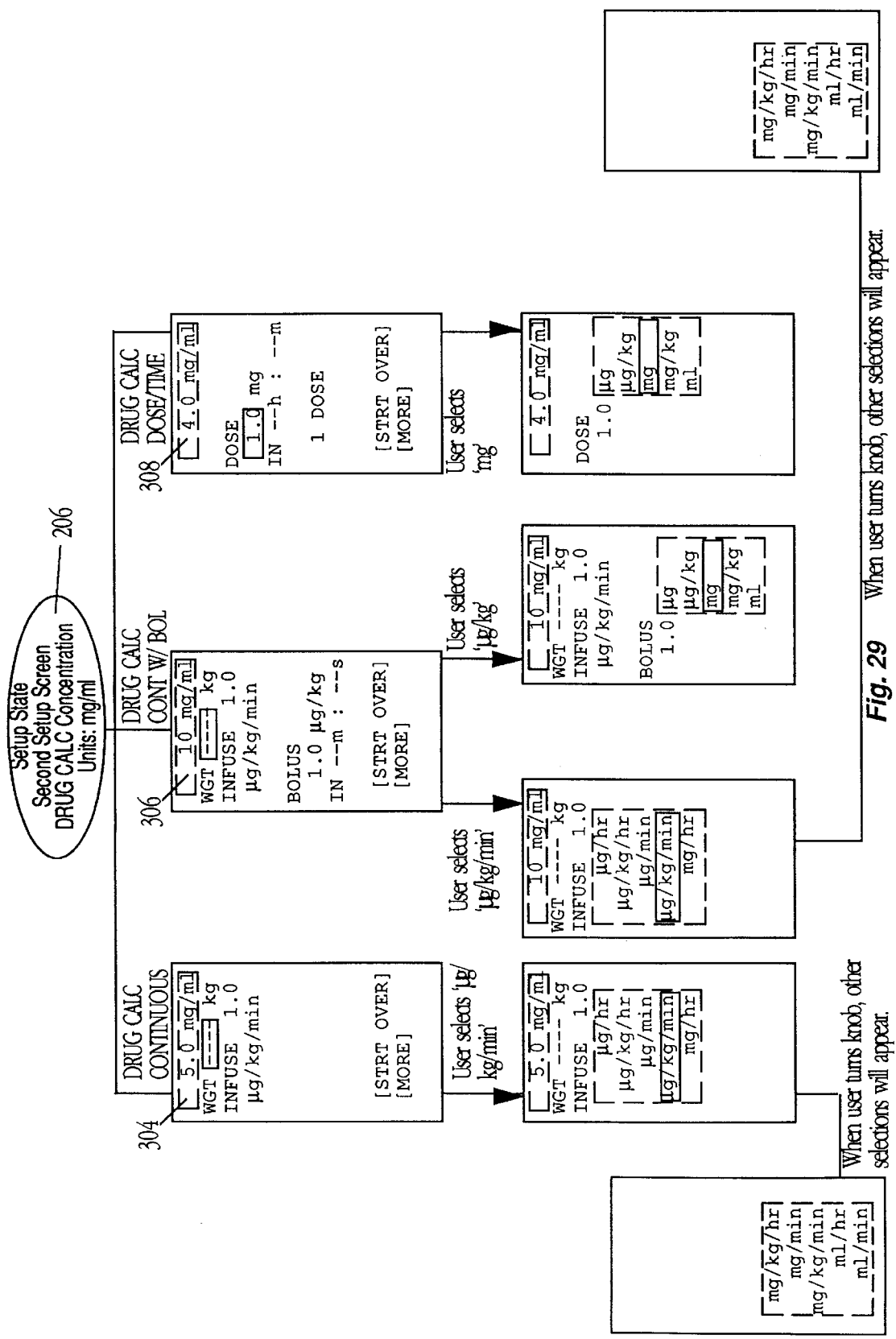
Figure 30:
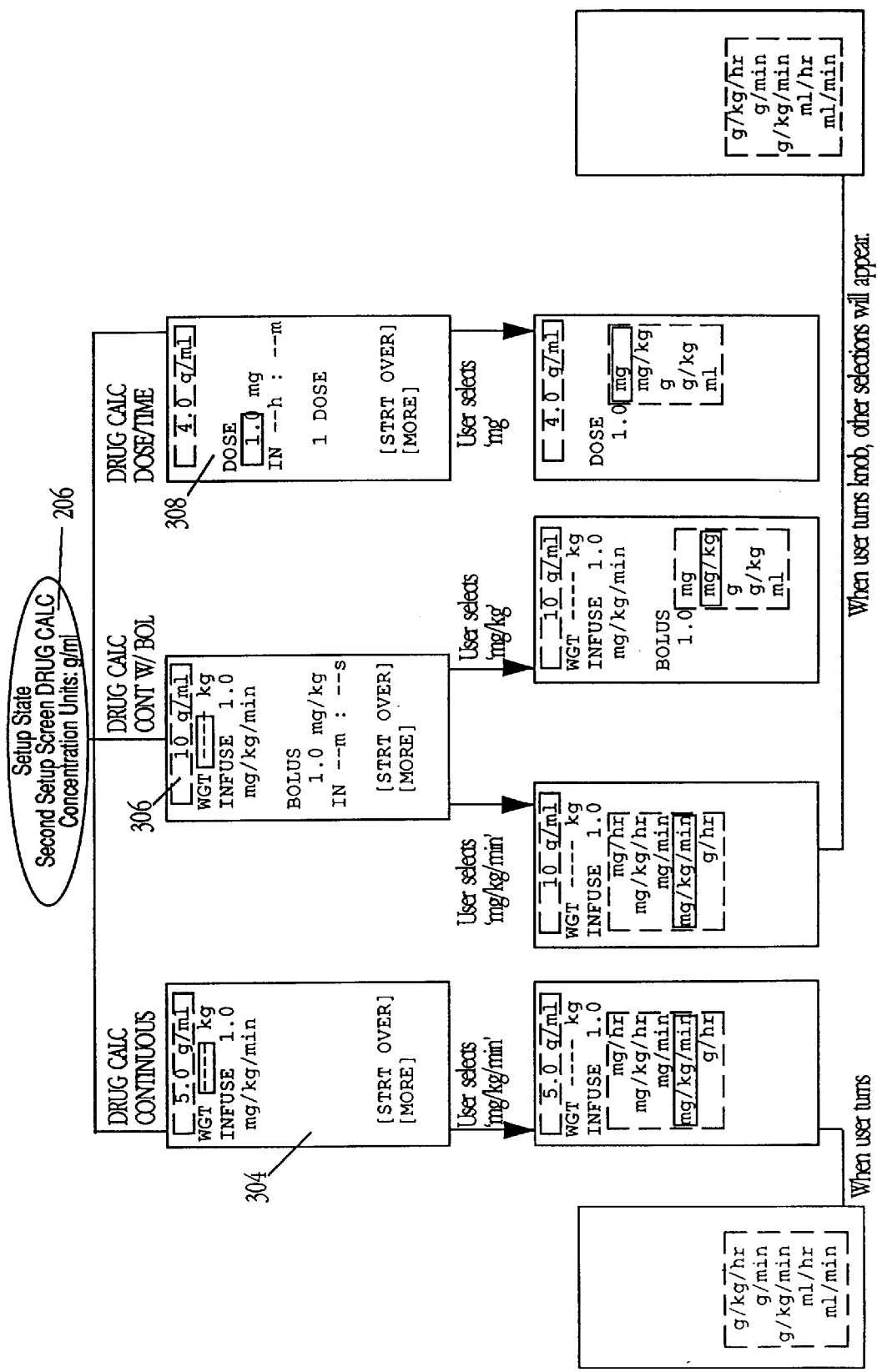
Figure 31:
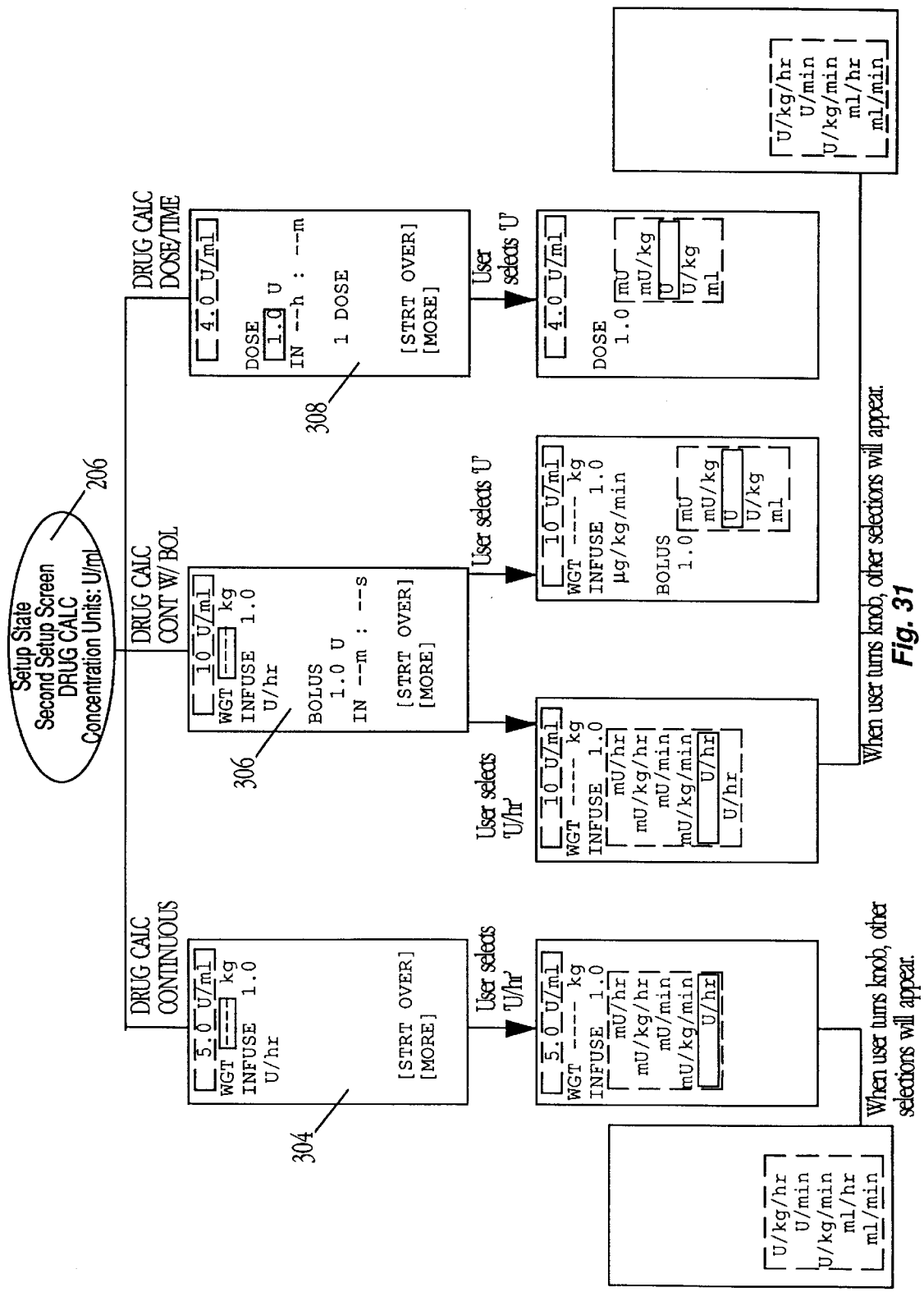

FIG. 22 illustrates that the variations on the first Setup screen associated with the "DRUG CALC" Units/Type 238 are quite analogous to those displayed when the Units/Type has been set to "ml/hr" 236, shown in FIG. 21. Specifically, Mode options 264 include "CONTINUOUS" 266, "CONTINUOUS W/BOLUS" 268, and "DOSE/TIME" 270. However, with the Units/Type set to "DRUG CALC" (FIG. 22), the user has the ability to select the desired concentration 272 and units 274 from the first Setup screen 238. Note that when the Units/Type is set to "DRUG CALC", acceptance of the information provided by the first Setup screen causes the display of a unique second Setup screen 304, 306, 308 for all variations (i.e. for all Modes 266, 268, 270, respectively), as illustrated in FIG. 26.

Figure 23:
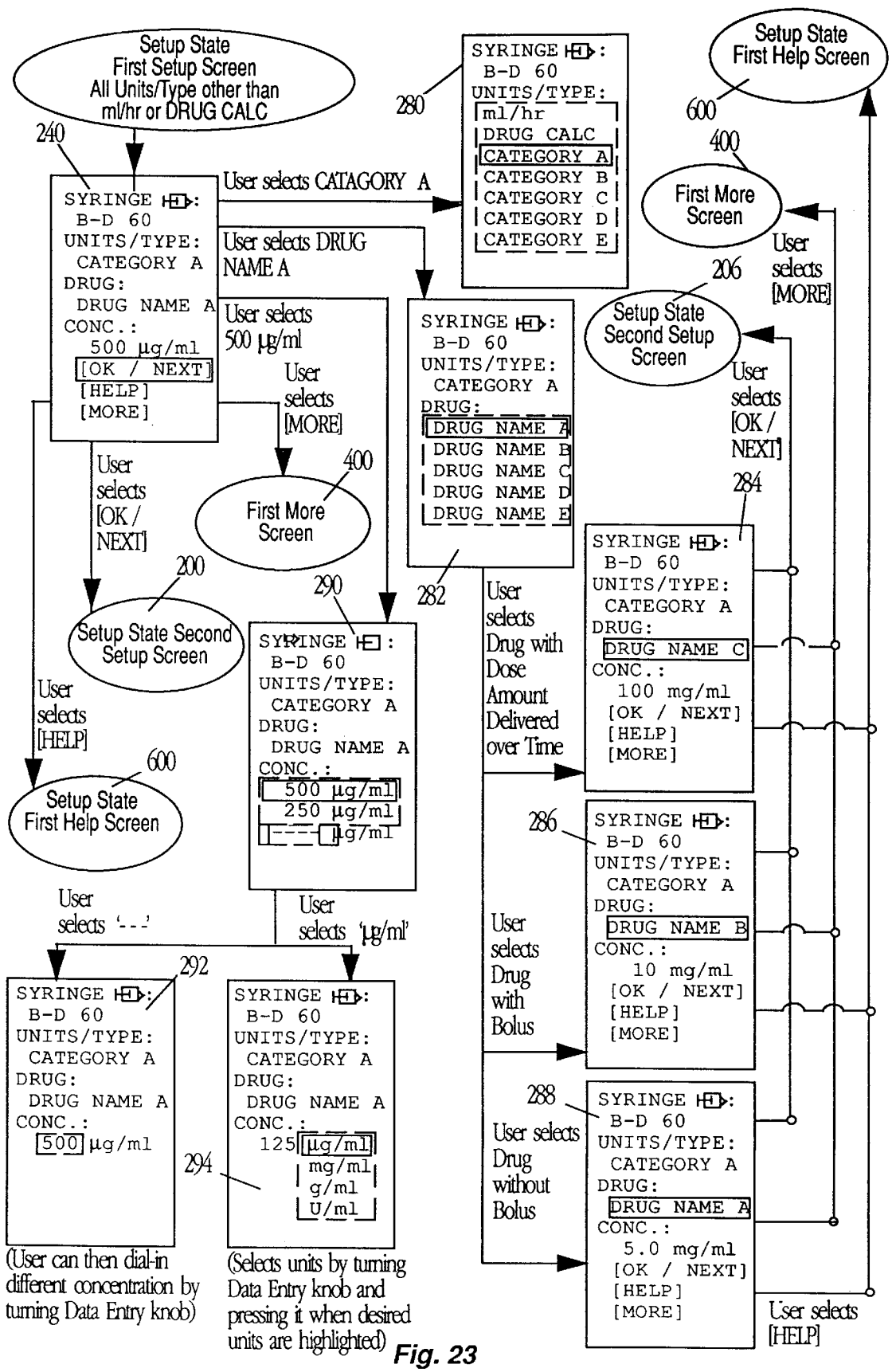

For the Units/Type to be set to any option other than "ml/hr" 236 or "DRUG CALC" 238, a Drug Library must be installed in the pump. The first Setup screen in this case 240, FIG. 23, will have a Units/Type name taken from a menu 280 of names provided on the display. As noted below in further detail, drug names can be categorized into various Types by the user in the Drug Library.

The next field to be addressed in the drug Setup screen 240 is the Drug, which is selected from a menu 282 similar to the Units/Type menu 280. Note that with the "ml/hr" and "DRUG CALC" Types 236, 238, the next entry was Mode. In the case of any other Units/Type, this next entry is Drug. The drug chosen from the subsequent menu 282 will initiate the display of one of three further variations 284, 286, 288 on the first Setup screen 240 for this Units/Type, each displaying a default value for drug concentration stored in association with the selected drug in the library. In each case, acceptance of the default concentration values invokes second Setup screens similar to those for "DRUG CALC" Units/Type shown in FIG. 26 but with the drug name displayed and defaults from the Drug Library displayed for all of the selectable parameters. Selection of the "[MORE]" option enables the user to manipulate the options discussed herein with respect to the More screens.

As with the "DRUG CALC" Units/Type 238, the user has the option of dialing in another concentration 290, 292, and/or changing the default units 290, 292, 294 in the first Setup screen for the drug Units/Type. In addition, other default concentrations may be selected from the menu.

In FIGS. 27, 28, 29, 30 and 31, exemplary second Setup screens are displayed for "ml/hr" Units/Type and "DRUG CALC" Units/Type with concentrations of ug/ml, mg/ml, g/ml and U/ml indicating the units that can be selected for the infusion rate, bolus amount and dose amount.

As noted, the second Setup screens 206 are illustrated in FIGS. 26 through 31. In each case 300, 302, 304, 306, 308, further options are provided for defining the desired drug infusion, including infusion value and units or dose value and units, dose time in hours and minutes, number of doses and dose interval in hours and minutes, bolus quantity and units, bolus time in minutes and seconds, and patient weight. These options are selected as above, in that the user can dial in a desired number, or can select desired units from a menu.

Once all of the information required in the Setup screens has been entered by the user, the function knob is turned by the user to light the Stop LED and display the Pre-Run screen 470. If the Setup information to be supplied is incomplete, one or more of the Information Setup 492, Pump Limit 494 or Library Range Warning 502 screens will be displayed and the Setup LED will remain lighted.

Stop

The Stop state is entered by turning the function knob clockwise from the Setup state first or second Setup screen to display the Pre-Run screen 470. The Run state is then accessed by pressing the data entry knob when "START" is highlighted.

The Bolus state 482 can be accessed to infuse a displayed bolus amount over a specified period of time by turning the function knob further clockwise from the Stop state Pre-Run screen 470 to display the Stop state Pre-Bolus screen 480 and then pressing the Data Entry knob when "START" is highlighted.

Figure 34:
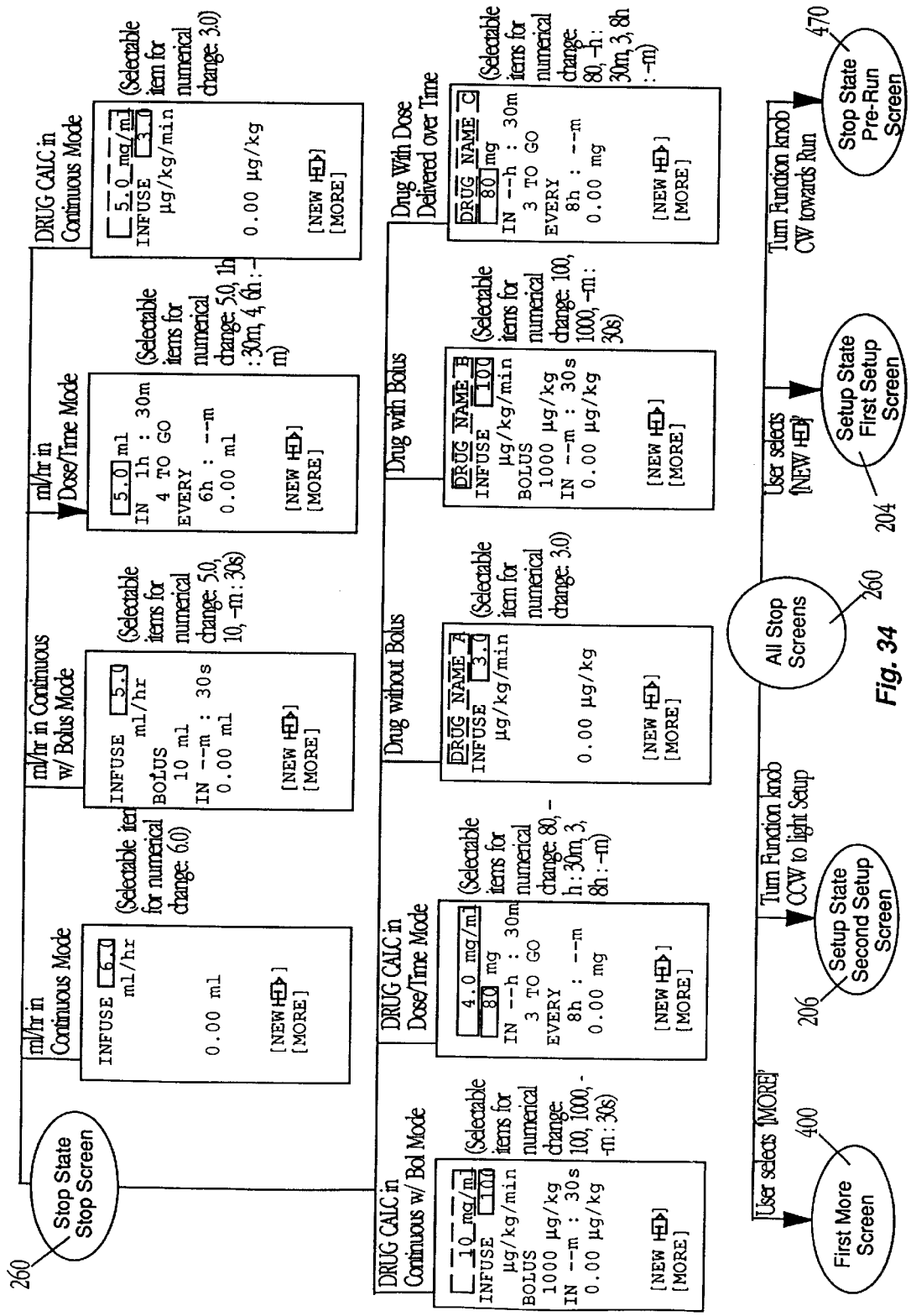

Once the function knob is turned counterclockwise from the Pre-Run screen, "CANCEL" is selected from the Pre-Run screen or the user does nothing for a brief period of time, the Stop state Stop screen 260 is displayed. As indicated in FIG. 34, displayed information in the Stop state 260 includes: concentration or drug name; infusion rate; bolus amount and duration; dose amount; dose duration; number of doses; dose interval; and the total amount of drug infused. The entered Setup information, with the exception of the infusion rate value, Bolus Amount and Duration, and Dose Amount and Duration, Number of Doses and Dose Interval may not be changed.

From the Stop state Stop screen, the following states and functions can be accessed. The Setup state first screen 204 can be entered to change a syringe or to enter new information for a new drug by user selection of the new syringe option displayed on the Stop screen 260. The second Setup screen 206 is displayed if the user turns the function knob to illuminate the Setup LED from the Stop state. The Pre-Run screen is displayed if the user turns the function knob clockwise. Finally, the user has access to the options available in the More screens by selecting the [MORE] option 400 from the Stop screen.

Run

Figure 35:
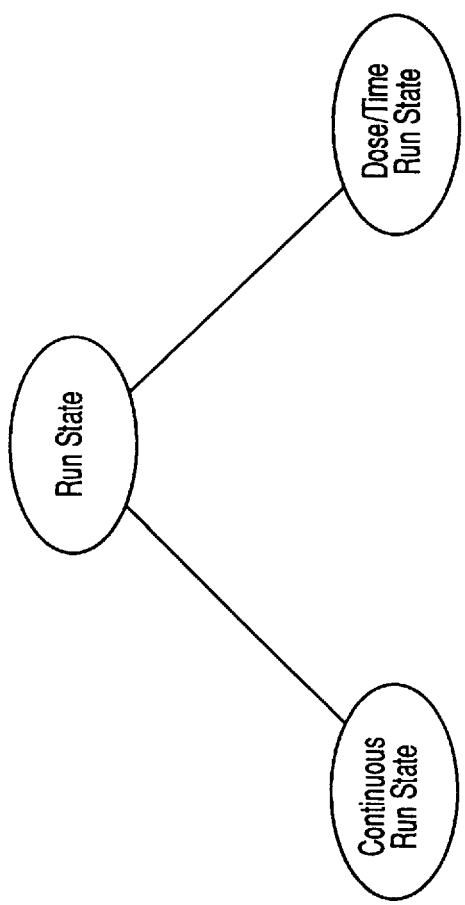
FIGS. 35–38 provide exemplary Run state display screens for the pump of FIG. 14.

Each pump has two run states as indicated in FIG. 35: Continuous; and Dose/Time. In Continuous Run state, the pump delivers a drug at the displayed rate until the function knob is turned from the Run state to Stop or a Bolus is confirmed if the Mode is "CONTINUOUS W/BOLUS". In the Dose/Time mode, one or more fixed dose amounts of drug are infused over a specified period of time. The doses may be repeated automatically at set intervals.

The Run state is determined by the Mode associated with the Units/Type defined in the first Setup screen 204. If the Units/Type is "ml/hr" or "DRUG CALC", the Mode must be chosen from among "CONTINUOUS", "CONTINUOUS W/BOLUS", or "DOSE/TIME". If a Drug Library is installed in the pump and the Units/Type in the first Setup screen was chosen from this Library, the Mode is determined by the drug selected from a Drug Library.

Figure 32:
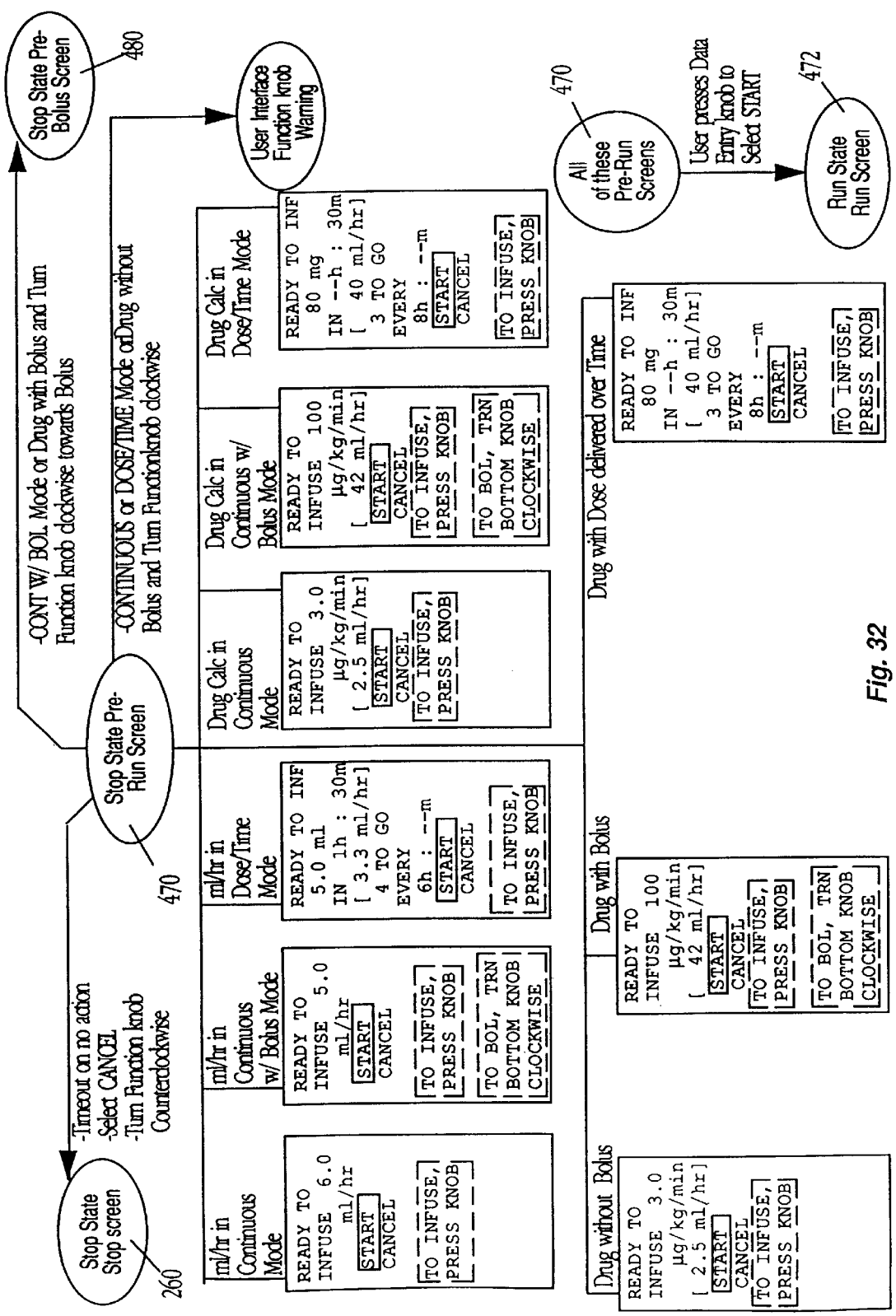
FIGS. 32–34 provide exemplary Stop state display screens for the pump of FIG. 14.

Upon turning the function knob clockwise from the Setup state or Stop state, a Pre-Run screen 470 is displayed, as in FIG. 32, and the Stop LED will be lighted. The Pre-Run screen 470 provides a summary of the infusion information entered in the Setup screens 204, 206. In FIG. 32, an exemplary Pre-Run screen is illustrated for each of the Units/Type, Mode combinations. Note that for each of these screens, pushing the data entry knob causes a Run screen 472 to be displayed (FIG. 36) and the pump to begin infusing. If the mode is "CONTINUOUS W/ BOLUS" and the user turns the function knob further clockwise, the pump will transition to the Pre-Bolus screen 480, to be discussed. Otherwise, the user can turn the function knob counterclockwise to display the Stop screen, or the user can do nothing for a fixed period of time. In either case, the pump will display the Stop screen.

Figure 36:
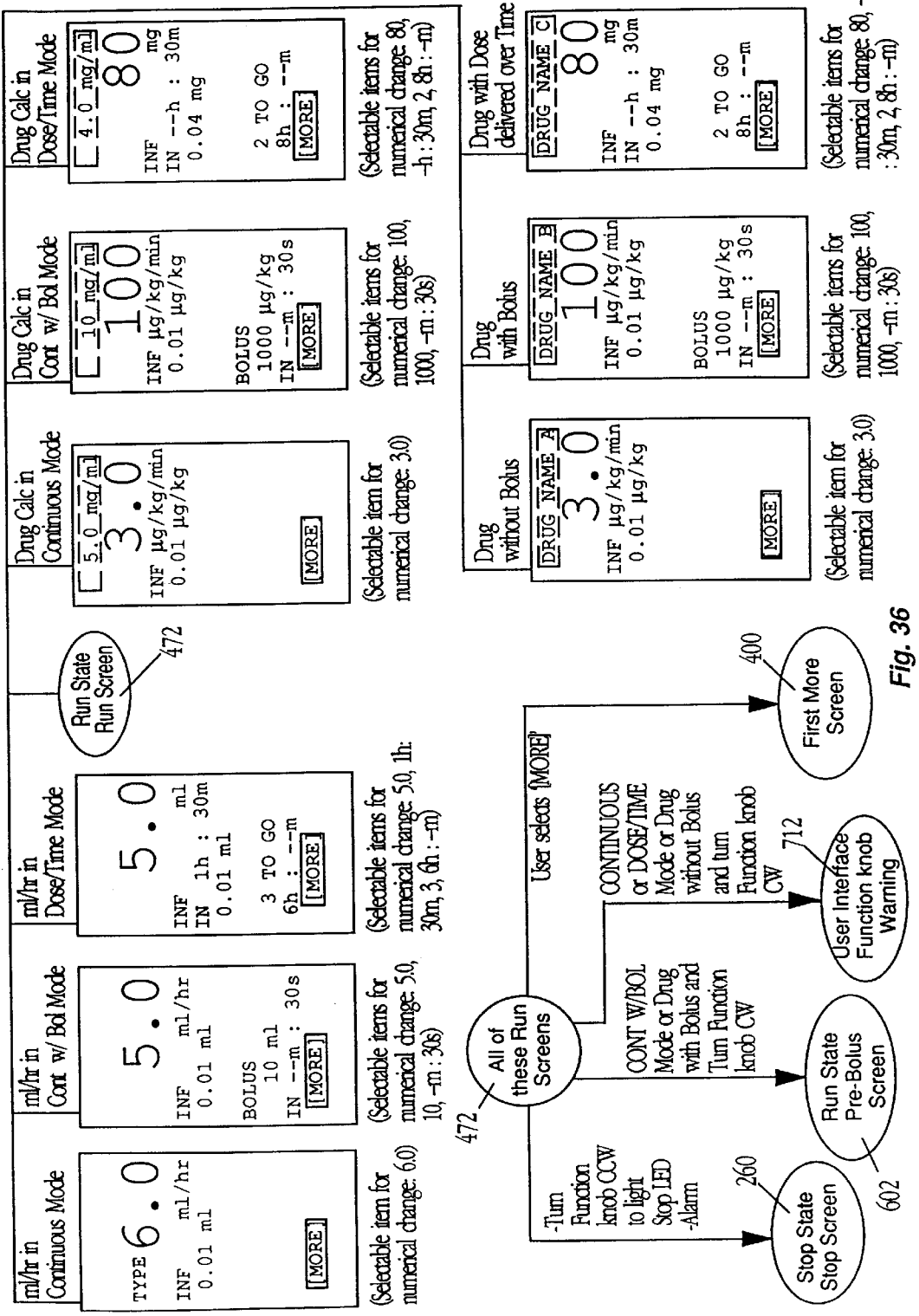

Once the Run state has been activated and the Run screen 472 is displayed as in FIG. 36, the pump begins running according to the specified parameters, and total amounts infused are updated and displayed. Also in FIG. 36 are examples of Run state screens for each of the Units/Type, Mode combinations.

The various pathways out of these various Run state screens 472 are also illustrated in FIG. 36. By turning the function knob to light the Stop LED, or if an alarm is triggered, the pump enters the Stop state 260. If the mode is "CONTINUOUS W/ BOLUS", by turning the function knob clockwise toward the Bolus LED, the pump continues running, but displays the Run state Pre-Bolus screen 602. Once the data entry knob is pressed to select START, the Bolus state is entered and the Bolus screen 482 is displayed. Finally, if the user selects "[MORE]" from the Run state screen, the pump continues to infuse while the user is presented with the first More screen 400, described above.

Figure 38:
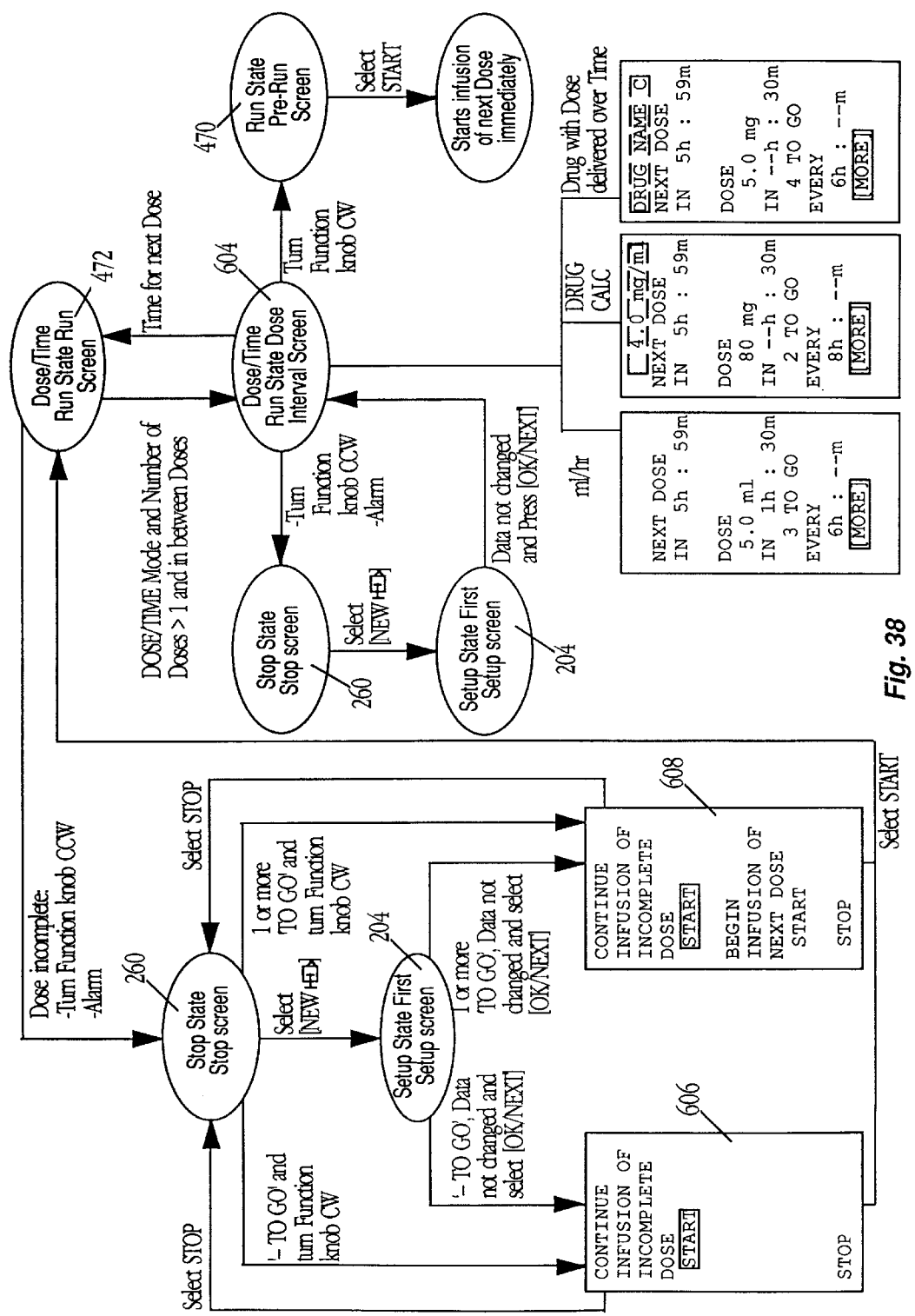

As indicated in FIG. 38, if the Run state is Dose/Time and the number of doses is greater than one, after each does is given, the Dose Interval screen 604 will be displayed and the time will decrement until it is time for the next dose and the Dose/Time Run screen is again displayed. If the delivery of the dose or doses is incomplete, the pump will prompt the user to continue the infusion of the incomplete dose 606, 608 begin the infusion of the next dose 608 (if the number of doses is greater than one), or stop 606, 608.

Infusion of a drug while the pump is in the Run state can also be accomplished by patient demand. In order to enable patient controlled analgesia (PCA), and/or patient controlled sedation, a patient actuator such as a thumb switch is provided, one for each pump module. To avoid confusion between thumb switches, one such switch can have a square cross-section while another can have a round cross-section. Further, identifying letters or numbers such as "L", "R", "1", or "2" are disposed on the thumb switches to identify the associated pump module. A connector such as an RJ-11 connector can be employed as the interface between the thumb switch and the pump. The pump may further have circuitry which senses the presence of a thumb switch and may condition the enablement of PCA on its presence.

From the any mode, a user can enable PCA by selecting the appropriate icon on the display and entering information relevant to PCA including the ability to define the quantity of drug to be infused upon each patient activation of the thumb switch and the maximum amount of drug the patient can infuse over a specific period of time. A software lockout and mechanical means are provided for preventing the patient from changing the infusion information and from manually pushing the syringe plunger into the syringe barrel. Note that the continuous infusion rate can be set to zero, so that the pump can solely provide PCA.

Figure 39:
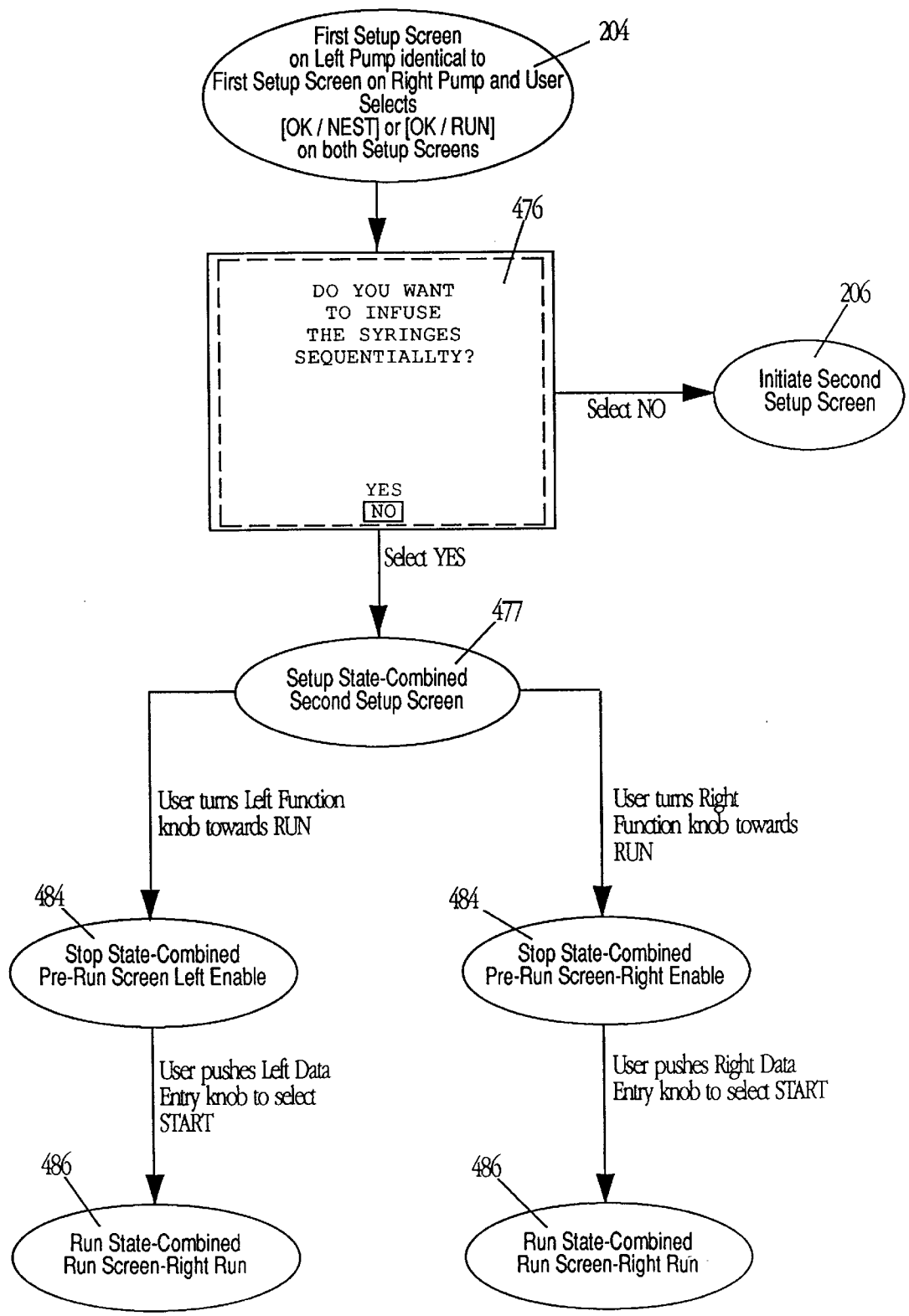
FIGS. 39 and 40 provide exemplary sequential mode screens for the pump of FIG. 14.
Figure 40:
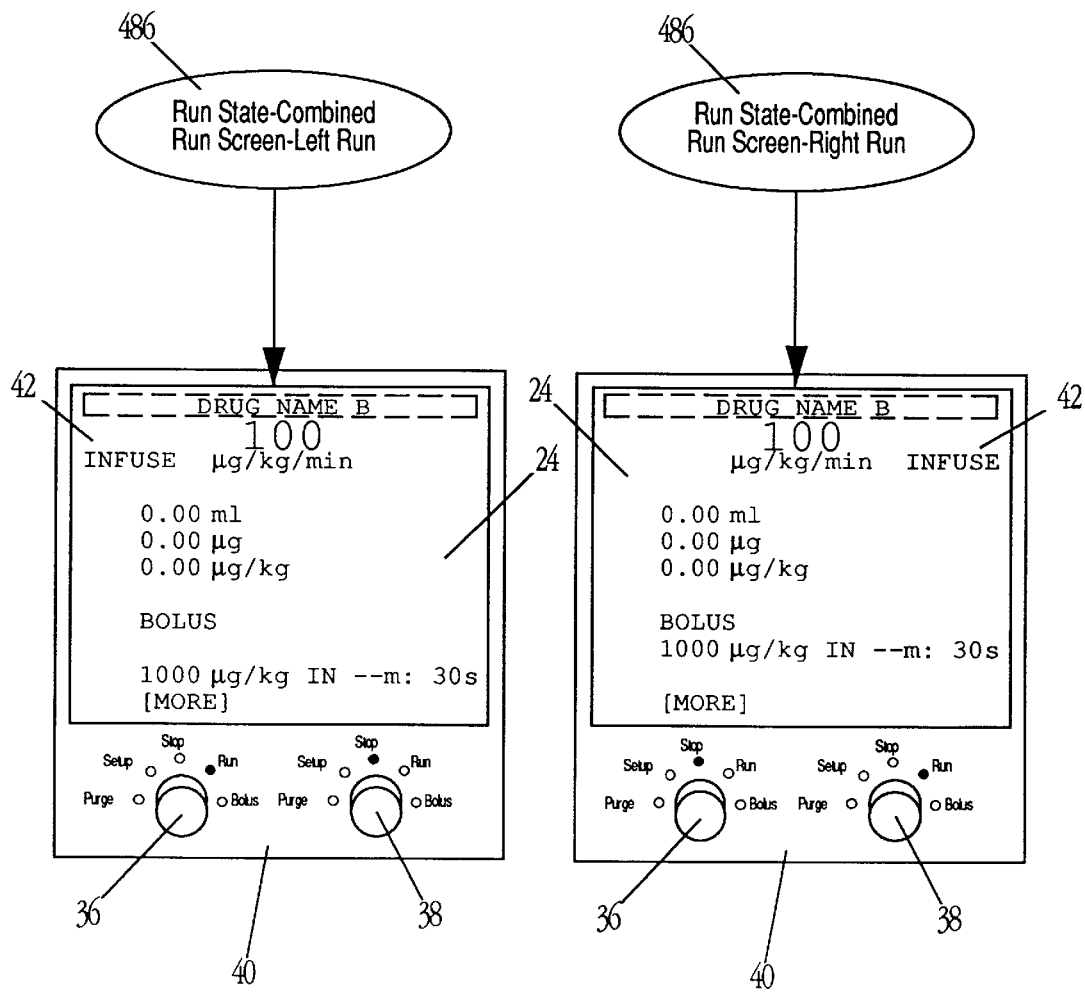

With reference now to FIGS. 39 and 40, in a further alternative embodiment of the present invention, a user can also select a "SEQUENTIAL" mode from a screen 476 displayed only if information on a first Setup screen 204 for both pumps is identical (excluding syringe manufacturer and size), and if the user selects "[OK/NEXT]" or "[OK/RUN]" on both first Setup screens 204. The user is given the option of entering the "SEQUENTIAL" mode at this point. If the user selects "NO" using either data entry knob 30, 32, individual second Setup screens 206 are displayed. Note that the data entry knobs 30, 32 are not illustrated in FIG. 40 for the sake of clarity.

However, if the user selects "YES" with either data entry knob 30, 32, a combined second Setup screen 477, that is, a second Setup screen which fills the entire display 24, is displayed. Next, if the user turns the left function knob 36 clockwise, a combined Pre-Run screen similar to that previously discussed but filling the entire screen will be displayed with "START" on the left half of the display. Alternatively, if the user turns the right function knob 38 clockwise, the combined Pre-Run screen will again be displayed, but with "START" displayed on the right half of the display 24. Depressing the data entry knob 30, 32 of the respective pump (not illustrated in FIG. 40) causes a combined Run screen 486 to be displayed, and to begin infusion with that pump. FIG. 40 illustrates exemplary combined Run state screens for both left and right pumps. Note the state of the associated function selection knob state LED's 40 and the placement of "INFUSE" 42.

Therefore, the "SEQUENTIAL" mode enables a user to program both pumps for a sequential infusion of the same drug from one of the pumps, then the other, resulting in a continuous infusion from multiple syringes not limited by the capacity of any one syringe. Once a first syringe is emptied or nearly emptied of its contents, the first syringe pumping is ceased and a second syringe is pumped. A warning can be provided to the user that the transition between syringes has taken place, and that the first syringe can now be replaced. Once the second syringe is emptied or nearly emptied, the pump once again switches syringes. Alternatively, the pump can be programmed to empty the contents of the two syringes and stop. Any other number of syringes can be employed in order to infuse a required quantity.

A Y-junction or other connection known in the art is employed to enable the continuous pumping from multiple syringes. It is preferred that the junction have check-valves to prevent flow back into the unused channel during replacement of an empty syringe.

During the execution of the "SEQUENTIAL" mode, the display can provide one undivided screen of information relating to the infusion under progress as an alternative to the split screen of the previously described modes. Such information can include a summary of the history of the current infusion, as well as information regarding the active pump such as the quantity remaining in the installed syringe, and the status of the currently inactive pump.

Bolus

In the Bolus state, a fixed amount of drug is delivered over an indicated time. If a Drug Library is installed in the pump and if the recommended Bolus Amount and Bolus Duration are specified in the Drug Library for the desired drug, the pump will display those default values to simplify data entry. The user may change both the Bolus Amount and the Bolus Duration to other values as desired. Minimum/maximum recommended Bolus Amounts and/or minimum/maximum recommended Bolus Rates are used by the pump to provide a library range warning 502 if the user enters values outside these windows.

Figure 37:
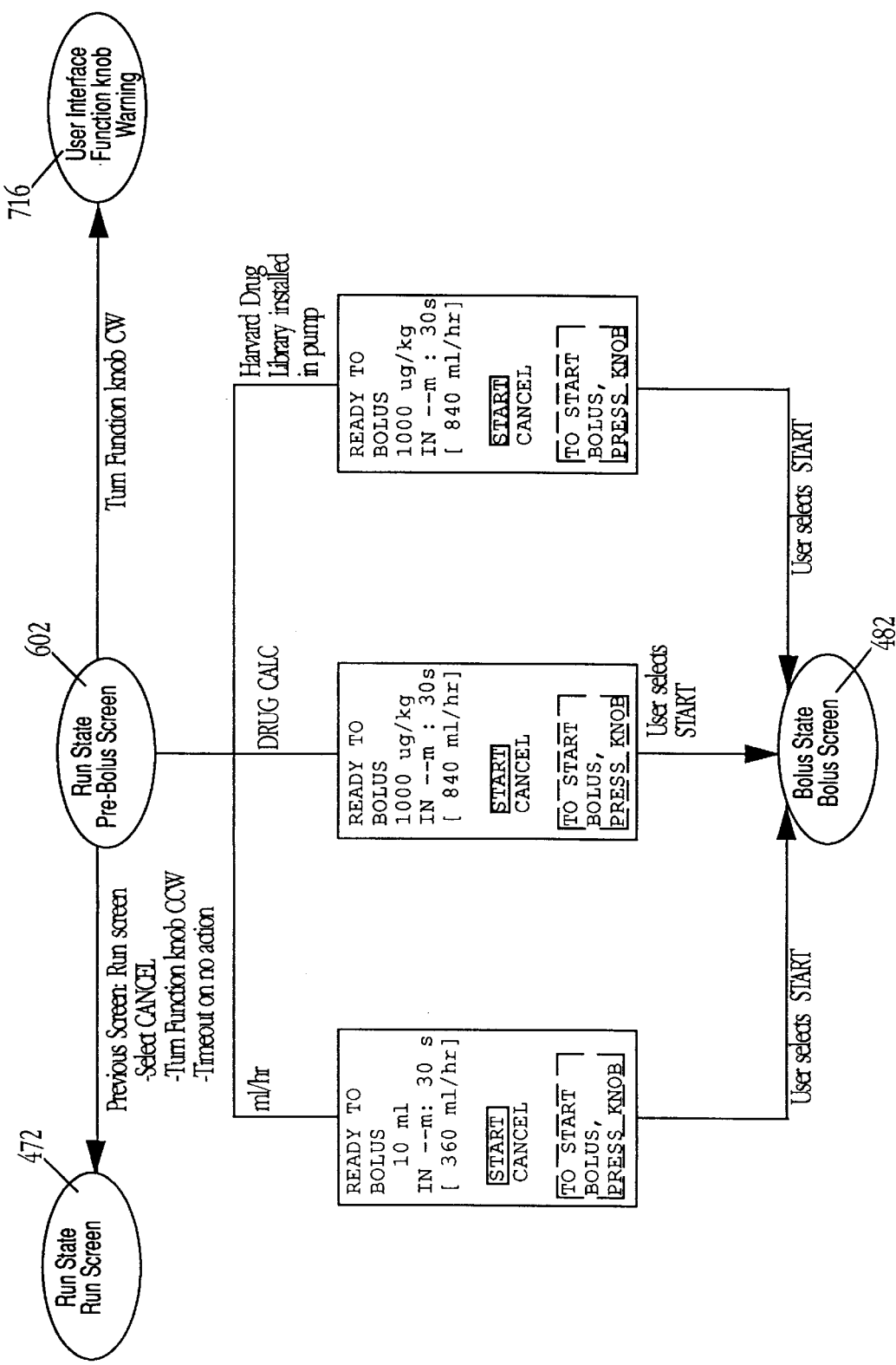

The Bolus state is accessed from either the Stop state (FIG. 33) or the Run state (FIG. 37). With reference to both, a Pre-Bolus screen 480, 602 is displayed with an option such as "START" highlighted once the function knob has been turned toward the Bolus LED. The Bolus state can only be entered from the Run or Stop states; the user can cancel entry into the Bolus state by selecting the "CANCEL" option from the Pre-Bolus screen, by turning the function knob toward the Run or Stop LED's or by waiting for a timeout to occur, thus returning the pump to the Run screen 472 or Pre-Run screen 470.

Figure 33:
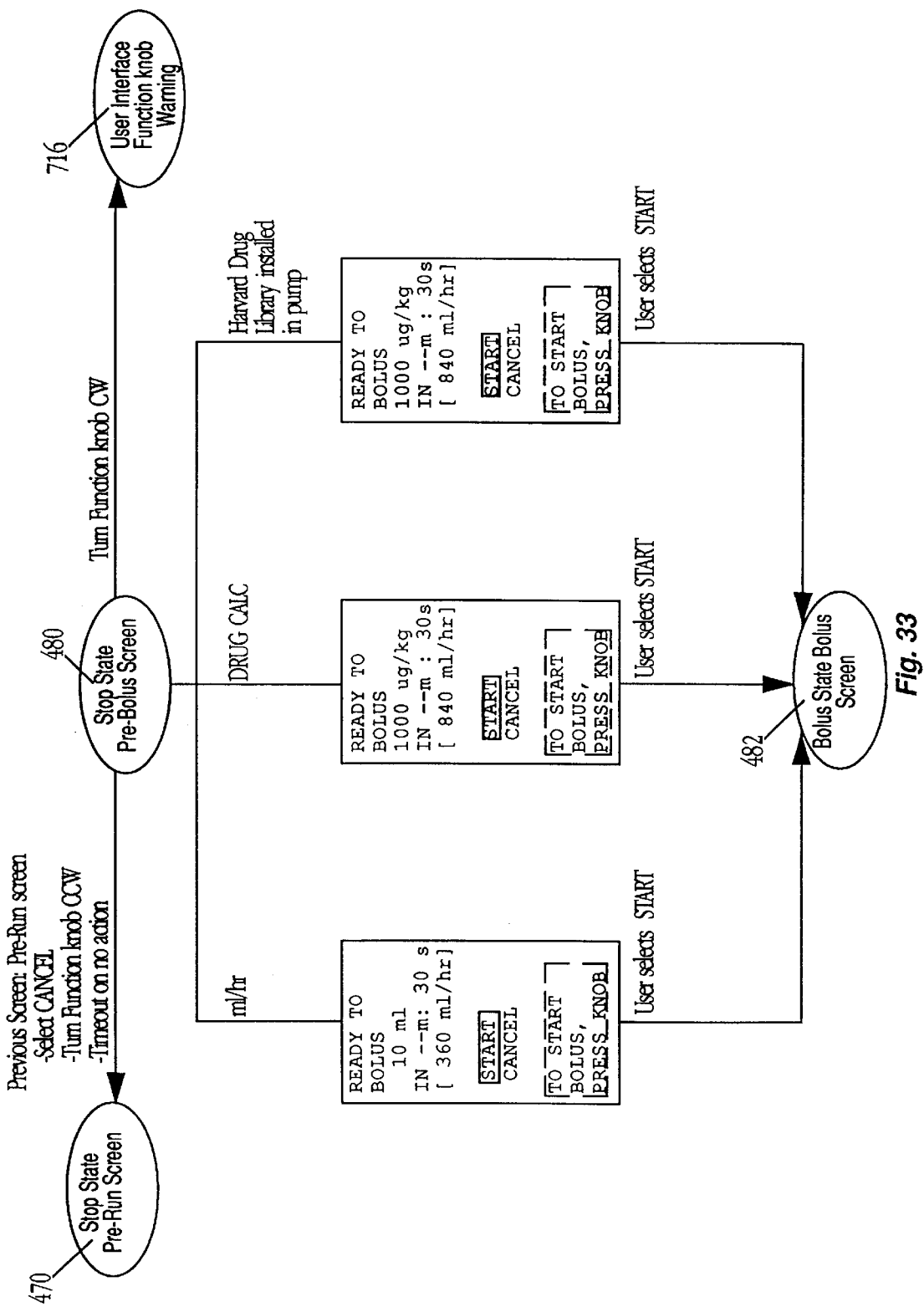

Exemplary Pre-Bolus screens are illustrated in FIGS. 33 and 37. In each case, the preselected Bolus parameters are displayed. At this juncture, the user only has the option of exiting the Bolus state as described above, or of starting the Bolus; Bolus parameters cannot be altered from the Pre-Bolus screen.

Figure 41:
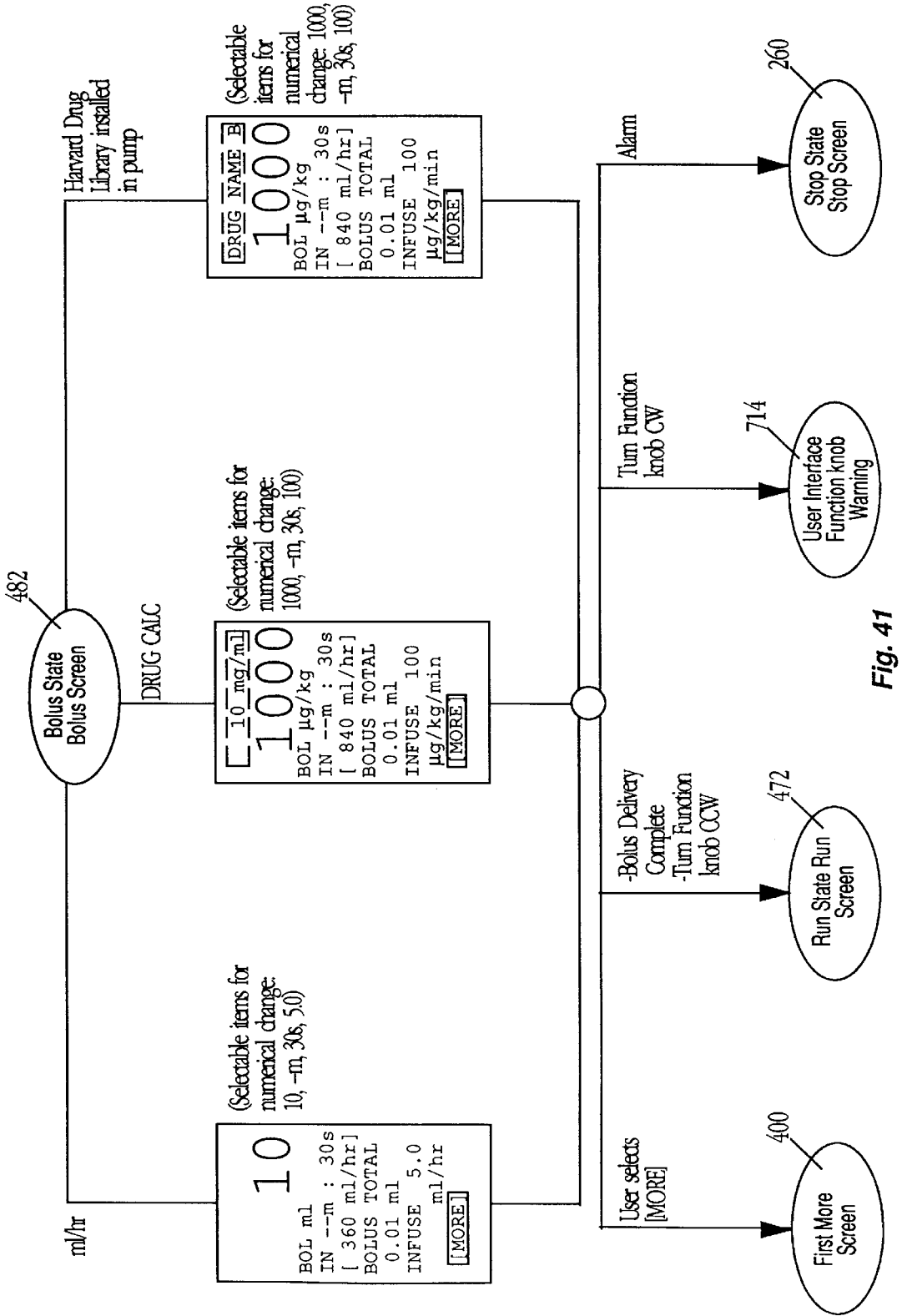
FIG. 41 provides exemplary Bolus state display screens for the pump of FIG. 14.

Pushing the data entry knob when "START" is highlighted begins the Bolus and invokes a Bolus screen 482, illustrated in FIG. 41. The information provided in the Pre-Bolus screen 480 is displayed, in addition to running totals for the bolus delivered and the infusion information. In contrast to the Pre-Bolus screen 480, Bolus amount and duration can be changed from the Bolus screen 482 using the data entry knob by highlighting the desired item, dialing up the desired quantity, and selecting the change.

The Bolus delivery can also be interrupted prematurely, completely stopping the infusion or continuing with the programmed continuous infusion. To transition to the Run or Stop states, the function knob is turned counterclockwise until the appropriate LED is lighted, thus stopping the Bolus. Further, the user can alter other information in the More screens by selecting the "[MORE]" option from the Bolus screen 482.

The pump automatically returns to the Run state 472 and automatically lights the Run LED after the Bolus Amount is delivered, thus infusing the drug at the specified rate. If it is desired that the pump stop after infusing a Bolus Amount, the rate for the pump should be set to zero. If an alarm is encountered during the Bolus infusion, the pump automatically transitions to the Stop state and the alarm condition is indicated.

More

Figure 42:
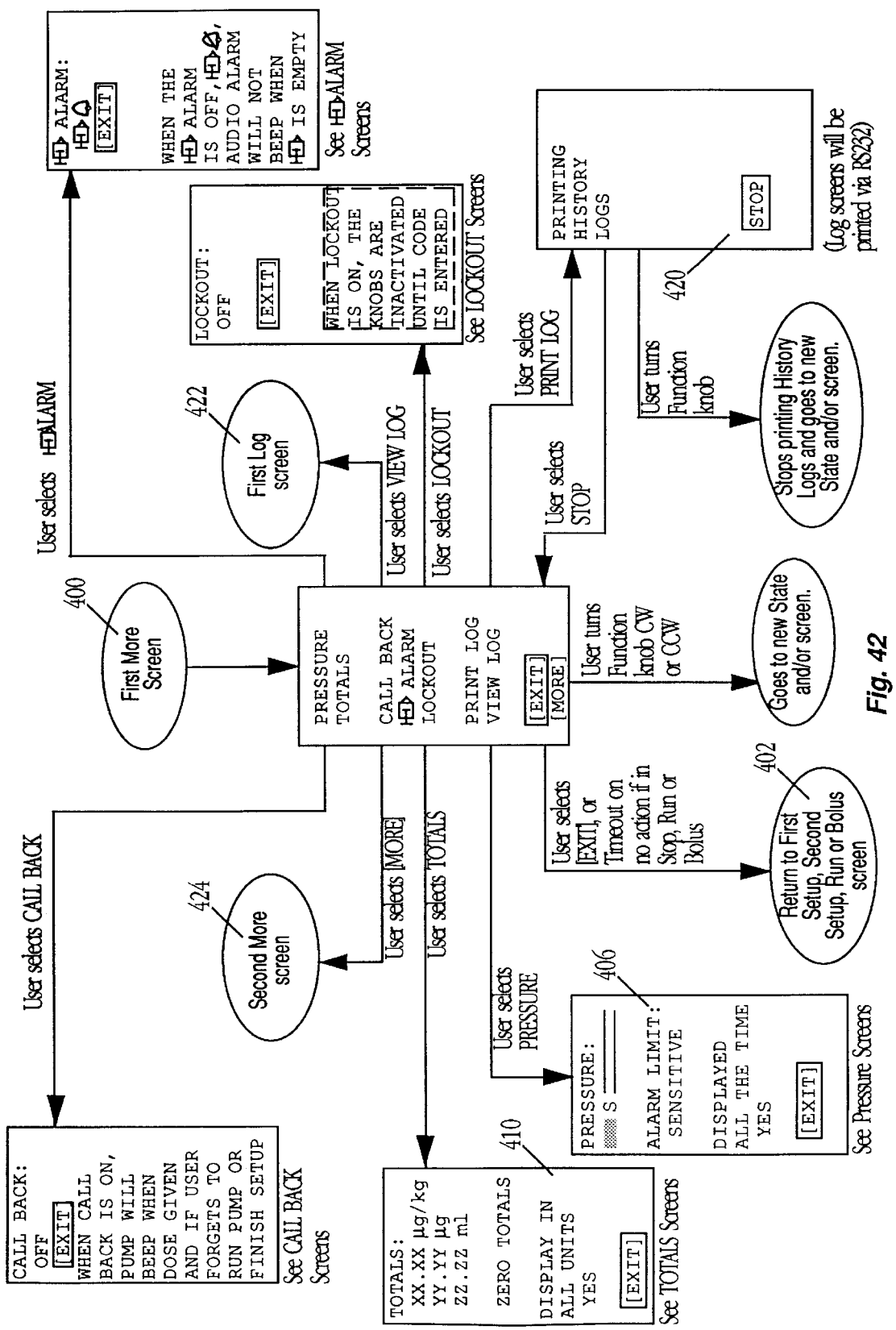
FIG. 42 provides exemplary display screens in flow charts depicting pump environment definition in the pump of FIG. 14.
Figure 43:
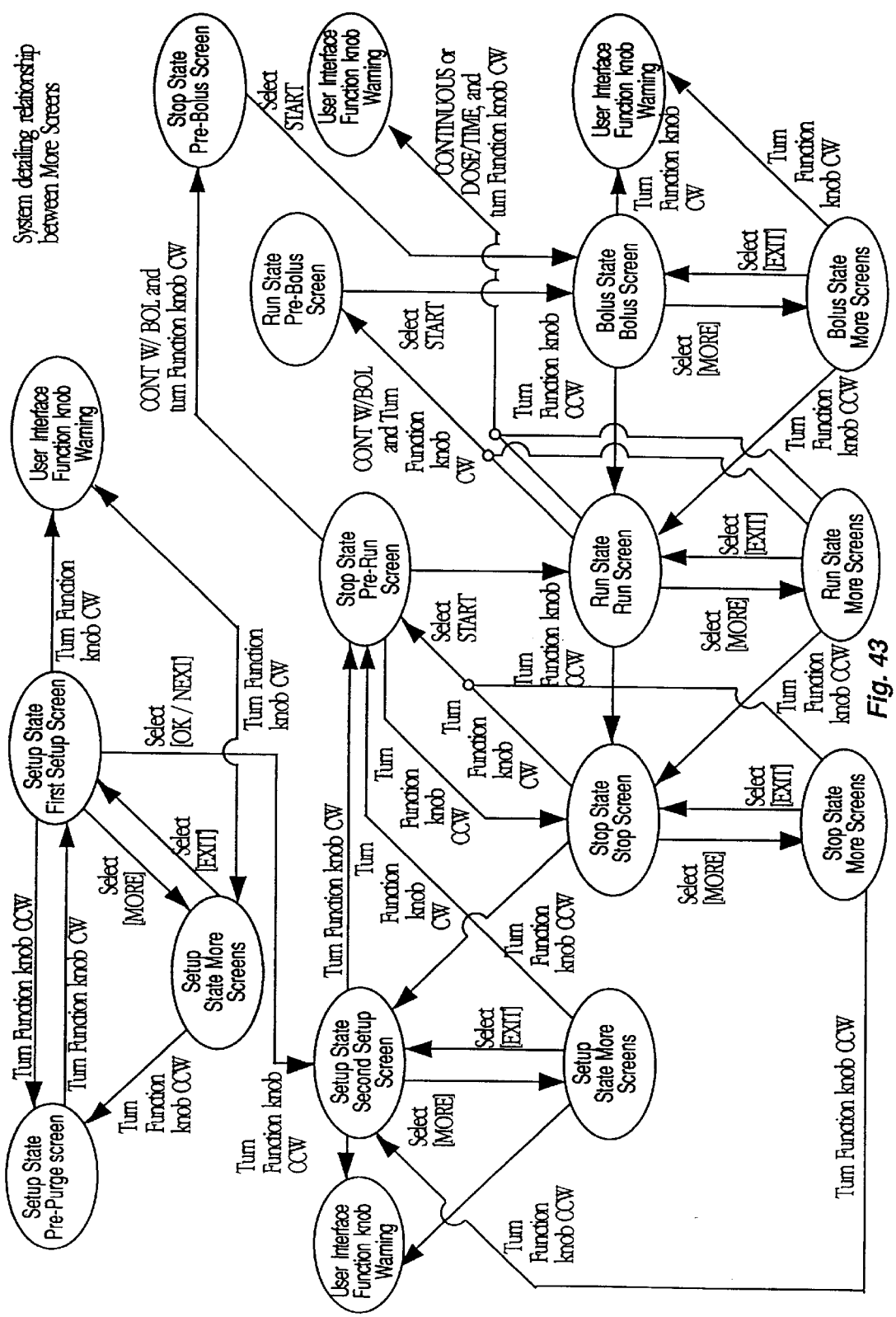
FIG. 43 is a flow chart depicting further state relationships in the pump of FIG. 14.

In FIG. 42, an exemplary first More screen 400 is displayed, along with the options available therein. First, if the user has inadvertently selected the first More screen 400, the "[EXIT]" option can be selected to return to the previous state or the user can do nothing and wait for a timeout 402 to cause the pump to return to the previous state. The user can also turn the function knob, which will cause the pump to transition to the new state and/or screen as illustrated in FIG. 43.

Figure 44:
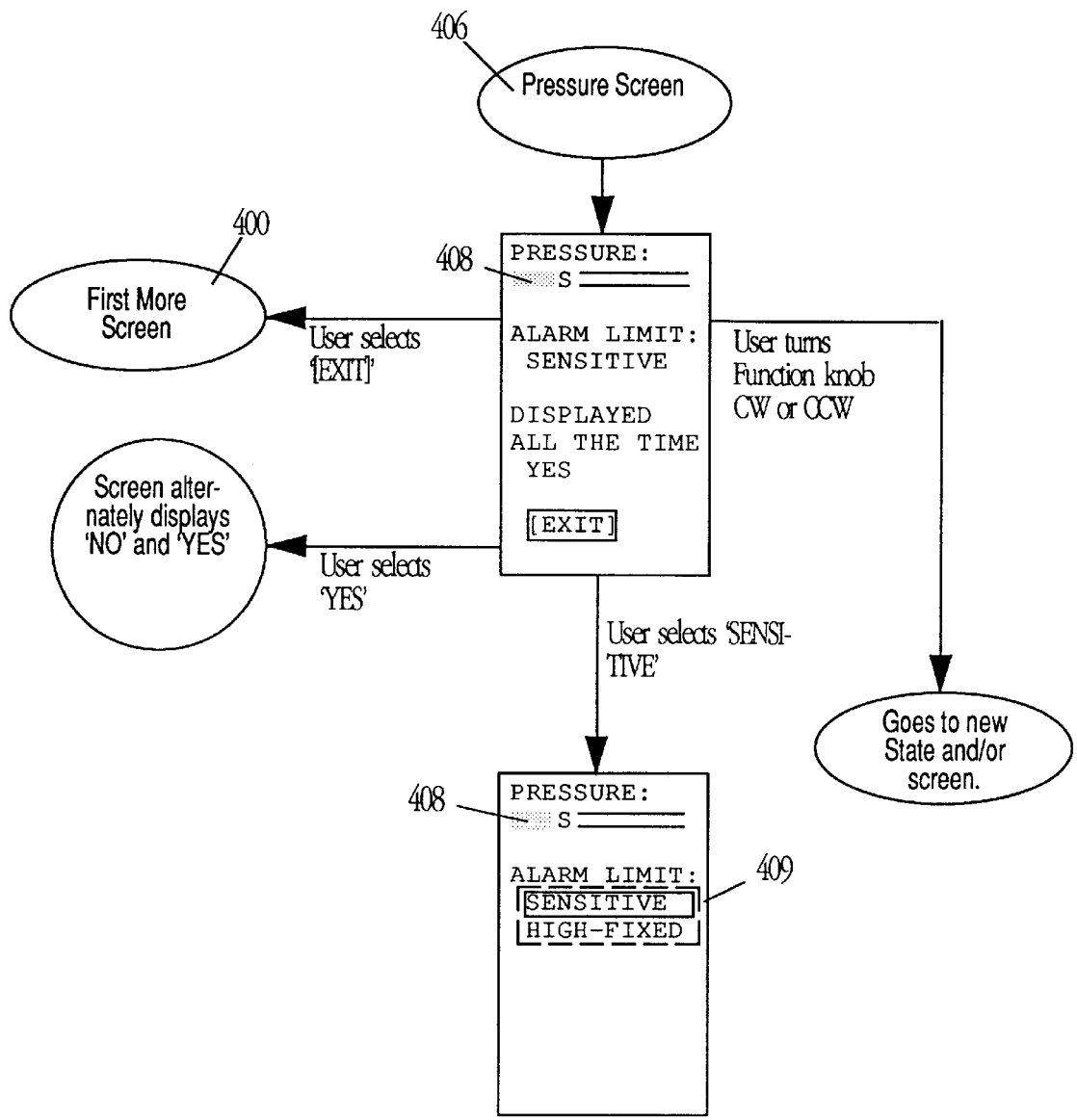
FIGS. 44–49 provide exemplary display screens in flow charts depicting pump environment definition in the pump of FIG. 14.

One feature which can be displayed from the first More screen is the Pressure alarm limit. The purpose of this alarm is to provide an indication to the user that an event such as an occlusion has occurred and that the infusion may not be executing as intended. By turning the data entry knob until "PRESSURE" is highlighted, then pressing the same knob to select the option, the Pressure screen 406 will be displayed, as further illustrated in FIG. 44.

Two alarm limits are available to the user, Sensitive and High-Fixed, each selectable from a menu 409. Once selected, the corresponding letter (S, H) on the pressure indicator 408 is highlighted. In this indicator 408, pressure in the infusion system is represented by a bar graph. As pressure builds from zero, the bar graph will illuminate from the left in the illustrated indicator 408. The Sensitive alarm setting increases the sensitivity of the pump in detecting an occlusion and decreases the time it takes the pump to alarm at rates less than 50 ml/hr. Other limits are employable in alternative embodiments. If a Sensitive pressure alarm has been selected, the pump will automatically adjust the pressure alarm limit to be just above the measured pressure and will display a highlighted 'S'. If a High-Fixed pressure alarm has been selected, the 'H' is highlighted, and when the pressure is at or above the High-Fixed limit, the alarm will become active. The user further has the option of having the pressure indicator illustrated on the last line at the bottom of the display continuously. The Pressure screen is exited by selecting the "[EXIT]" option. Alternatively, the user can turn the function knob to transition to the new state and/or new screen, as in FIG. 43.

Figure 45:
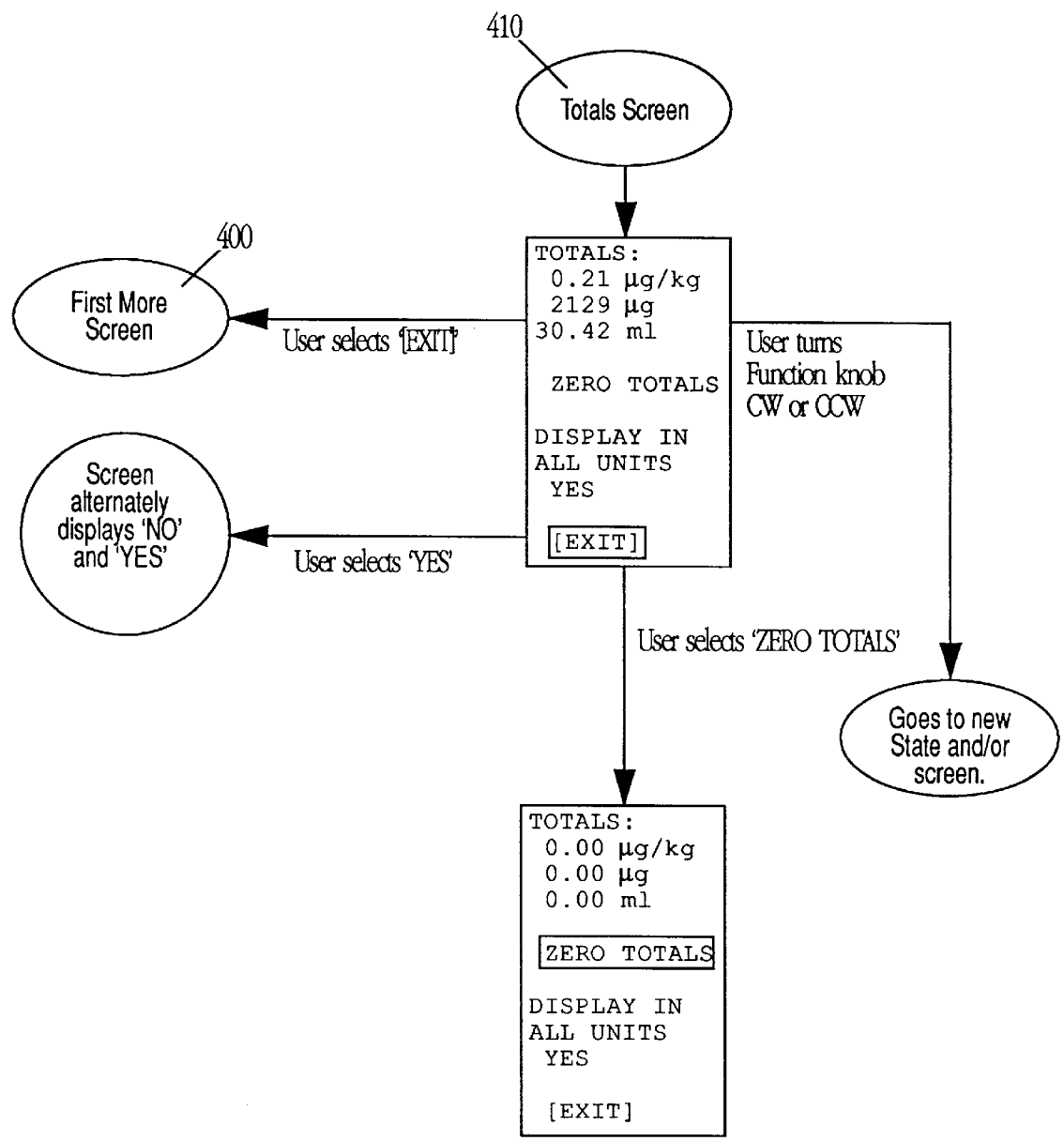

The user has the ability to zero the running infusion totals by selecting the "TOTALS" option from the first More screen 400, bringing up the Totals screen 410 as further illustrated in FIG. 45. The user can either zero the infusion totals by selecting the "ZERO TOTALS" option, display the totals in all available units on the Stop or Run screens by entering "YES" or can return to the first More screen by selecting "[EXIT]".

Figure 46:
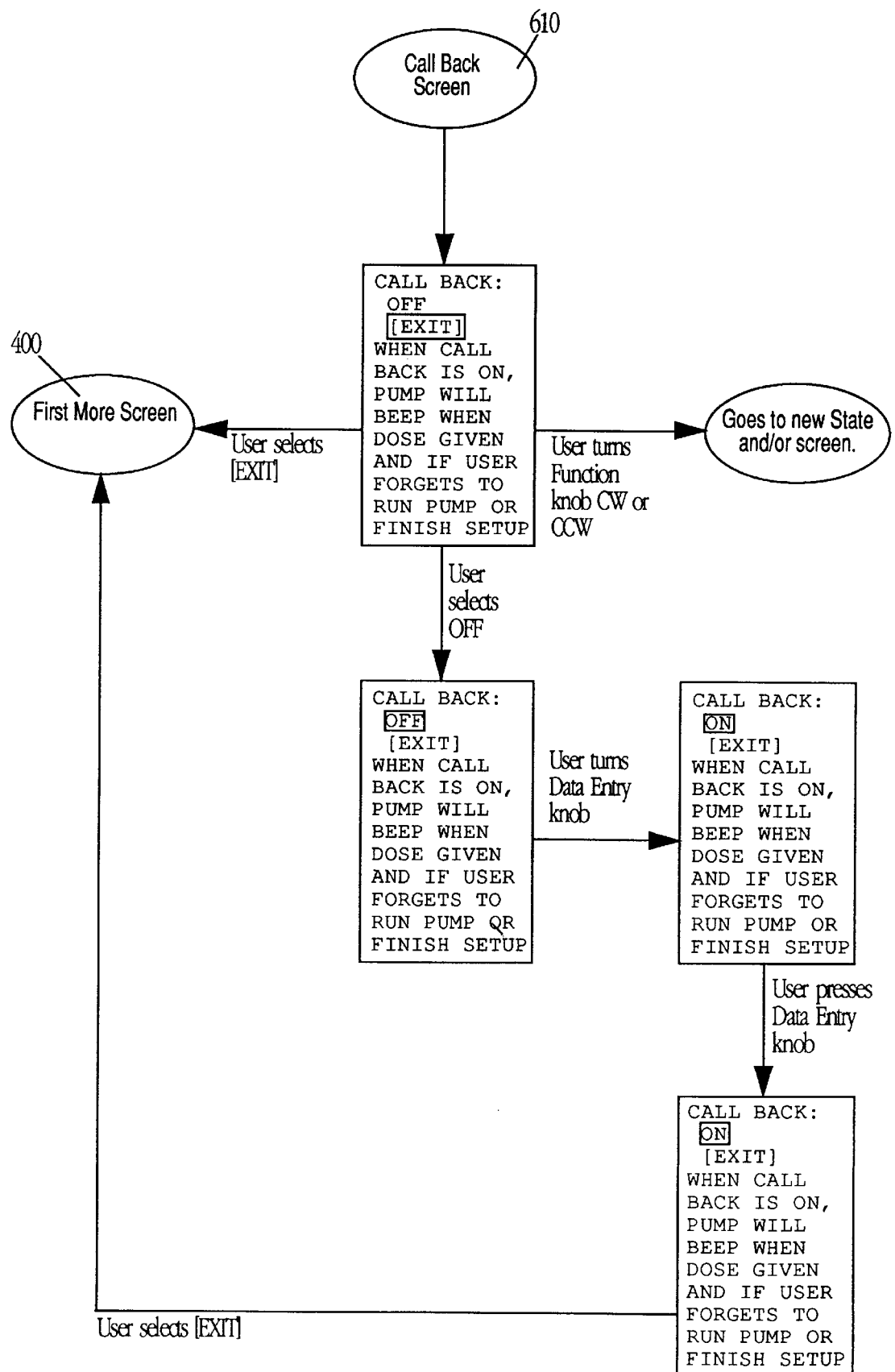

A "CALL BACK" option can be set to on or off by selecting "CALL BACK" from the first More screen to display the Call Back screen 610 as illustrated in FIG. 46. When "CALL BACK" is on, a Second Degree Warning as shown in FIG. 61 will occur when the user doesn't enter all of the setup information and the pump is inactive for 1 minute; the user enters all of the setup information but does not start the infusion or bolus after 1 minute has elapsed or the mode is "DOSE/TIME" and the pump has finished the delivery of a Dose.

Figure 47:
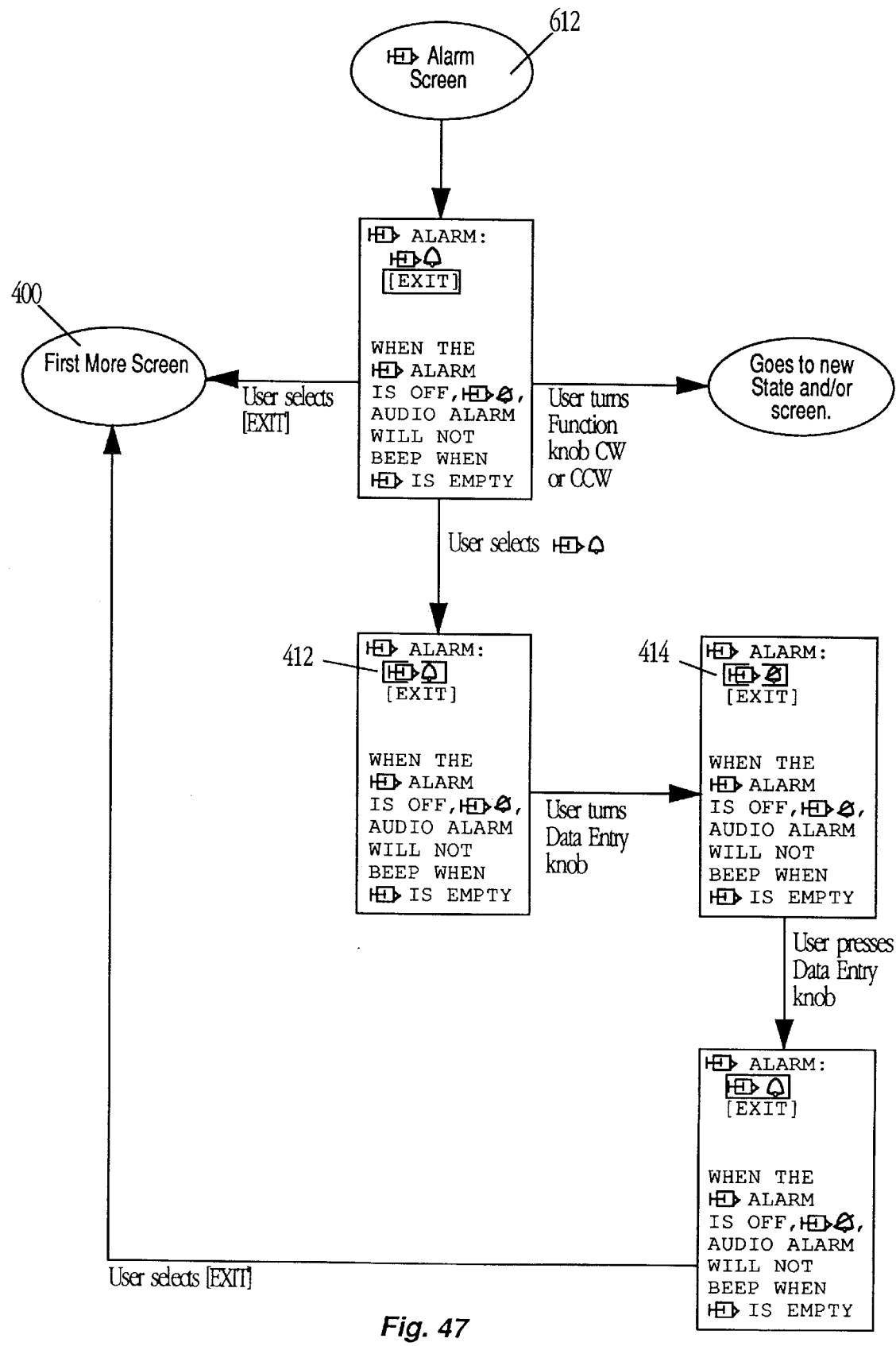
Figure 60:
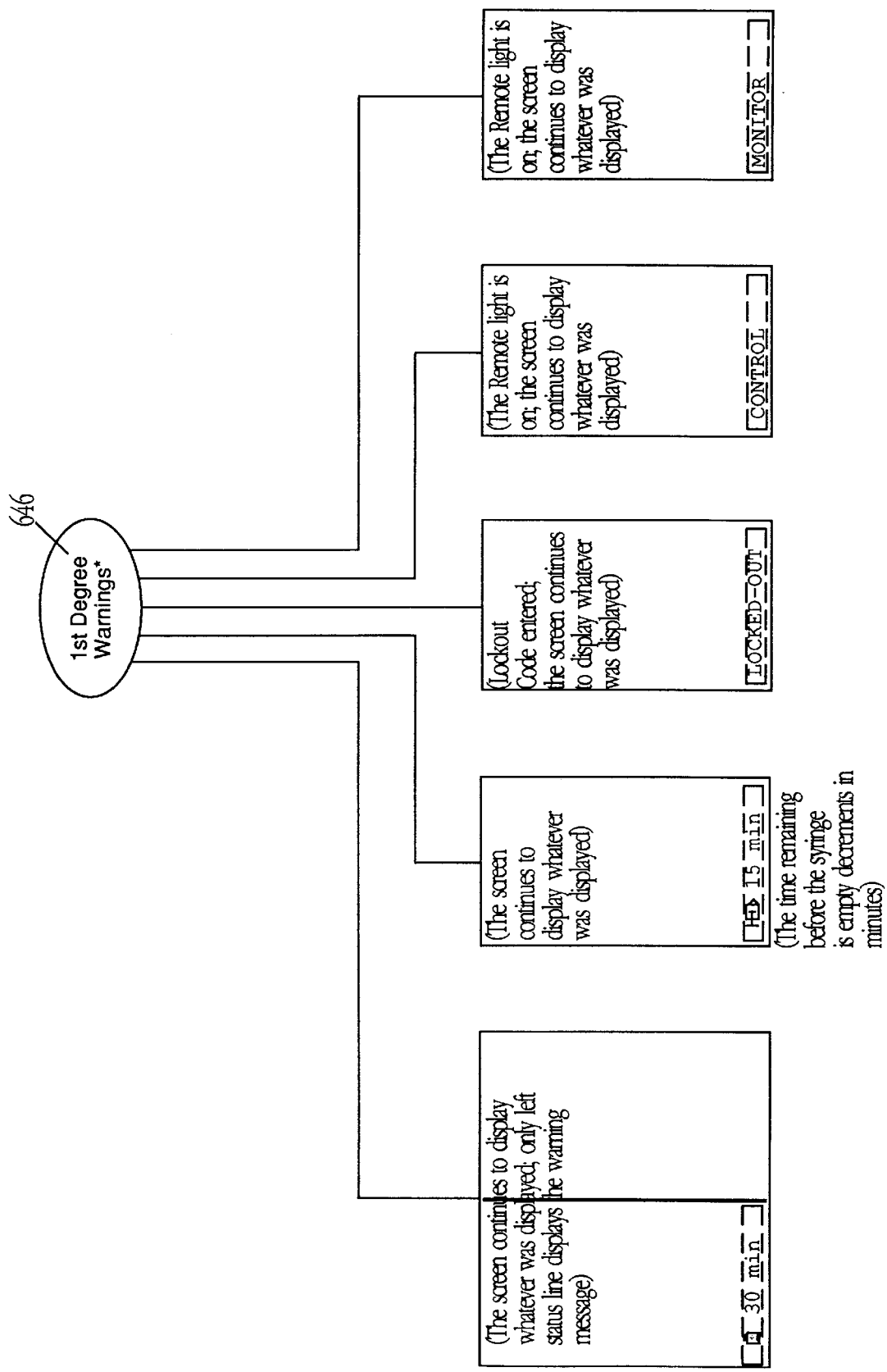
Figure 61:
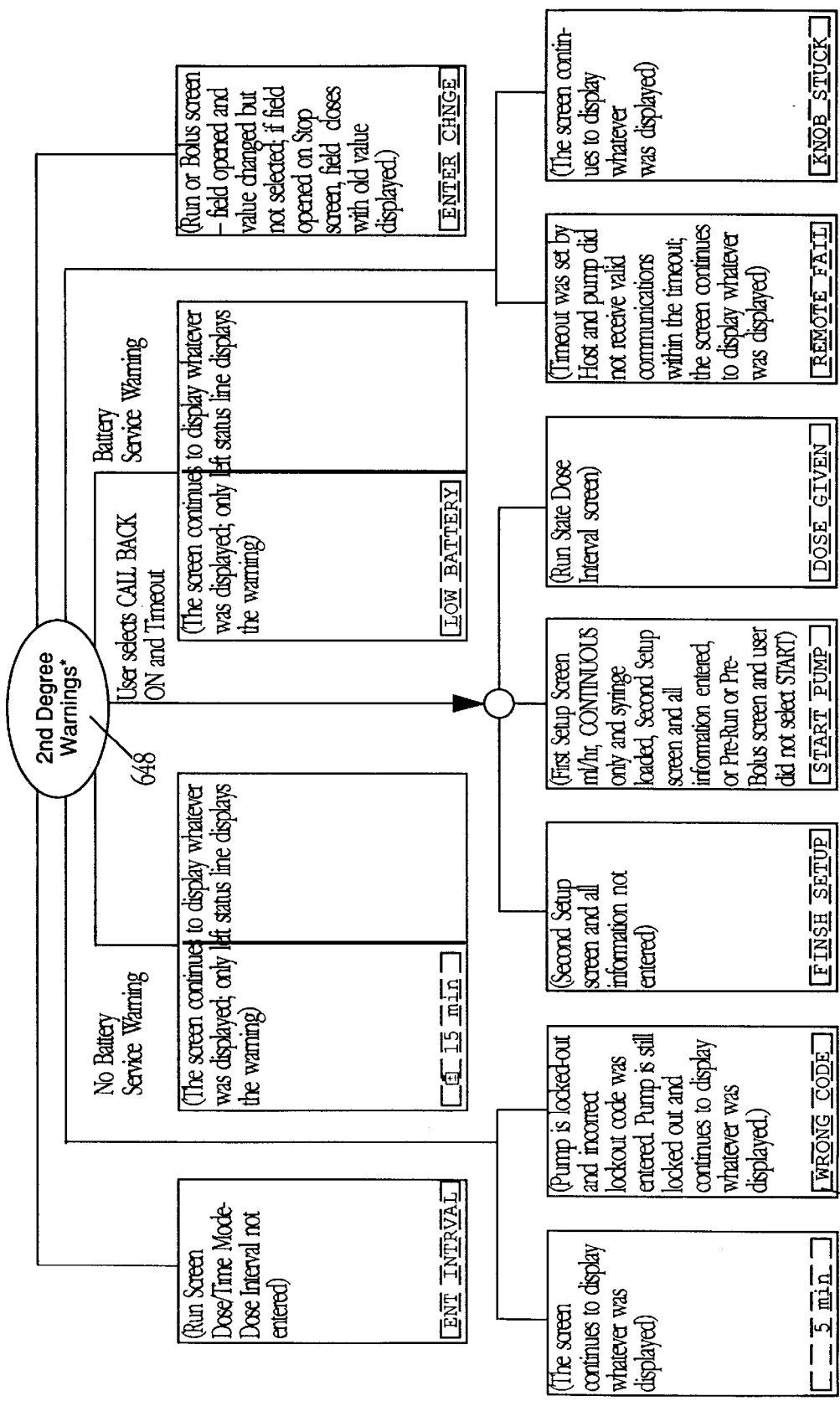
Figure 62:
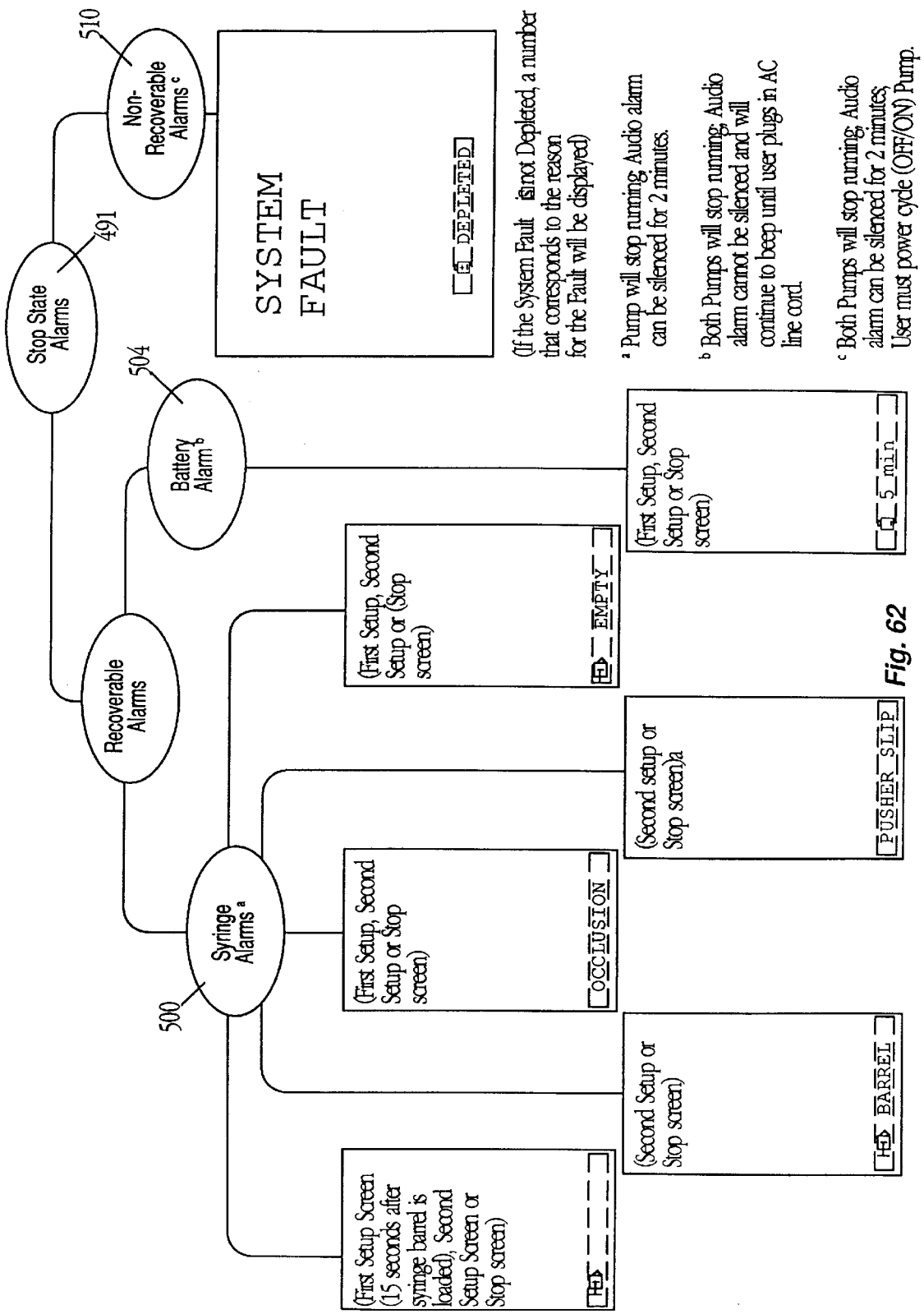
FIG. 62 illustrates various types of alarms and associated display screens provided by the pump of FIG. 14.

The audible alarms for the "Syringe 15 minutes", "Syringe 5 minutes" and "Syringe Empty" warnings and alarms as in FIGS. 60 through 62 can be enabled or disabled from the first More screen 400 by turning the data entry knob to highlight "SYRINGE ALARM" and depressing the knob to display the Syringe Alarm screen 612, as further illustrated in FIG. 47. Then, turning the data entry knob toggles between a syringe and alarm bell symbol 412 and a syringe and alarm bell symbol having a diagonal line there through 414, indicating no audible alarm. The data entry knob is depressed again to make the selection.

Figure 48:
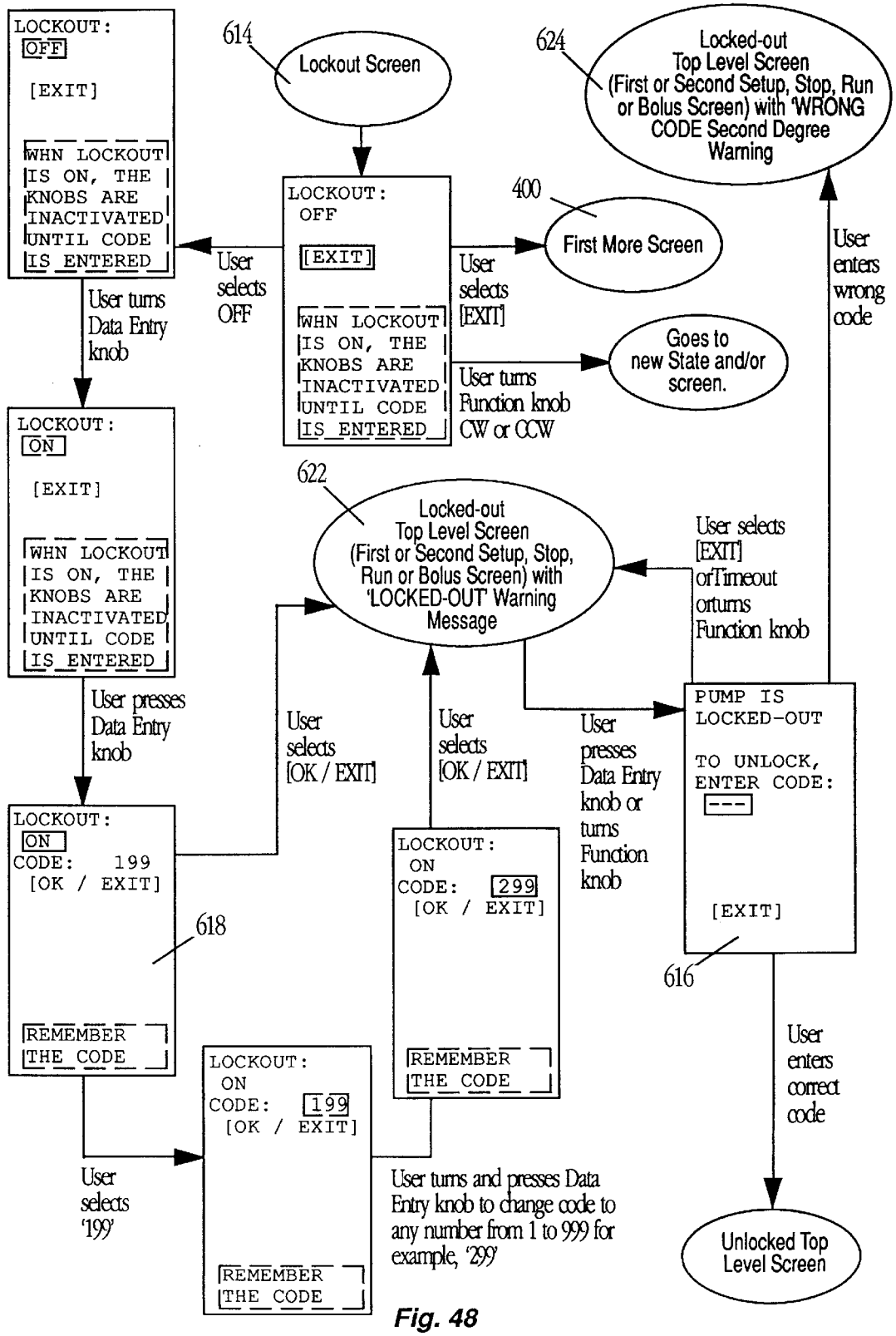

A "LOCKOUT" option can be set to ON or OFF by selecting "LOCKOUT" from the First More screen to display the Lockout screen 614 illustrated in FIG. 48.

When the "LOCKOUT" option is ON, the data entry and function knobs can not be used without the pump prompting the user to enter the lockout code 616, thus preventing non-medical personnel from tampering with the pump.

When the user selects ON 618, the 3-digit lockout code that was last entered will be displayed. If this code is fixed on the Lockout Diagnostics screen 620 illustrated in FIG. 50, the code cannot be changed. If this code is not fixed, it can be changed by the user. When the user selects "[OK/EXIT]" the pump is "locked-out" and displays the top-level screen 622.

If the correct code is not entered the Second Degree Warning (Wrong Code) 626 illustrated in FIG. 61 will be displayed and the pump will still be locked out and will return to the top level screen 624. Each pump can be separately locked out.

As in FIG. 42, each pump maintains a history log indicating how the pump was programmed, what states were transitioned between, and what warnings or alarms were encountered. This log 422 is accessed through the first More screen 400, and is discussed in further detail below. The history log is printed (and a screen 420 is displayed indicating this) via the RS-232 interface by selection of the "PRINT LOG" option from the first More screen 400.

Figure 49:
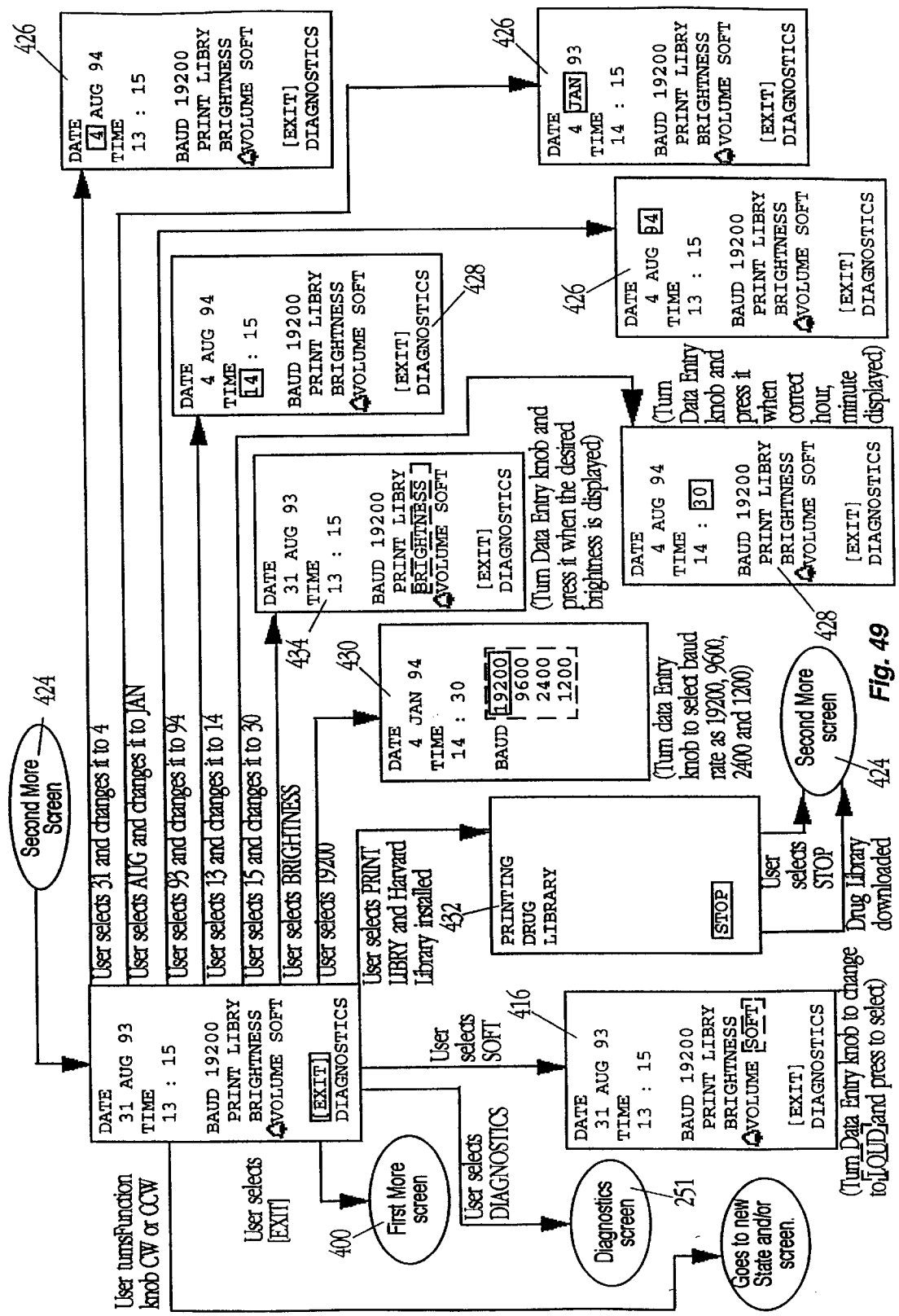

A second More screen 424, illustrated in FIG. 49, is invoked by user selection of the [MORE] option on the first More screen 400. As indicated in this figure, the user turns the data entry knob to adjust the entries for the date 426 and time 428. The desired baud rate is selected 430 from a menu of rates.

The Drug Library, discussed below, can be printed 432 from the second More screen via the RS-232 port. During the printing process, the user is provided with the opportunity to stop the print by selection of the "STOP" option.

The second More screen enables user manipulation of the screen brightness level 434. Once the "BRIGHTNESS" option has been selected, the data entry knob is turned until the desired brightness is achieved, then this knob is depressed.

The user can choose between a soft or loud audible alarm 416.

Figure 50:
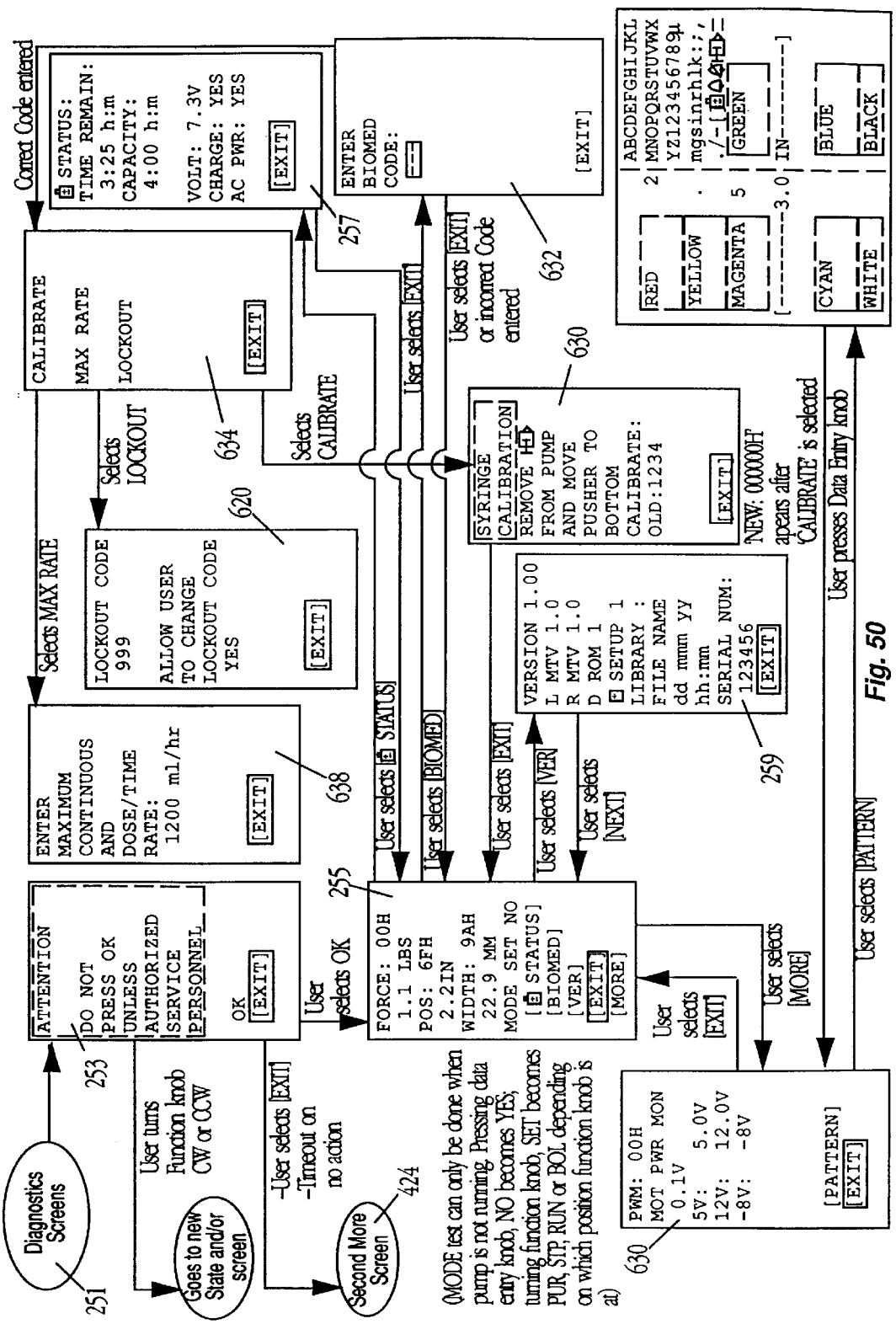
FIG. 50 provides exemplary display screens in a flow chart depicting diagnostic options in the pump of FIG. 14.
Figure 51:
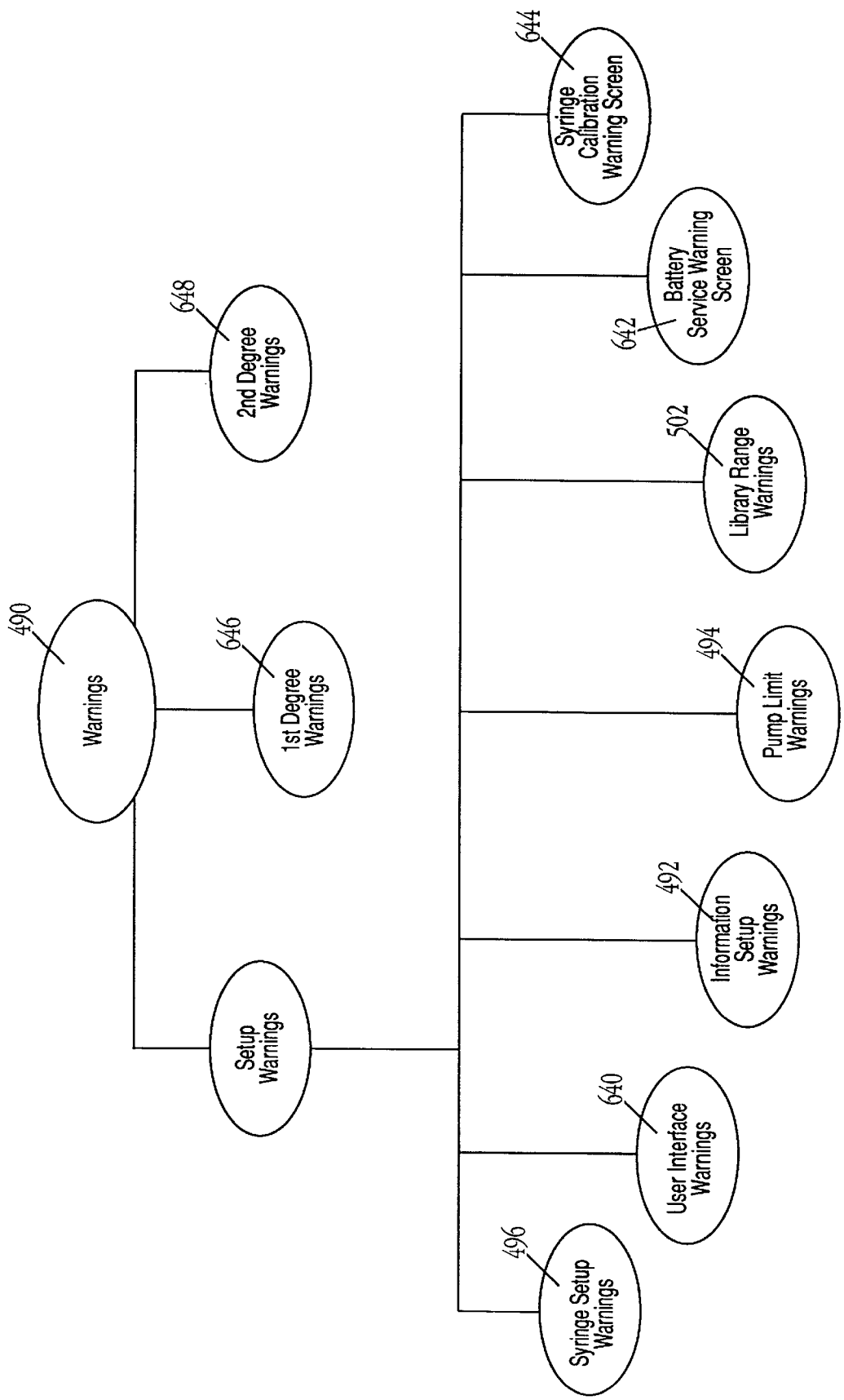
FIG. 51 illustrates various types of warnings provided by the pump of FIG. 14.

Diagnostic information and tests are available by selection of the "DIAGNOSTICS" option 251 on the second More screen 424, as shown in FIG. 50. Once selected, an initial authorization screen 253 is provided, giving someone other than service personnel an opportunity to return to the second More screen 424 by selecting the [EXIT] option. By selecting "OK", service personnel are provided with a first diagnostics screen 255 indicating current conditions measured by associated sensors, such as current force applied to a syringe plunger, and plunger position and width.

From the first diagnostics screen 255, service personnel can further access more detailed pump information, such as shown in a battery status screen 257 and a software version screen 259, and additional pump related information 630. Further, from the first diagnostics screen 255, the pump can test the data entry and function knobs 30, 32, 36, 38 as described in the mode test 255. Further, from the first diagnostics screen, authorized service personnel can select [BIOMED] and enter a biomed code 632 to perform additional options 634 such as calibrating the syringes 636, entering the maximum Continuous and Dose/Time rate 638 and entering a fixed lockout code 620. The pump is returned to the first More screen 400 by selecting [EXIT] from the first diagnostics screen 255.

Warnings and Alarms

In the pump of the present invention, warnings are all recoverable, whereas alarms are classified as either recoverable or non-recoverable. FIGS. 51 through 62 illustrate how information accumulated at various points results in warnings, what prompts are provided by the pump, and to what state the pump returns. Typically, warnings, which can be further classified according to severity, are either status messages (added to current screen or new screens) and may require only that the user acknowledge the warning by depression of the data entry knob, and can be displayed in yellow. With reference to FIGS. 51 through 61 examples of warnings 490 are: wrong syringe manufacturer or syringe not loaded properly (syringe setup warnings 496); user uses data entry or function knob incorrectly (user interface warnings 640); incomplete information being supplied (information setup warnings 492); requested rate exceeds pump rate (pump limit warning 494); entered data beyond stored library window (library range warning 502); battery capacity needs to be recalibrated (battery service warning 642); pump needs to be calibrated for syringes (syringe calibration warning 644); first degree warnings 646; and second degree warnings 648. In all second degree warnings, the audio alarm will sound continuously, though the alarm can be permanently silenced by pressing the data entry knob, except for "ENT INTRVAL".

With reference to FIG. 62, examples of alarms 491 are: syringe barrel not captured, syringe plunger not captured, pusher moved, occlusion and, syringe empty (syringe alarms 500); five minutes of battery remaining (battery alarm 504); and non-recoverable alarms 510. Exemplary alarm screens are found in FIG. 62, and can be displayed in red for visibility.

Non-recoverable alarms 510, such as battery depleted, are referred to a system faults. Recovery from these alarm conditions requires recycling the pump power and re-entry of information into the Setup mode screens 204, 206.

Serial Communications

Bidirectional Serial Communications via at least one RS-232 port enables the pump of the present invention to either be controlled by a computer or other external device, or to transfer information to such computer or other device for electronic record keeping upon prompt by the external device. In addition, the pump can print the history logs and drug library through an RS-232 port. The RS-232 port (or ports) in the control unit enables remote control from a computer initiated by a remote host device, with the pump acting only as a slave machine and the host providing all Setup information with the exception of the syringe, concentration and drug information. All communications are initiated by the external computer or host device, with the exception of pump to printer data.

Once the pump has received a message and is in communication with the computer or remote host device, the Remote LED is lit and will remain lit until the communication is interrupted. Once a user controls the pump locally by turning the data entry knob or function knob, remote pump control is interrupted. Syringe information such as concentration and drug information must be entered locally, or must be entered remotely and confirmed locally, despite the pump being remotely controlled.

If the pump is being monitored by a remote device, the word "MONITOR" will appear on the display. Similarly, if the pump is being controlled remotely by an external device, the word "REMOTE" will appear on the display.

Drug Library

A Drug Library for use with the pump of the present invention can contain up to 300 Drug Names and default information particular to each drug. Each Drug Name can be listed under one or more user-defined Types. The drug's default infusion information and recommended safety limits can be different under each Type. Exemplary types include: Analgesics, Antibiotics, Cardiovasc., Hypnotics, ICU Meds, MUSC Relax. Alternatively, the types may be user-defined by hospital area, e.g. NICU, OR, clinician name, or any other desired grouping. Typical default information for infused drugs can include: up to three default concentrations; default infusion rate and units; minimum and/or maximum recommended infusion rates; default Bolus Amount, Duration and units; minimum and/or maximum recommended Bolus rates; minimum and/or maximum recommended Bolus Amounts; and default and minimum and/ or maximum recommended Dose Amounts, Dose Rate, Number of Doses, and Dose Interval.

Figure 63:
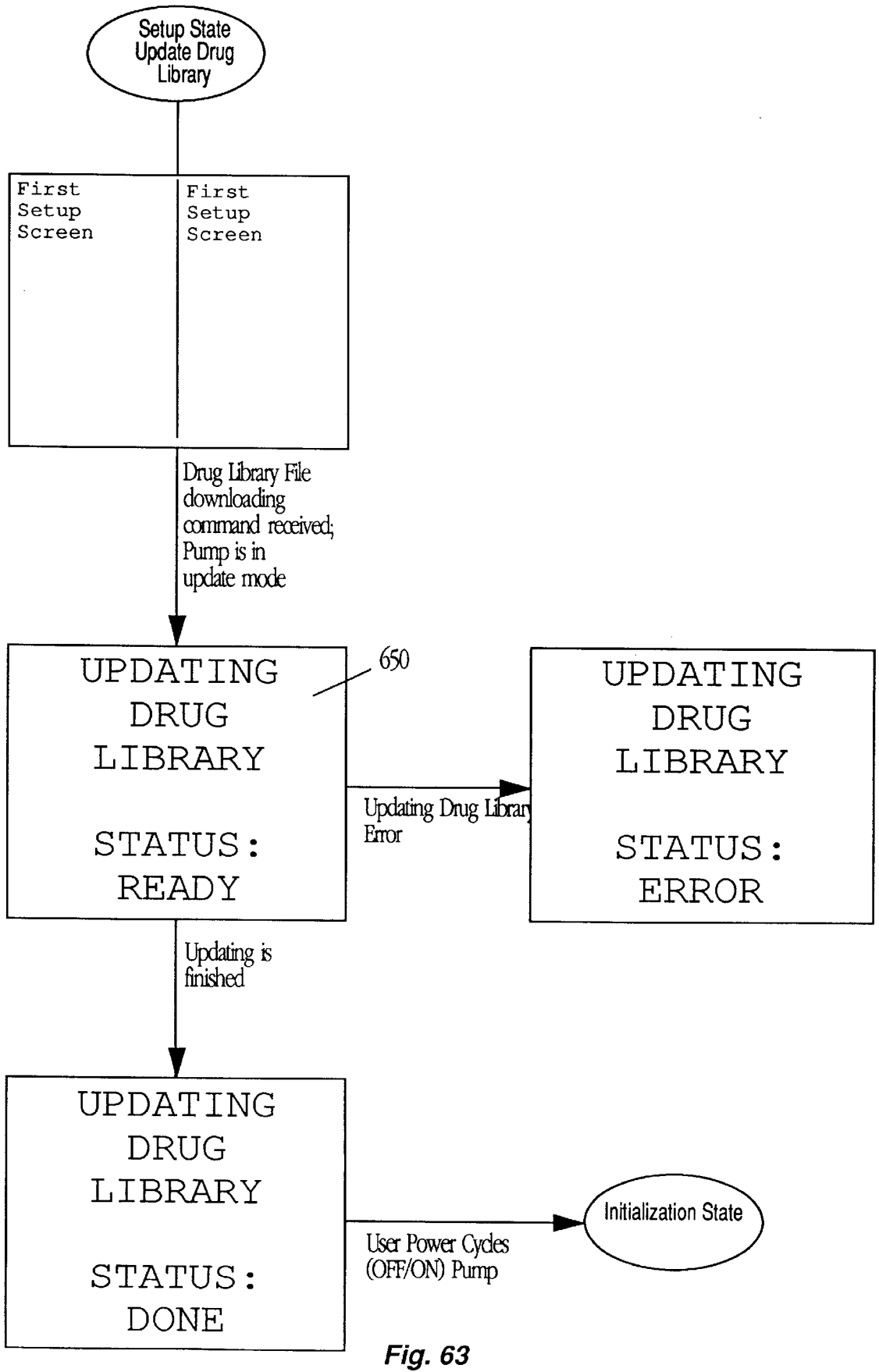
FIG. 63 provides exemplary Drug Library updating display screens provided for the pump of FIG. 14.

In addition to the option of providing the pump with a Drug Library already loaded in pump memory, a program running on a personal computer can be used to create a custom Drug Library. Once complete, this customized library can be downloaded to the pump via the at least one RS-232 port found on the control unit. When the Drug Library is downloaded or updated when both pumps display the first Setup screen, the update drug library screen 650 will be displayed, as illustrated in FIG. 63.

Infusion Loa

Figure 64:
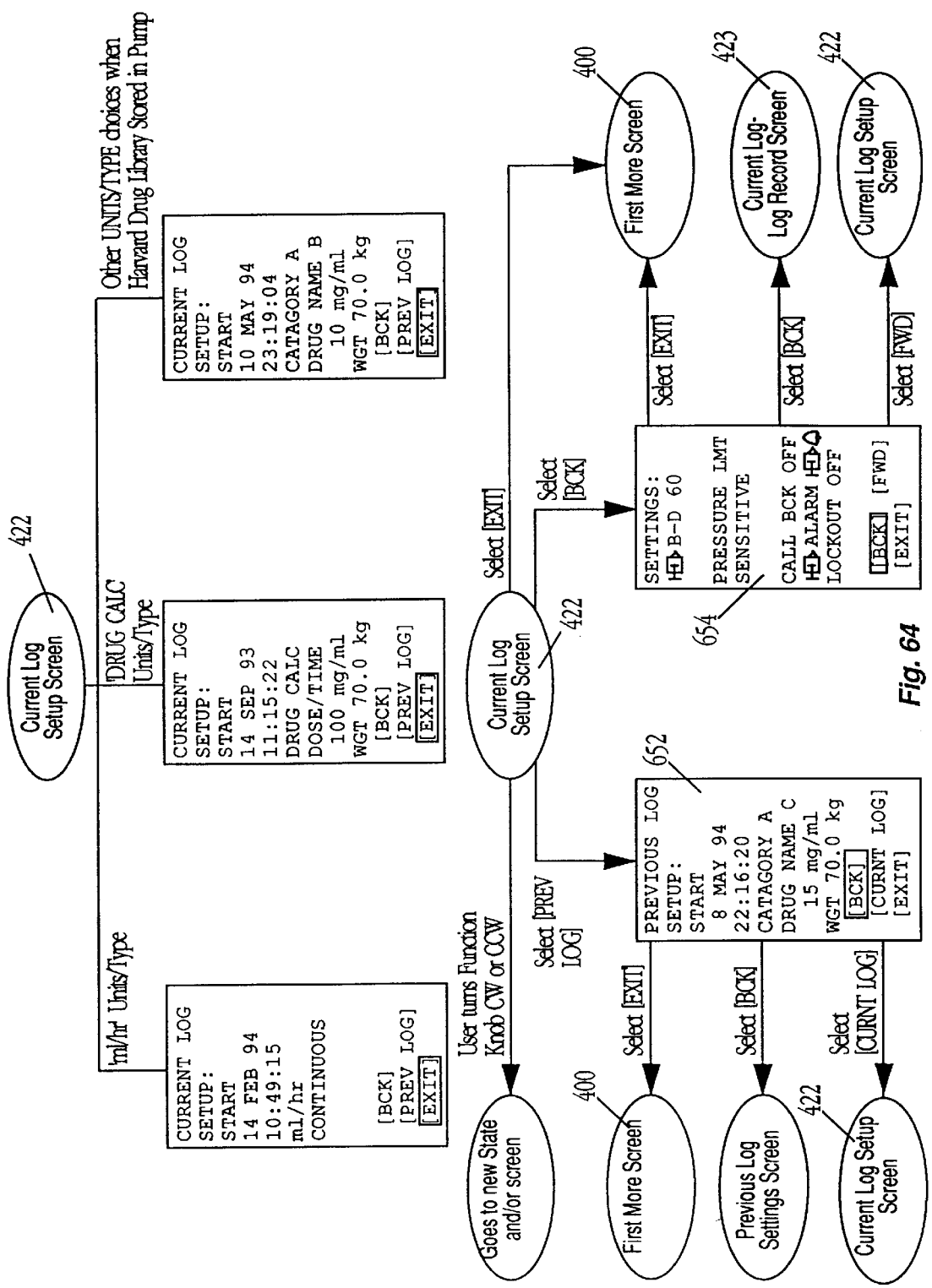
FIGS. 64 through 66 provide exemplary History Log displays for the pump of FIG. 14.

An Infusion Log stored within the device of the present invention provides the operational history of a respective pump contained therein with respect to the current and previous drugs infused. As illustrated in FIG. 64, information recorded within the Current Log Setup screen 422 includes setup information for the current log, including the start date and time, Units/Type, Mode or drug name, concentration, and patient weight. From this screen 422, the user can select [PREV LOG] to access the previous Log Setup screen 652, select [EXIT] to return to the first More screen 400, or select [BCK] to display the settings for the current log 654.

By selecting [BCK] from the Settings screen 654, a series of Log Record screens 423 will be displayed, each having the date, a time tag and a description of the event or occurrence. Alternatively, the date may only be displayed if it has changed from the previous entry. Such events or occurrences are divided into pages of screen displays. Each record consists of date, time and event information.

Figure 65:
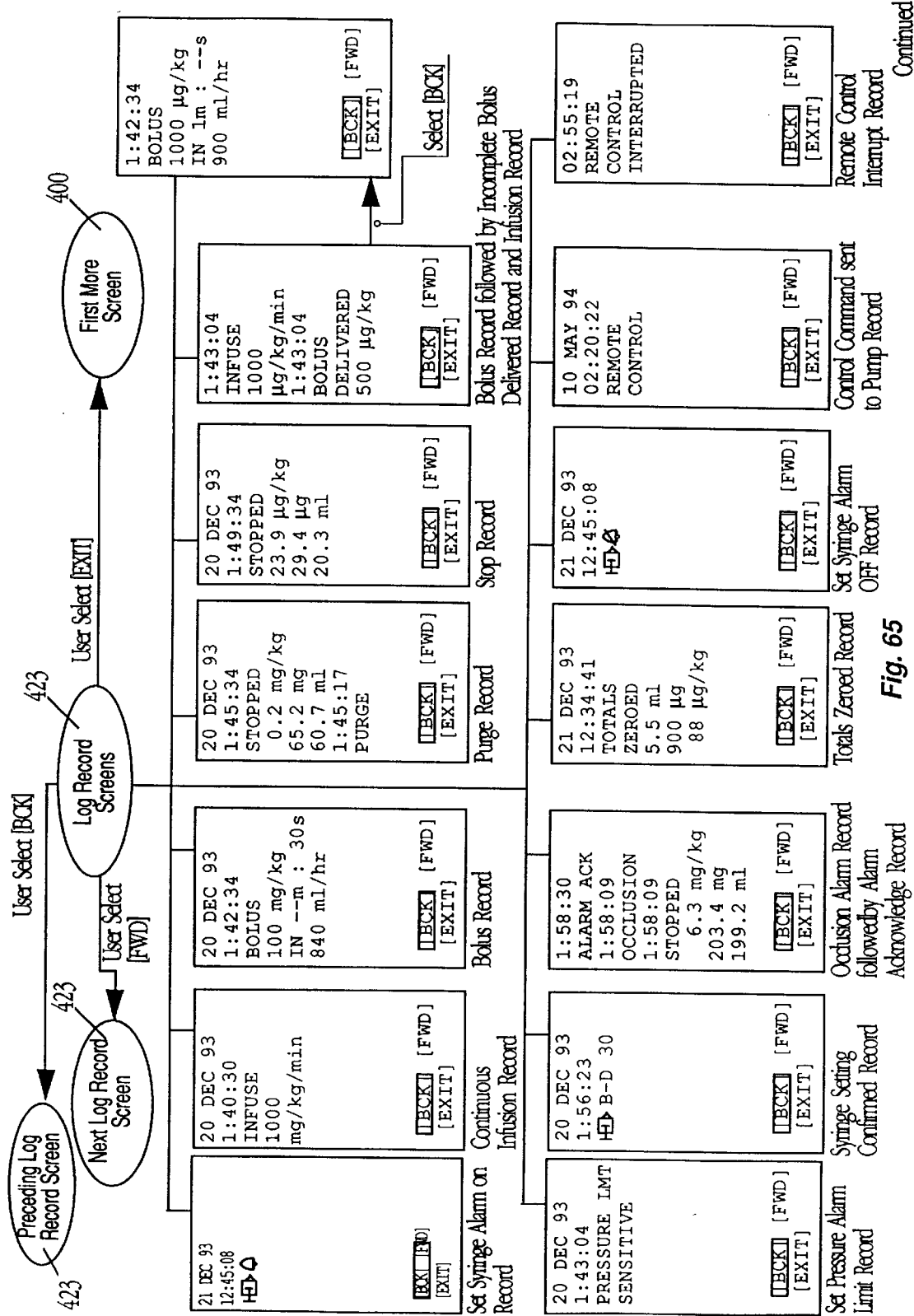
Figure 66:
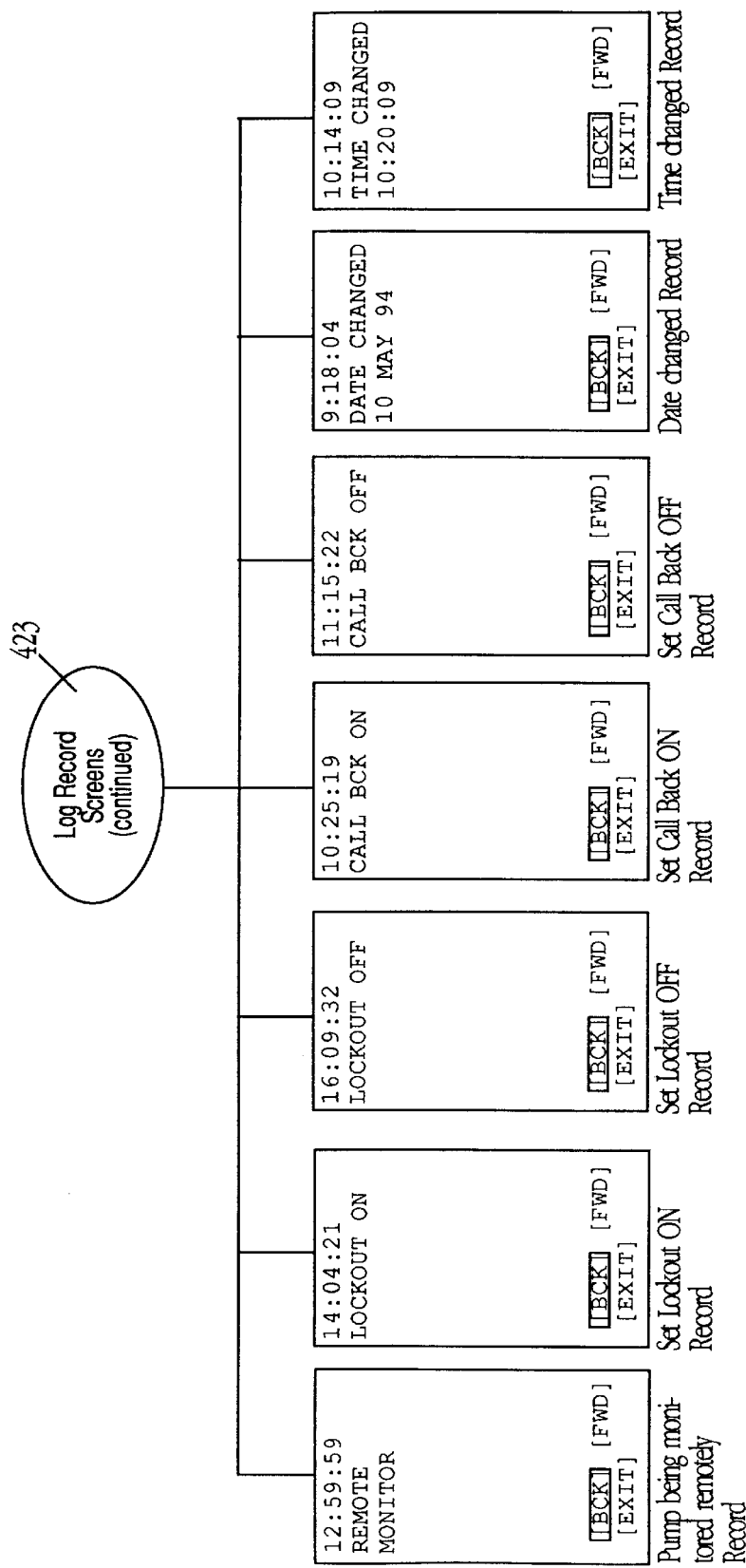

Each Log Record screen 423 display can include information regarding a transition from one functional state (Purge, Setup, Stop, Run or Bolus) to another. Any change made by the user to an Infusion Rate, Bolus Amount or Bolus Duration, and Dose Amount, Dose Duration, Number of Doses and Dose Interval is included in the Log Record screen 423 along with the value and units of the change. The installation of a new syringe is also included in the Log Record screen 423, as are date and time stamped alarms. Exemplary Log Record screens 423 are presented in FIGS. 65 and 66. Events or occurrences are recorded sequentially, enabling the user to scroll through the history of the pump in question using the "[BCK]" and "[FWD]" options. The Log is exited by selecting the "[EXIT]" option, returning the user to the first More screen 400. The entire Infusion Log may also be uploaded to a computer or host device via the RS-232 interface as described above.

These and other examples of the concept of the invention illustrated above are intended by way of example and the actual scope of the invention is to be determined from the following claims.

What is claimed is:

1. A syringe pump system comprising:
   a central control module in a housing having:
   a display screen;
   a syringe holding station for each of a plurality of drug syringes and holding each syringe in a plunger pushing position to said housing;
   a plunger pusher assembly for each said syringe holding station and operating under control of a controller for pushing a plunger of each syringe;
   a syringe display driver for said syringe holding stations providing plural syringe status and command menu displays in side-by-side relationship at different portions of said display screen;
   a command identification and select control for each syringe associated with a display portion allowing user creation of a drug administration regimen for each syringe associated with that display portion;
   a plunger pusher state selector associated with each display portion for controlling a plunger pusher state associated with each display portion; and
   a processor responsive to data from system components for applying operating data signals to said syringe display driver and said plunger pusher assembly.

2. The system of claim 1 wherein:
   said display is a red/green/blue color display; and
   said display driver is responsive to data from said processor to provide displays in green for a normal operating condition, in yellow for a warning condition, and in red for an alarm condition.

3. The system of claim 2 wherein said processor identifies alarms as non-recoverable alarms, including battery depleted, and as recoverable alarms, including syringe not correctly installed, and identifies warnings as recoverable faults including out-of-range setup information supplied, impending battery depletion, and impending syringe contents depletion.

4. The system of claim 1 wherein said display is a monochrome display, and said display driver is responsive to data from said processor to provide a display in normal video for normal operating conditions, and a display in inverse video for warning and alarm conditions.

5. The system of claim 1 wherein said command identification and select control further comprises a menu roam dial associated with each display portion, said processor being operative in response to dial rotation to step between selectable displayed commands and in response to further dial activation to cause selection of an identified command.

6. The system of claim 5 wherein said further dial activation is dial depression.

7. The system of claim 5 wherein said display driver provides layers of menus leading to selectable commands.

8. The system of claim 7 wherein the selectable commands are selected from the group of commands consisting of: specifying drug information, syringe identification, patient data, infusion rate, bolus information, dosage information, and timing information.

9. The system of claim 5 wherein the selectable commands include pressure ranges for generation of an alarm by said processor at limits of pressure in an infusion line.

10. The system of claim 9 wherein the processor includes a data output to the display driver to display a graphic representation of pressure in an infusion line.

11. The system of claim 1 further including:
    a function selector control in the plunger pusher state selector associated with each display portion,
    said processor responsive to activation of said function selector control to step between function states.

12. The system of claim 11 wherein said function states include purge, set-up, stop, run and bolus states.

13. The system of claim 12 wherein said processor is operative to change a current state based on determinations made by said processor in the presence of predetermined data.

14. The system of claim 11 wherein said processor is operative in response to received data, to prevent transition between function states under predetermined conditions determined by said processor from said data.

15. The system of claim 11, wherein said processor initiates one of a selected group of said function states only upon said activation of said function selector control and subsequent activation of said command identification and select control.

16. The system of claim 1 further comprising:
a memory for storing drug library information including plural data selected from the group of data on drug type, drug name, clinician, medical facility, and default administration parameters,
said processor operative to provide selected information from said memory to said display driver.

17. The system of claim 16 wherein said drug library information is employable by said processor in defining plural default infusion regimens associated with each drug name.

18. The system of claim 1 further including:
a memory having information provided by said processor representing data on prior infusions.

19. The system of claim 1 wherein said processor is operative to sequentially push fluid out of at least two syringes in separate syringe holding stations.

20. The system of claim 1 further comprising:
at least one volumetric pump module for enabling the continuous infusion of large liquid volumes from a large volume reservoir;
a liquid moving assembly for each said pump module and operating under control of a controller for moving a quantity of liquid through said pump module;
a command identification and select control for each volumetric pump module allowing user creation of a drug administration regimen for each module; and
a pump module state selector associated with each pump module for controlling,
wherein said processor is also for applying said operating data signals to said liquid moving assemblies, and
wherein said syringe display driver also provides plural status and command menu displays for said at least one volumetric pump module.

21. The system of claim 20 wherein said at least one volumetric pump module is selected from the group consisting of a peristaltic pump module and a volumetric cassette pumping module.

22. The system of claim 1 further comprising:
a battery for powering said syringe pump system; and
a battery management circuit for providing said processor with projected remaining battery life data for display as an updated time value on said display screen by said syringe display driver.

23. A syringe pump system comprising:
a central control module in a housing having:
a display screen;
at least one syringe holding station for a drug syringe and adapted to hold and identify a syringe of one of a plurality of sizes in a plunger driving position to said housing;
a pusher assembly for each said syringe holding station and operating under control of a controller for pushing a plunger of each syringe;
a syringe display driver for said at least one syringe holding station providing plural syringe status and command menu displays;
a command identification and select control for each syringe allowing user creation of a drug administration regimen for each syringe;
a pusher assembly state selector associated with each syringe for controlling a pusher assembly state associated with each syringe;
a processor responsive to data from system components for applying operating data signals to said syringe display driver and pusher assemblies; and
a communications link between said at least one syringe holding station and said processor, each said syringe holding station identifying to said processor the syringe size from among said plurality of sizes.

24. The system of claim 23 wherein said communications link further extends between each said pusher assembly and said processor, and wherein each said pusher assembly is adapted to accommodate syringes in the size range of 1 to 60 cc and to provide plunger location information to said processor.

25. A syringe pump system comprising:
a remote computer; and
a central control module in a housing having:
a display screen;
at least one syringe holding station for a drug syringe and adapted to hold a syringe of one of a plurality of sizes in a plunger pushing position adjacent to said housing;
a plunger pusher for each said syringe holding station and operating under control of a controller for pushing a plunger of each syringe;
a syringe display driver for said at least one syringe holding station providing plural syringe status and command menu displays;
a command identification and select control for each syringe holding station allowing user creation of a drug administration regimen for each syringe;
a plunger pusher state selector associated with each syringe for controlling a plunger pusher state associated with each syringe;
a processor responsive to data from system components for applying operating data signals to said syringe display driver and plunger pusher;
an interface to said remote computer for exchange of command and drug information data.

26. The system of claim 25 further comprising:
a memory associated with said processor; and
a data library importable from said remote computer via said interface to said memory for drug information including plural data selected from a group of data on drug type, drug name, clinician, medical facility, and default administration parameters,
wherein said data library is modified at said remote computer and downloaded to said syringe pump system.

27. A syringe pump system comprising:
a central control module in a housing having:
a display screen;
at least one syringe holding station for a drug syringe and adapted to hold a syringe of one of a plurality of sizes in a plunger pushing position to said housing;
a plunger pusher for each said syringe holding station and operating under control of a controller for pushing a plunger of each syringe;
a syringe display driver for each said syringe holding station providing plural syringe status and command menu displays;
a command identification and select control for each syringe allowing user creation of a drug administration regimen for each syringe;
a plunger pusher state selector associated with each syringe holding station for controlling a plunger pusher state associated with each syringe; and
a processor responsive to data from system components for applying operating data signals to said display and plunger pushers.

28. The system of claim 27, said plunger pusher having:

front and rear clamps notched to fit below a plunger flange and around the plunger of each syringe;

a load cell spaced from a top plate by a ball and located above the front and rear clamps to cradle the plunger flange therebetween;

an opening lever for separating the front and rear clamps to allow the plunger flange to be inserted therebetween; and linkage connecting the lever to the front and rear clamps to cause them to move under the plunger flange and centered about the plunger.

29. The system of claim 28 further including:

a connection for a signal from said load cell to said processor;

said processor operative to maintain a predetermined force on said plunger via said plunger pusher.

30. The system of claim 28 wherein the plunger pusher further includes:

a split nut disposed within said plunger pusher and driven on a drive screw to force the plunger flange into a syringe barrel of the syringe; and a linkage from said lever to the split nut for disengaging the split nut from said drive screw upon activation of the lever.

31. The system of claim 30 wherein said split nut is forced about the screw by a slidable lock plate having a bevel cut aperture through which the split nut is disposed, the aperture releases force on said split nut upon motion of the linkage under control of the lever, allowing the plunger pusher to be slipped up and down the drive screw with ease.

32. The system of claim 28 further including:

a connection for a signal from said load cell to said processor;

said processor operative to compare said signal from said load cell with a predetermined alarm threshold.

33. The system of claim 27 wherein said at least one syringe holding station further includes:

a syringe barrel clamp at said syringe holding station; and a paddle having linkage to the barrel clamp to allow one handed opening of the barrel clamp by activation of the paddle.

34. The system of claim 27 wherein said plunger pusher includes:

a DC motor coupled to push the plunger;

a charge pump for the motor operating in response to controls from said processor for pushing the plunger in response to push signals and providing fail safe operation whereby the failure of components in the plunger pusher substantially prevents a runaway push condition on the plunger.

35. The system of claim 34 wherein said processor provides run, brake, and strobe signals to the plunger pusher.

36. The system of claim 34 wherein said plunger pusher includes:

a drive screw in driving relationship with said motor;

a split nut forced about said screw by a sliding slot of a lock plate and by force of a biasing element disposed between said lock plate and said split nut, rotation of said drive screw causing said split nut to progress downward along said drive screw and causing said plunger to be pushed into a syringe barrel.

37. A syringe pump system comprising:

a central control module in a housing having:

a display screen;

at least one syringe holding station for a drug syringe and adapted to hold a syringe of one of a plurality of sizes in a plunger pushing position to said housing;

a plunger pusher for each said syringe holding station and operating under control of a controller for pushing a plunger of each syringe;

a syringe display driver for said at least one syringe holding station providing plural syringe status and command menu displays;

a command identification and select control for each syringe allowing user creation of a drug administration regimen for each syringe;

a plunger pusher state selector associated with each syringe holding station for controlling a plunger pusher state associated with each syringe;

a processor responsive to data from system components for applying operating data signals to said syringe display driver and plunger pushers; and a sensor for sensing pressure applied to the plunger by said plunger pusher, said processor operative to determine conditions in a line fed by said syringe in response to the plunger pressure sensed.

38. The system of claim 37 wherein said conditions determined include a break in an infusion line fed by said syringe.

39. The system of claim 37 wherein said sensor further comprises:

a load cell disposed within said plunger pusher and in communication with said processor via a communication path therebetween; and a substantially spherical interface element disposed proximate a syringe plunger, when said syringe is installed in said syringe holding station, and disposed adjacent said load cell, said interface element enabling detection of pressure applied to said syringe pusher by said load cell.

40. The system of claim 39 wherein said sensor further comprises a force receiving plate disposed intermediate and adjacent said interface element and said syringe pusher, when said syringe is installed in said syringe holding station.

41. The system of claim 37 wherein said processor comprises a variable pressure alarm mode wherein said processor provides an alarm output if a pressure sensed by said sensor and communicated to said processor is greater than a pressure, sensed by said sensor and communicated to said processor at a fixed time after initiation of infusion or averaged over a fixed period of time after initiation of infusion, plus an offset pressure value.

42. The system of claim 41 wherein said processor further comprises a memory and wherein said offset pressure value is predetermined and stored within said memory.

43. The system of claim 41 wherein said processor is provided with said offset pressure value via user-input at said time of pressure alarm mode initiation.

44. The system of claim 41 wherein said processor further comprises at least one fixed alarm mode in which, for each of said at least one alarm mode, said processor provides an alarm output if a pressure sensed by said sensor and communicated to said processor is greater than a respective predetermined pressure value stored in said memory.

45. A syringe pump system comprising:

a central control module in a housing having:

a display screen;

at least one syringe holding station for a drug syringe and adapted to hold a syringe of one of a plurality of sizes in a plunger pushing position to said housing;

a plunger pusher for each said syringe holding station and operating under control of a controller for pushing a plunger of each syringe;

a syringe display driver for said at least one syringe holding station providing plural syringe status and command menu displays;

a command identification and select control for each syringe allowing user creation of a drug administration regimen for each syringe;

a plunger pusher state selector associated with each syringe for controlling a plunger pusher state associated with each syringe; and a processor responsive to data from system components for applying operating data signals to said syringe display driver and plunger pushers, said processor controlled for selectively providing automated operation.

46. The system of claim 45, wherein said processor further includes memory associated with said processor, said processor control via a preset regimen stored in said memory.

47. The system of claim 45, wherein said processor control is via operator controlled operation of said command identification and select control and said plunger pusher state selector.

48. A syringe pump system comprising:

a central control module in a housing having:
   a display screen;
   at least one syringe holding station for a drug syringe and adapted to hold a syringe of one of a plurality of sizes in a plunger pushing position to said housing;
   a plunger pusher for each said syringe holding station and operating under control of a controller for pushing a plunger of each syringe;
   a syringe display driver for said at least one syringe holding station providing plural syringe status and command menu displays;
   a command identification and select control for each syringe allowing user creation of a drug administration regimen for each syringe;
   a plunger pusher state selector associated with each syringe holding station for controlling a plunger pusher state associated with each syringe;
   a processor in communication, via electrical pathways, with said display screen, each said syringe holding station, each said plunger pusher, said syringe display driver, each said command identification and select control, and each plunger pusher state selector, said processor responsive to data from system components for applying operating data signals to said display and plunger pushers;

said processor, via said electrical pathways, receiving syringe size from said holding station and plunger position signals from said plunger pusher, and providing in response thereto data to said syringe display driver for display including one or more data selected from the group of data consisting of time remaining in an infusion regimen, volume insufficient for bolus warning, low battery warning, remaining time on battery operation, depleted battery alarm, improper infusion regimen warning, improper syringe docking warning, plunger drive limit warnings, syringe empty alarm, line occlusion alarm, and syringe slipping in station alarm.

49. The system of claim 48 wherein said plunger drive limit warnings comprise data indicating that a respective syringe will be empty in a predetermined period of time at the current rate of infusion for said respective syringe.

50. A syringe pump system comprising:

a central control module in a housing having:
   a display screen;
   at least one syringe holding station for a drug syringe and adapted to hold a syringe of one of a plurality of sizes in a plunger pushing position to said housing;
   a plunger pusher for each said syringe holding station and operating under control of a controller for pushing a plunger of each syringe;
   a syringe display driver for said at least one syringe holding station providing plural syringe status and command menu displays;
   a command identification and select control for each syringe allowing user creation of a drug administration regimen for each syringe;
   a plunger pusher state selector associated with each syringe holding station for controlling a plunger pusher state associated with each syringe; and
   a processor responsive to data from system components for applying operating data signals to said syringe display driver and plunger pushers;
   the operating data signals for display including command selections in a format of volume over a set time and corresponding displays of the regimen in operation in said format.

51. A syringe pump system comprising:

a central control module in a housing having:
   a display screen;
   at least one syringe holding station for a drug syringe and adapted to hold a syringe of one of a plurality of sizes in a plunger pushing position to said housing;
   a plunger pusher for each said syringe holding station and operating under control of a controller for pushing a plunger of each syringe;
   a syringe display driver for said at least one syringe holding station providing plural syringe status and command menu displays;
   a command identification and select control for each syringe allowing user creation of a drug administration regimen for each syringe;
   a plunger pusher state selector associated with each syringe holding station for controlling a plunger pusher state associated with each syringe;
   an internal processor responsive to data from system components for applying operating data signals to said syringe display driver and said plunger pushers and further responsive to user input, via said command identification and select controls, of password and unit serial number data; and
   a memory of data including data on user language for use in data display, syringe sizes to be held at said station, default regimens for selected drugs, operating password and unit serial number used by said processor for preventing use of data from unapproved sources of additional data applied to the memory.

52. The syringe pump system of claim 51 further comprising:

an processor external to said central control module; and
an interface for exchange of commands and data between said internal processor and said external processor,
wherein said external processor executes a routine for customizing default regimens prior to downloading said regimens to said internal processor.

53. A syringe pump system comprising:

a central control module in a housing having:

a display screen;

a plurality of syringe holding stations each adapted to hold a syringe of one of a plurality of sizes in a plunger pushing position proximate said housing;

a plunger pusher for each said syringe holding station and for pushing a plunger of each syringe;

a syringe display driver for said at least one syringe holding station providing plural syringe status and command menu displays;

a command identification and select control for each syringe allowing user creation of a common drug administration regimen for a plurality of said plunger pushers;

a plunger pusher state selector associated with each syringe holding station for controlling a plunger pusher state of at least the associated syringe; and a processor responsive to data from system components for applying operating data signals to said syringe display driver and plunger pushers, said processor programmed to commence driving a first plunger pusher, to cease driving said first plunger pusher, and to commence driving a second plunger pusher.

54. The system of claim 53, wherein said processor ceases driving said first plunger and commences driving said second plunger in response to data from a pressure sensor disposed within said first plunger pusher.

55. The system of claim 53, wherein said processor ceases driving said first plunger and commences driving said second plunger in response to data from a timer circuit associated with said processor.

56. The system of claim 53, wherein said processor ceases driving said first plunger and commences driving said second plunger in response to data from a motion sensor associated with said first plunger pusher, said data indicative of a distance travelled by said first plunger pusher.

57. The system of claim 53 wherein said pressure sensor further comprises:

a load cell disposed within said plunger pusher and in communication with said processor via a communication path therebetween; and a substantially spherical interface element disposed proximate a syringe plunger, when said syringe is installed in said syringe holding station, and disposed adjacent said load cell, said interface element enabling detection of pressure applied to said syringe pusher by said load cell.

58. The system of claim 53, wherein said processor ceases driving said first plunger and commences driving said second plunger in response to data from a position sensor associated with said first plunger pusher, said data indicative of a distance travelled by said first plunger pusher.

59. The system of claim 58, wherein said processor ceases driving said second plunger and commences driving said first plunger in response to data from a position sensor associated with said second plunger pusher, said data indicative of a distance travelled by said second plunger pusher, and further in response to data indicating that a replacement syringe has been installed in a first syringe holding station corresponding to said first plunger pusher.

60. A plunger pusher module for use in a syringe pump, said plunger pusher module comprising:

a plunger module housing, a lock plate providing a vertically oriented bevel cut aperture therein, said lock plate disposed proximate a first vertical surface of said housing;

a spring biased split nut disposed through said lock plate bevel cut aperture, said split nut including a first threaded end extending outside said housing;

front and rear plunger clamps disposed in an upper portion of said housing for selective engagement about a syringe flange disposed therebetween, said clamps having a mechanical linkage therebetween whereby translation of said rear plunger clamp in a first direction results in translation of said front plunger clamp in an opposite second direction; and a lever shaft and associated linkage disposed within said housing wherein rotation of said lever shaft translates said rear plunger clamp in said first direction and translates said second plunger clamp in said opposite second direction, and further wherein rotation of said lever shaft actuates said associated linkage, resulting in translation of said lock plate bevel cut aperture with respect to said spring biased split nut, allowing said split nut first end to separate.

61. The plunger pusher module of claim 60, wherein said spring biased split nut first threaded end receives a vertical lead screw therein, whereby rotation of said lead screw when said first threaded end is in mechanical engagement thereabout results in vertical translation of said split nut, and consequently said plunger pusher module.

\* \* \* \* \*